US010787520B2

(12) United States Patent
Keyt et al.

(10) Patent No.: US 10,787,520 B2
(45) Date of Patent: Sep. 29, 2020

(54) MULTIMERIC BISPECIFIC BINDING MOLECULES SPECIFIC FOR CD20 AND CD3

(71) Applicant: IGM Biosciences, Inc., Mountain View, CA (US)

(72) Inventors: Bruce Alan Keyt, Hillsborough, CA (US); Omar Duramad, Berkley, CA (US); Beatrice Tien-Yi Wang, Mountain View, CA (US); Ramesh Baliga, Redwood City, CA (US); Fen Zhang, San Francisco, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 0 days.

(21) Appl. No.: 15/554,301

(22) PCT Filed: Mar. 4, 2016

(86) PCT No.: PCT/US2016/020920
§ 371 (c)(1),
(2) Date: Aug. 29, 2017

(87) PCT Pub. No.: WO2016/141303
PCT Pub. Date: Sep. 9, 2016

(65) Prior Publication Data
US 2019/0100597 A1    Apr. 4, 2019

Related U.S. Application Data

(60) Provisional application No. 62/128,284, filed on Mar. 4, 2015.

(51) Int. Cl.
*C07K 16/28* (2006.01)
*A61P 35/02* (2006.01)
*A61K 48/00* (2006.01)
*C12N 15/62* (2006.01)
*A61K 39/00* (2006.01)

(52) U.S. Cl.
CPC .......... *C07K 16/2887* (2013.01); *A61K 48/00* (2013.01); *A61P 35/02* (2018.01); *C07K 16/2809* (2013.01); *C12N 15/62* (2013.01); *A61K 2039/505* (2013.01); *C07K 2317/31* (2013.01); *C07K 2317/35* (2013.01); *C07K 2317/52* (2013.01); *C07K 2317/622* (2013.01); *C07K 2317/73* (2013.01); *C07K 2317/734* (2013.01); *C07K 2319/00* (2013.01); *C07K 2319/035* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly |
| 5,434,340 | A | 7/1995 | Krimpenfort |
| 5,798,229 | A | 8/1998 | Strittmatter |
| 6,165,463 | A | 12/2000 | Platz |
| 6,284,536 | B1 | 9/2001 | Morrison |
| 6,476,198 | B1 | 11/2002 | Kang |
| 7,074,403 | B1 | 7/2006 | Goldenberg |
| 7,109,304 | B2 | 9/2006 | Hansen |
| 7,138,496 | B2 | 11/2006 | Hua |
| 7,151,164 | B2 | 12/2006 | Hansen et al. |
| 7,282,567 | B2 | 10/2007 | Goldenberg |
| 7,311,912 | B1 | 12/2007 | Hein |
| 7,312,318 | B2 | 12/2007 | Hansen |
| 7,402,312 | B2 | 7/2008 | Rosen |
| 7,612,180 | B2 | 11/2009 | Goldenberg |
| 7,679,900 | B2 | 3/2010 | Lee |
| 7,709,615 | B2 | 5/2010 | Irie |
| 7,932,360 | B2 | 4/2011 | Van Berkel |
| 7,951,378 | B2 | 5/2011 | Larrick |
| 8,153,125 | B2 | 4/2012 | Watkins |
| 8,257,703 | B2 | 9/2012 | Irie |
| 8,337,844 | B2 | 12/2012 | Carr |
| 8,377,435 | B2 | 2/2013 | Bhat |
| 9,173,961 | B2 | 11/2015 | Deckert |
| 9,409,976 | B2 | 8/2016 | Teng |
| 9,458,241 | B2 | 10/2016 | Bhat |
| 9,938,347 | B2 | 4/2018 | Wang |
| 9,951,134 | B2 | 4/2018 | Keyt |
| 10,351,631 | B2 | 7/2019 | Keyt |
| 10,400,038 | B2 | 9/2019 | Keyt |
| 10,604,559 | B2 | 3/2020 | Carroll |
| 10,618,978 | B2 | 4/2020 | Keyt |
| 2002/0006630 | A1 | 1/2002 | Sirbasku |
| 2003/0224443 | A1 | 12/2003 | Hiatt |

(Continued)

FOREIGN PATENT DOCUMENTS

| | | |
|---|---|---|
| AU | 697387 | 3/1996 |
| EP | 2649184 | 10/2013 |

(Continued)

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*

(Continued)

*Primary Examiner* — Sharon X Wen

(57) ABSTRACT

This disclosure provides pentameric and hexameric CD20 binding molecules and methods of using such molecules to direct complement-mediated, T-cell-mediated, or both complement-mediated and T-cell-mediated killing of CD20-expressing cells.

Figure 2:
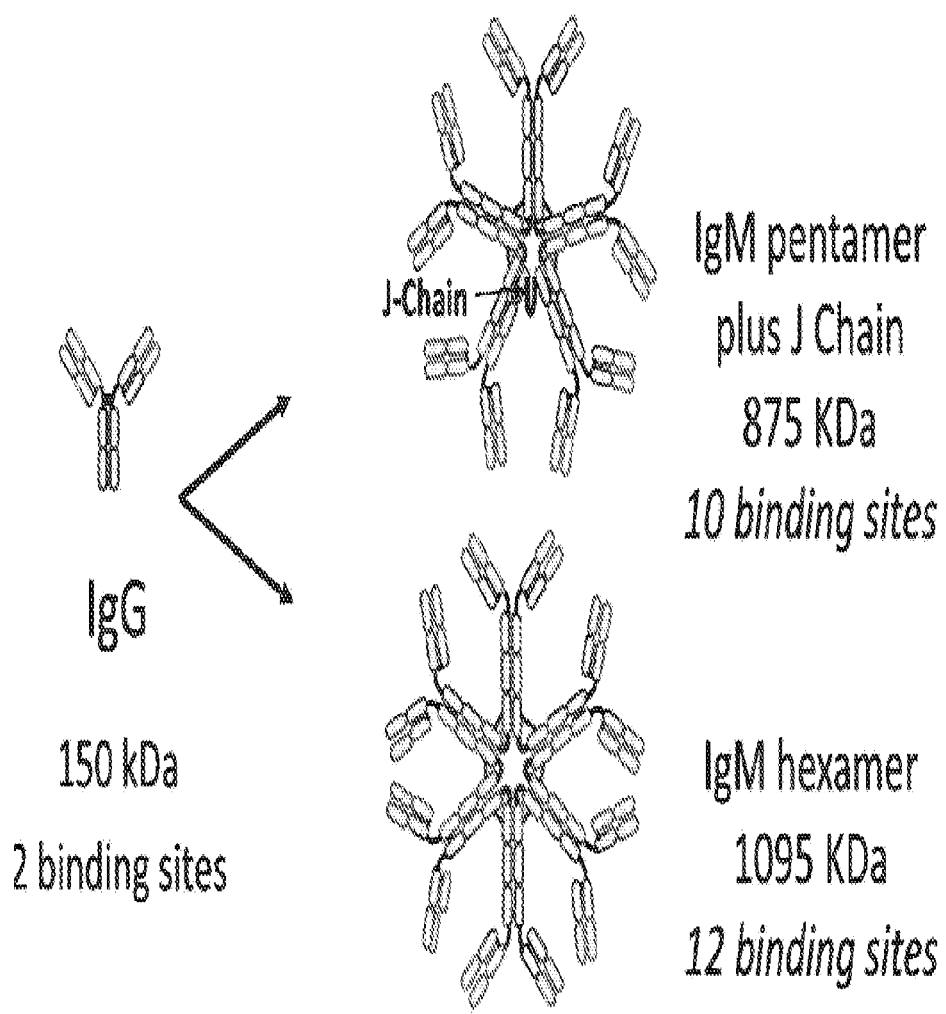

31 Claims, 16 Drawing Sheets
Specification includes a Sequence Listing.

(56) References Cited

U.S. PATENT DOCUMENTS

| | | |
|---|---|---|
| 2004/0005318 A1 | 1/2004 | Davis |
| 2005/0003431 A1 | 1/2005 | Wucherpfennig et al. |
| 2005/0129616 A1 | 6/2005 | Salcedo |
| 2005/0202026 A1 | 9/2005 | Hiatt |
| 2006/0063234 A1 | 3/2006 | Jones |
| 2006/0153854 A1 | 7/2006 | Bhat |
| 2007/0014720 A1 | 1/2007 | Gazit-Bornstein et al. |
| 2007/0154469 A1 | 7/2007 | Irie |
| 2007/0248601 A1 | 10/2007 | Cogne |
| 2007/0249812 A1 | 10/2007 | Hayasaka |
| 2008/0044413 A1 | 2/2008 | Hammond |
| 2008/0145420 A1 | 6/2008 | Simon |
| 2009/0022738 A1 | 1/2009 | Hofmeister |
| 2009/0130089 A9 | 5/2009 | Smith et al. |
| 2010/0093979 A1 | 4/2010 | Lazar |
| 2010/0172899 A1 | 7/2010 | Irie |
| 2010/0184959 A1 | 7/2010 | Guler-Gane et al. |
| 2010/0279932 A1 | 11/2010 | Ledbetter et al. |
| 2010/0279939 A1 | 11/2010 | Fries |
| 2011/0110852 A1 | 5/2011 | Miller |
| 2011/0129412 A1* | 6/2011 | Gazit-Bornstein ............ A61K 51/1027 424/1.11 |
| 2012/0045432 A9 | 2/2012 | Yu |
| 2012/0269830 A1 | 10/2012 | Horowitz |
| 2013/0095097 A1 | 4/2013 | Blankenship |
| 2013/0164283 A1 | 6/2013 | Bhat |
| 2013/0189258 A1 | 7/2013 | Rother |
| 2013/0280167 A1 | 10/2013 | Rodriguez |
| 2014/0010809 A1 | 1/2014 | Ledbetter |
| 2014/0044739 A1 | 2/2014 | Teng |
| 2014/0088295 A1 | 3/2014 | Smith et al. |
| 2014/0154252 A1 | 6/2014 | Thompson |
| 2014/0249044 A1 | 9/2014 | Braz Gonçalves |
| 2015/0004167 A1 | 1/2015 | Wu |
| 2015/0038682 A1 | 2/2015 | Tsurushita |
| 2015/0259420 A1 | 9/2015 | Triebel |
| 2016/0222132 A1 | 8/2016 | Keyt et al. |
| 2016/0326233 A1 | 11/2016 | Mondelli |
| 2016/0368971 A1 | 12/2016 | Keyt et al. |
| 2017/0183409 A1 | 6/2017 | Keyt et al. |
| 2017/0283510 A1 | 10/2017 | Keyt et al. |
| 2017/0320955 A1 | 11/2017 | Wang et al. |
| 2018/0009897 A1 | 1/2018 | Wang |
| 2018/0118814 A1 | 5/2018 | Carroll |
| 2018/0118816 A1 | 5/2018 | Keyt |
| 2018/0265596 A1 | 9/2018 | Keyt |
| 2019/0002566 A1 | 1/2019 | Keyt |
| 2019/0185570 A1 | 6/2019 | Keyt |
| 2019/0330360 A1 | 10/2019 | Wang |
| 2019/0330374 A1 | 10/2019 | Wang |
| 2019/0338031 A1 | 11/2019 | Keyt |
| 2019/0338040 A1 | 11/2019 | Keyt |
| 2019/0338041 A1 | 11/2019 | Baliga |
| 2020/0190190 A1 | 6/2020 | Keyt |

FOREIGN PATENT DOCUMENTS

| | | |
|---|---|---|
| EP | 2655415 | 10/2013 |
| EP | 2962103 | 1/2016 |
| WO | 1989001975 | 3/1989 |
| WO | 1998030591 | 7/1998 |
| WO | 1998030592 | 7/1998 |
| WO | 2004110143 | 12/2004 |
| WO | 2005103081 | 11/2005 |
| WO | 2006052641 | 5/2006 |
| WO | 2006/130458 A2 | 12/2006 |
| WO | 2013061098 | 5/2013 |
| WO | 2013087913 | 6/2013 |
| WO | 2013/120012 A2 | 8/2013 |
| WO | 2013120012 | 8/2013 |
| WO | 2013158748 | 10/2013 |
| WO | 2013188870 | 12/2013 |
| WO | 2014022592 | 2/2014 |
| WO | 2014124457 | 8/2014 |
| WO | 2014207064 | 12/2014 |
| WO | 2015037000 | 3/2015 |
| WO | 2015053887 | 4/2015 |
| WO | 2015053887 A1 | 4/2015 |
| WO | 2015103072 | 7/2015 |
| WO | 2015/120474 A1 | 8/2015 |
| WO | 2015120474 | 8/2015 |
| WO | 2015/153912 A1 | 10/2015 |
| WO | 2015151081 | 10/2015 |
| WO | 2015153912 | 10/2015 |
| WO | 2016/118641 A1 | 7/2016 |
| WO | 2016118641 | 7/2016 |
| WO | 2016/154593 A2 | 9/2016 |
| WO | 2016154593 | 9/2016 |
| WO | 2016/168758 A1 | 10/2016 |
| WO | 2016168758 | 10/2016 |
| WO | 2017/059380 A1 | 4/2017 |
| WO | 2017/059387 A1 | 4/2017 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |

OTHER PUBLICATIONS

Lamminmaki et al. (JBC 2001, 276:36687-36694).*
Kufer et al. (Trends in Biotechnology 2004 22:238-244).*
Wang et al. (Journal of Biotechnology 2007 129:726-731).*
Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.
Woof et al., "Structure and function relationshps in IgA", Mucosal Immunology, Nov. 2011, pp. 590-597, vol. 4, No. 6.
Baliga, R., et al., (2016) "High Avidity Anti-CD20 IgM Antibody for enhanced Complement-Dependent Cell Killing of Low CD20 Expressing Tumor Cells", Poster Presented at the PEGS Boston Meeting Apr. 25-29, 2016.
Johnson, R., et al. (2012) "Biological Activity of Anti-CD20 Multivalent HPMA Copolymer-Fab' Conjugates", Biomacromolecules, vol. 13, pp. 727-735.
Pascal, V., et al. (2012) "Anti-CD20 IgA can protect mice against lymphoma development: evaluation of the direct impact of IgA and cytotoxic effector recruitment on CD20 Target cells", Haematologica, the Hematology Journal, vol. 97(11), pp. 1686-1694.
Rossi, E., et al. (2008) "Novel Designs of Multivalent Anti-CD20 Humanized Antibodies as Improved Lymphoma Therapeutics", Cancer Res, vol. 68(20), pp. 8384-8392.
Sørensen, V., et al. (1999) "Structural requirements for incorporation of J Chain into human IgM and IgA", International Immunology, International Immunology, vol. 12(1), pp. 19-27.
Weiskopf, K., et al. (2013) "Engineered SIRPα Variants as Immunotherapeutic Adjuvants to Anticancer Antibodies", Science Express, vol. 341, pp. 89-91 with supplemental materials, 36 pages.
International Search Report and Written Opinion dated Aug. 31, 2016 issued in PCT Patent Application No. PCT/US2016/020920.
Cao, Y., et al., (2011), "Targeting cell surface β2-microglobulin by pentameric IgM antibodies", Br J Haematol, 154(1): 111-121.
Gaetano, N., et al., (2003), "Complement Activation Determines the Therapeutic Activity of Rituximab in Vivo", The Journal of Immunology, 171: 1581-1587.
Randall, T., et al., (1992), "Direct Evidence That J Chain Regulates the Polymeric Structure of IgM in Antibody-secreting B Cells", The Journal of Biological Chemistry, vol. 267(25), 18002-18007.

(56) References Cited

OTHER PUBLICATIONS

Wang, Y., et al., (2007), "The design, construction and function of a new chimeric anti-CD20 antibody", Journal of Biotechnology, 129: 726-731.
Bowles, J., et al., (2006), "Anti-CD20 monoclonal antibody with enhanced affinity for CD16 activates NK cells at lower concentrations and more effectively than rituximab", Blood, 108(8): 2648-2654.
Tabrizi, M., et al. (2010), "Biodistribution Mechanisms of Therapeutic Monoclonal Antibodies in Health and Disease", The AAPS Journal, vol. 12, No. 1, pp. 33-43.
Wajant, H. (2015), "Principles of antibody-mediated TNF receptor activation", Cell Death and Differentiation, 22: 1727-1741.
Arnold, J., et al., (2005), "Human serum IgM glycosylation: identification of glycoforms that can bind to mannan-binding lectin", The Journal of Biological Chemistry, vol. 280(32): 29080-29087.
Bacac, M., et al., (2018), "CD20-TCB with Obinutuzumab Pretreatment as Next-Generation Treatment of Hematologic Malignancies", Clinical Cancer Research, 24(19): 4785-4797, includes supplementary methods, Binding to CD20- and CD3-expressing cells, 24 additional pages.
Baliga, R., et al, (2019), "IGM-2323: High Avidity IgM-based CD20×CD3 Bispecific Antibody for Enhanced T-Cell Dependent Kiling with Minimal Cytokine Release", Abstract 1574 at American Society of Hematology Annual Meeting, Dec. 7-10, 2019, Orlando, FL.
Beers, S., et al., (2010), "Antigenic modulation limits the efficacy of anti-CD20 antibodies: implications for antibody selection", Blood, 115(25): 5191-5201.
Bornstein, G., et al., (2010), "Development of a new fully human anti-CD20 monoclonal antibody for the treatment of B-cell malignancies", Invest New Drugs, 28:561-574.
Bortoletto, N., et al., (2002), "Optimizing anti-CD3 affinity for effective T cell targeting against tumor cells", Eur. J. Immunol, 32: 3102-3107.
Brüggemann M., et al., (1987), "Comparison of the effector functions of human immunoglobulins using a matched set of chimeric antibodies", J. Exp. Med, 166: 1351-1361.
Castro, C., et al., (2014), "Putting J chain back on the map: how might its expression define plasma cell development?", The Journal of Immunology, 193: 3248-3255.
Chu, S., et al., (2014), "Immunotherapy with Long-Lived Anti-CD20×Anti-CD3 Bispecific Antibodies Stimulates Potent T Cell-mediated Killing of Human B Cell lines and Circulating and Lymphoid B Cells in Monkeys: A Potential Therapy for B Cell Lymphomas and Leukemias", Xencor, Inc., Monrovia, California 91016 USA, Poster.
Cregger, M., et al., (2006), "Immunohistochemistry and Quantitative Analysis of Protein Expression", Arch Pathol Lab Med., 130: 1026-1030.
Czuczman, M., et al., (2008), "Acquirement of rituximab resistance in lymphoma cell lines is associated with both global CD20 gene and protein down-regulation regulated at the pretranscriptional and posttranscriptional levels", Clin Cancer Res, 14(5): 1561-1570.
Davis, T., et al., (1999), "Single-agent monoclonal antibody efficacy in bulky non-Hodgkin's lymphoma: results of a phase II trial of rituximab", J. Clin Oncol. 17: 1851-1857.
Davis, T., et al., (2000), "Rituximab anti-CD20 monoclonal antibody therapy in non-Hodgkin's lymphoma: safety and efficacy of re-treatment", Journal of Clinical Oncology, 18(17): 3135-3143.
Ghielmini, M., (2004), "Prolonged treatment with rituximab in patients with follicular lymphoma significantly increases event-free survival and response duration compared with the standard weekly x 4 schedule", Blood, 103(12): 4416-4423.
Hagenbeek, A., et al., (2009), "Evaluation of Ofatumumab, a Novel Human CD20 Monoclonal Antibody, as Single Agent Therapy in Rituximab-Refractory Follicular Lymphoma", Blood, 114: 935, 6 pages.
Haidar, JH., et al. (2003), "Loss of CD20 expression in relapsed lymphomas after rituximab therapy", Eur J. Haematol, 70: 330-332.

Hensel, F., et al., (2013), "Early development of PAT-SM6 for the treatment of melanoma", 23(4): 264-275.
Hsu, D., et al., (1999), "A humanized anti-CD3 antibody, HuM291, with low mitogenic activity, mediates complete and reversible T-cell depletion in chimpanzees", Transplantation, 68(4): 545-554.
Klimovich, V. B., (2011), "IgM and Its Receptors: Structural and Functional Aspects", Biochemistry, 76(5): 534-549.
Liu, X., et al., (2005), "Recombinant of J chain-HNP-1 cDNA and the construction of expression vector", Di-San Junyi Daxue Xuebao, 27(8), 697-699. English Abstract Only Available.
Maloney, D., et al., (1997), "IDEC-C2B8 (Rituximab) anti-CD20 monoclonal antibody therapy in patients with relapsed low-grade non-Hodgkin's lymphoma", Blood, 90(6): 2188-2195.
Mandikian, D., et al., (2018), "Relative Target Affinities of T Cell-Dependent Bispecific Antibodies Determine Biodistribution in a Solid Tumor Mouse Model", Mol Cancer Ther., 17(4):776-785, doi: 10.1158/1535-7163. MCT-17-0657.
Marcus, R., et al., (2017), "Obinutuzumab for the First-Line Treatment of Follicular Lymphoma", N Engl. J. Med. 377(14): 1331-44.
Mølhøj, M., et al., (2007), "CD19-/CD3-bispecific antibody of the BiTE class is far superior to tandem diabody with respect to redirected tumor cell lysis", Molecular Immunology 44: 1935-1943.
Niles, M., et al., (1995), "Polymer IgM assembly and secretion in lymphoid and nonlymphoid cell lines: evidence that J chain is required for pentamer IgM synthesis", Proc. Natl. Acad. Sci. USA, 92: 2884-2888.
Rasche, L., et al., (2015), "GRP78-directed immunotherapy in relapsed or refractory multiple myeloma—results from a phase 1 trial with the monoclonal immunoglobulin M antibody PAT-SM6", Haematologica, J. Mol. Biol, 100(3): 377-384.
Rezvani, A., et al., (2011), "Rituximab Resistance", Best Pract Res Clin Haematol, 24(2): 203-216.
Saber, H., et al., (2017), "An FDA oncology analysis of CD3 bispecific constructs and first-in-human dose selection", Regulatory Toxicology and Pharmacology, 90: 144-152.
Smith, E., et al., (2015), "A novel, native-format bispecific antibody triggering T-cell killing of B-cells is robustly active in mouse tumor models and cynomolgus monkeys", Scientific Reports, 5: 17943, 12 pages.
Strohl, W., et al., (2015), "Fusion Proteins for Half-Life Extension of Biologics as a Strategy to Make Biobetters", BioDrugs, 29: 215-239.
Sun, L., et al., (2015), "Anti-CD20/CD3 T cell-dependent bispecific antibody for the treatment of B cell malignancies", Immunotherapy, vol. 7(287), 287ra70, 11 pages.
Teachey, D., et al., (2013), "Cytokine release syndrome after blinatumomab treatment related to abnormal macrophage activation and ameliorated with cytokine directed therapy", Blood Journal, DOI 10.1182/blood-2013-02-485623.
van Imhoff, G., et al. (2017), "Ofatumumab Versus Rituximab Salvage Chemoimmunotherapy in Relapsed or Refractory Diffuse Large B-Cell Lymphoma: The ORCHARRD Study", Journal of Clinical Oncology, 35(5): 544-551.
Vitolo, U., et al. (2017), "Obinutuzumab or Rituximab Plus Cyclophosphamide, Doxorubicin, Vincristine, and Prednisone in Previously Untreated Diffuse Large B-Cell Lymphoma", Journal of Clinical Oncology, 35(31): 3529-3537.
Wing, M., (2008), "Monoclonal Antibody First Dose Cytokine Release Syndromes—Mechanisms and Prediction", Journal of Immunotoxicology, 5: 11-18.
Wu, J., et al., (2015), "Blinatumomab: a bispecific T cell engager (BiTE) antibody against CD19/CD3 for refractory acute lymphoid leukemia", Journal of Hematology & Oncology, 8:104, DOI 10.1186/s13045-015-0195-4, 7 pages.
Albrecht, H., et al. (2006), "Recombinant Antibodies: From the Laboratory to the Clinic", Cancer Biotherapy & Radiopharmaceuticals, vol. 21: 285-304.
Ammann, J., et al. (2014), "Development and use of IgM/J-Chain Fusion Proteins for Chacterization of Immunoglobulin Superfamily Ligand-Receptor Interactions", Current Protocols in Protein Science, 19.24.1-19.24.11, Supplement 75.

(56) References Cited

OTHER PUBLICATIONS

Ammann, J., et al., (2012), "Detection of weak receptor-ligand interactions using IgM and J-chain-based fusion proteins", European Journal of Immunology, 42:1354-1356.

Azuma, Y., et al., "Recombinant Human Hexamer-Dominant IgM Monoclonal Antibody to Ganglioside GM3 for Treatment of Melanoma", 2007, Clin Cancer Res, vol. 13 (No. 9), pp. 2745-2750 with correction on article.

Bakema et al, "Immunoglobulin A, A next generation of therapeutic antibodies?", mAbs, Aug. 2011, vol. 3, No. 4, 352-361.

Braathen, R., et al. (2002), "The Carboxyl-terminal Domains of IgA and IgM Direct Isotype-specific Polymerization and Interaction with the Polymeric Immunoglobulin Receptor", The Journal of Biological Chemistry, vol. 277, No. 45, pp. 42755-42762.

Cao, Y., et al., (2011), "Targeting cell surface Beta2-microglobulin by pentameric IgM antibodies", British Journal of Haematology, 154: 111-121.

Chintalacharuvu et al., "Hybrid IgA2/igG1 Antibodies with Tailor-Made Effector Functions", Clinical Immunology, Oct. 2001, pp. 21-31, vol. 101, No. 1, pp. 21-31.

Clackson et al., "Making antibody fragments using phage display libraries" Nature 1991, vol. 352, pp. 624-628.

Czajkowsky and Shao, "The human IgM pentamer is a mushroom-shaped molecule with a flexural bias," PNAS 2009, vol. 106, No. 35, pp. 14960-14965.

Davis et al., "On the structure of polymeric IgM," Eur. J. Immunol. 1988, vol. 18, No. 7, pp. 1001-1008.

Davis, A., et al., (1989), "IgM—Molecular requirements for its assembly and function", Immunology Today, 10(4): 7 pages.

Dorai et al, "The complete nucleotide sequence of a human immunoglobulin genomic Cu gene," GenBank Accession No. X14940.1, Nucleic Acids Research 1989, vol. 17, No. 15, p. 6412.

Fournier et al., "Bispecific antibodies and trispecific immunocytokines for targeting the immune system against cancer: preparing for the future," BioDrugs. 2013, vol. 27, No. 1, pp. 35-53.

Frutiger, S., et al., 1992, "Disulfide Bond Assignment in Human J Chain and its Covalent Pairing with Immunoglobulin M", Biochemistry, vol. 31, pp. 12643-12647.

Fukushima, N., et al., (2002), "Chacterization of Recombinant Monoclonal IgA Anti-PDC-E2 Autoantibodies Derived From patients with PBC", Hepatology: 35: 1383-1392.

Garcia-Pardo et al., "J chain is covalently bound to both monomer subunits in human secretory IgA," J. Biol. Chem. 1981, vol. 256, pp. 11734-11738.

Gilmour, J.E.M., et al. (2008), "Effect of the presence or absence of J Chain on expresion of recombinant anti-kell immunoglobulin", Transfusion Medicine, 18: 167-174.

Goswami et al., "Developments and challenges for mAb-Based therapeutics," Antibodies 2013, vol. 2, No. 3, pp. 452-500.

Hirayasu, K. and Arase, H., "Immunoglobulin mu heavy chain, partial [Homo sapiens]," GenBank Accession No. AFM37312, Jun. 18, 2012 (2 pages).

Johansen, F., et al., (2000), "Role of J Chain in Secretory Immunoglobulin Formation", Scand. J. Immunol., 52: 240-248.

Johansen, F., et al. (2001), "The J Chain Is Essential for Polymeric Ig Receptor-Mediated Epithelial Transport of IgA", The Journal of Immunology, 167: 5185-5192.

Jones et al, "Replacing the complementarity-determining regions in a human antibody with those from a mouse," Nature 1986, vol. 321, pp. 522-525.

Kragten, E., et al., (1995), "Site-specific analysis of the N-Glycans on Murine Polymeric Immunoglobulin A. Using Liquid Chromatography/Electrospray Mass Spectrometry", vol. 30, 1679-1686.

Krugmann, S., et al. (1997), "Structural Requirements for Assembly of Dimeric IgA Probed by Site-Directed Mutagenesis of J Chain and a Cysteine Residue of the α-chain CH2 Domain", The Journal of Immunology, 159: 244-249.

Liedtke, M., et al., (2012), "Phase I trial of a novel human monoclonal antibody mAb216 in patients with relapsed or refractory B-cell acute lymphoblastic leukemia" Haematologica 97, 30-37.

Liu, Xianhua, et al., 2006, "Expression Detection of the gene of α-defensin-1 with J chain in the transfected COS-7 cells", Chin Crit Care Med, vol. 18, No. 2, pp. 71 to 73 with Full English translation.

Mariuzza, R. A., (1987), "The Structural Basis of Antigen-Antibody Recognition", vol. 16: 139-159.

Mestecky, J., et al., (1973), "J-chain of polymeric IgA myeloma proteins", Protides of the Biological Fluids, vol. 20: 279-283 , Abstract Only Available.

Mongini, P., et al., (1995), "Human B Cell Activation, Effect of T Cell Cytokines on the Physicochemical Binding Requirements for Achieving Cell cycle Progression Via the Membrane IgM Signaling Pathway", The Journal of Immunology, 155: 3385-3400.

Mosmann, T.R., et al. (1978), "Modification and Fate of J. Chain in myeloma cells in the presence and absence of polymeric immunoglobulin secretion", Eur. J. Immunol. 8: 84-101.

NCBI Reference Sequence: NP_653247.1, Apr. 17, 2013, Immunoglobulin J chain precursor [Homo sapiens].

Palanichamy Arumugam et al, "Rituximab efficiently depletes increased CD20-expressing T cells in multiple sclerosis patients.", Journal of Immunology (Baltimore, MD.: 1950) Jul. 15, 2014, (Jul. 15, 2014), vol. 193, No. 2, pp. 580-586.

Rabbitts et al. "Human immunoglobulin heavy chain genes: evolutionary comparisons of C mu, C delta and C gamma genes and associated switch sequences," GenBank Accession No. CAB37838, Nucleic Acids Research 1981 vol. 9, No. 18, pp. 4509-4524.

Raju et al., "Potential therapeutic roles for antibody mixtures," Exp. Op. Biol. Ther. 2013, vol. 13, No. 10, pp. 1347-1352.

Redwan, E., et al. (2006), "Recombinant human J-chain: fix the protein aggregations and yield maximize" Human Antibodies 15, 95-102.

Riechmann et al., "Reshaping human antibodies for therapy," Nature 1988, vol. 332, pp. 323-329.

Seifert, O., et al., (2012), "The IgM CH2 domain as covalently linked homodimerization module for the generation of fusion proteins with dual specificty", Protein engineering, Design & Selection, vol. 25(10): 603-612.

Smith, R. et al., (1995), "Addition of a mu-tailpiece to IgG results in polymeric antibodies with enhanced effector functions including complement-mediated cytolysis by IgG4" The Journal of Immunology 154, 2226-2236.

Symersky, J., et al., (2000), "Expression of the recombinant human immunoglobulin J Chain in Escherichia coli", Molecular Immunology, 37: 133-140.

Tavolaro, S., et al. (2013), "IgD cross-linking induces gene expression profiling changes and enhances apoptosis in chronic lymphocytic leukemia cells", Leukemia Research, 37: 455-462.

Tchoudakova, A., et al., 2009, "High level expression of functional human IgMs in human PER.C6 cells", MAbs 1, 163-171.

Tussiwand, R., et al., (2012), "BAFF-R expression correlates with positive selection of immature B cells", European Journal of Immunology, 42: 206-216.

Wang, W., et al. (2008), "Monoclonal Antibody Pharmacokinetis and Pharmacodynamics", State of the Art, vol. 84, No. 5, pp. 548-558.

Wood, C.R., et al., (1990), "High level synthesis of immunoglobulins in Chinese hamster ovary cells". J. Immunol. 145, 3011-3016.

Yoo et al., "Structural requirements for polymeric immunoglobulin assembly and association with J chain," J. Biol. Chem. 1999, vol. 274, No. 47, pp. 33771-33777.

Meyer et al., "Improved In Vivo Anti-Tumor Effects of IgA-Her2 Antibodies Through Half-Life Extension and Serum Exposure Enhancement by FcRn Targeting", mAbs, Jan. 2016, pp. 87-98, vol. 8, Issue 1.

\* cited by examiner

Figure 1
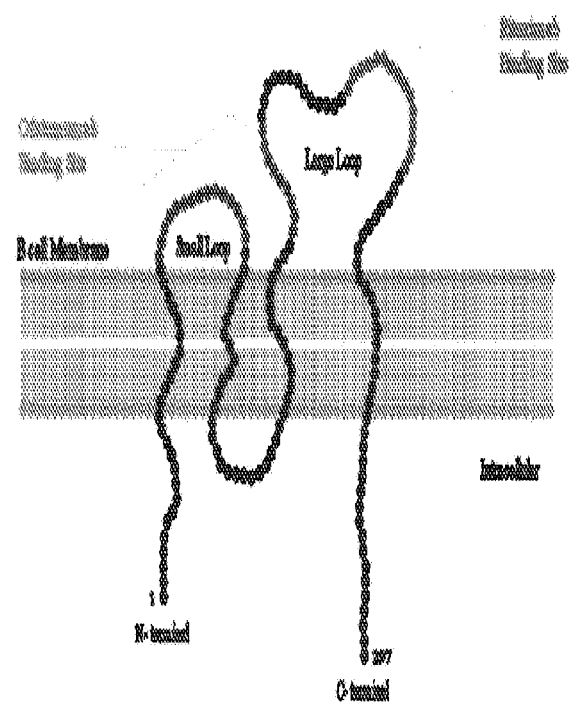

Figure 10
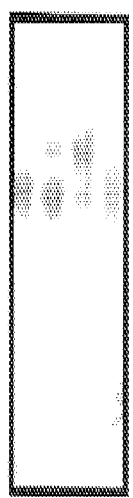
Fig. 10A
2 3 4 1
Hybrid
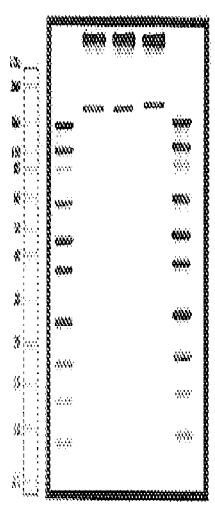
Fig. 10B
1 2 3 4 5
Non-reducing
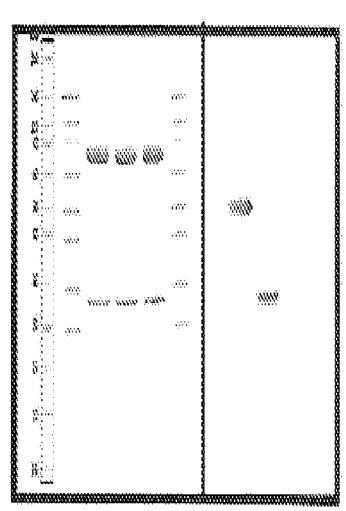
Fig. 10C          Fig. 10D
1 2 3 4 5        1 2 3 4 5
Reducing          Western
1 Marker
2 1.5.3 IgM+V15J
3 1.5.3 IgM+wtJ
4 1.5.3 IgM
5 Marker Figure 14
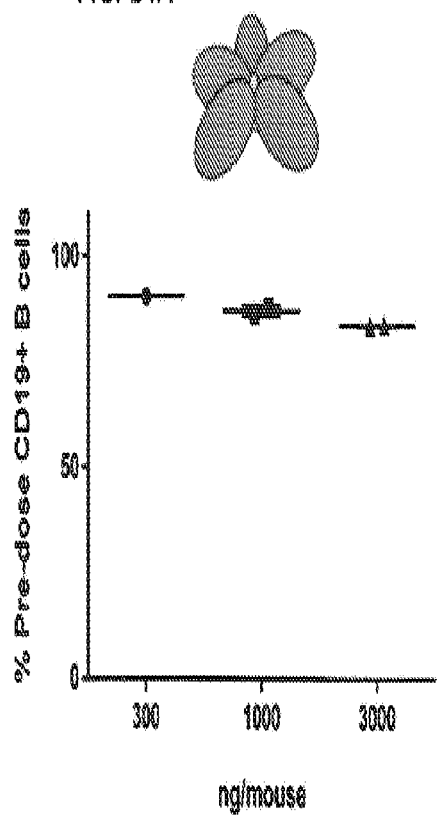
FIG. 14A
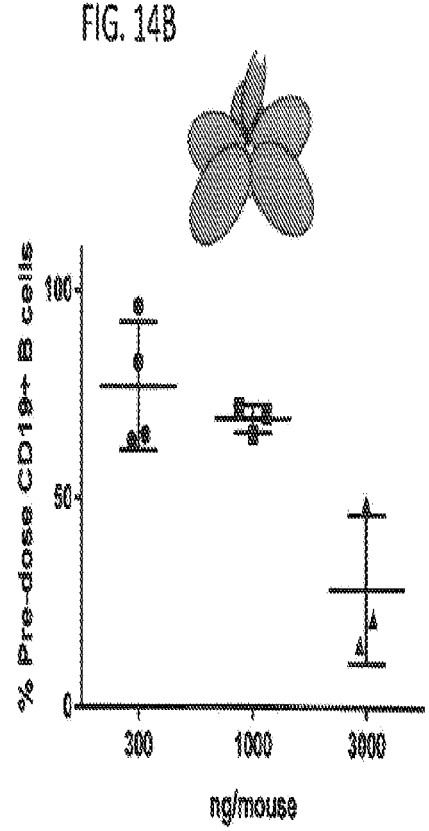
FIG. 14B

MULTIMERIC BISPECIFIC BINDING MOLECULES SPECIFIC FOR CD20 AND CD3

CROSS-REFERENCE TO RELATED APPLICATIONS

This application is a US National Stage Entry of PCT Application No. PCT/US2016/020920, filed Mar. 4, 2016, which claims benefit to U.S. Provisional Appl. No. 62/128,284, filed on Mar. 4, 2015; the content of each are hereby incorporated by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Aug. 29, 2017, is named 57912-169241_SequenceListing_August_2017S.txt and is 95923 bytes in size.

BACKGROUND

Since the advent of humanized antibodies, the therapeutic use of antibodies such as RITUXAN® (rituximab) has revolutionized the treatment of B-cell malignancies. Rituximab, a CD20 specific chimeric monoclonal antibody, is the first effective targeted therapy approved by the FDA for treatment of relapsed or refractory B-cell non-Hodgkin's lymphoma. This scientific achievement has not only changed the standard of practice for treatment of B-cell lymphoma but has stimulated significant interest in next generation of CD20 mAbs. Many novel CD20 mAbs have entered the clinic, each with structural modifications to further improve efficacy. In this application, we describe a series of CD20 antibodies that can exhibit improved efficacy utilizing additional modes of action, as these CD20 antibodies are expressed in non-IgG formats, such as IgA and IgM.

CD20 is a 36 kDa non-glycosylated; tetra-spanning membrane protein (MS4A1 gene product) expressed exclusively on B-lymphocytes and more than 90% of B-lymphocytic lymphoma (see FIG. 1). CD20 is expressed at the late pre-B cell stage and is upregulated on most normal and malignant B lineage cells before it is down-regulated in terminally differentiated plasma cells. This B-lymphocyte surface molecule is involved with development and differentiation of B-cells into plasma cells.

Although rituximab exhibits significant anti-tumor activity in patients with B-cell non-Hodgkin's lymphoma, there is a need to improve the efficacy of antibody therapeutics for the treatment of B-cell neoplasms. Rituximab as single agent therapy results in a clinical response rate of 50%, and it is unclear why the remaining 50% of patients do not respond. In addition, a majority of responsive patients acquires resistance to further rituximab therapy. One mechanism of initial or acquired resistance is the down regulation or modulation of CD20 on the tumor cells (or clonal expansion of low expressing tumors). There is a clear unmet medical need for improved treatment for these refractory patients whose refractory tumors have minimizes CD20 expression. By increasing affinity and avidity with the multivalency of IgA or IgM, these newer agents aim to achieve improved response rates as compared to rituximab. Furthermore, altering the effector functions by changing the antibody isotype may improve the potency and efficacy of CD20 antibodies.

Since the introduction of rituximab, much has been learned about potential mechanisms for the therapeutic efficacy of CD20 mAbs. Rituximab induces B-cell death primarily through complement-dependent lysis (CDC) and antibody dependent cellular toxicity (ADCC) effector mechanisms, and to a lesser degree via cellular apoptosis. CD20 antibodies are described as either Type I (such as rituximab/RITUXAN® or ofatumumab/ARZERRA®), which redistributes CD20 into detergent-resistant lipid rafts; and Type II such as tositumumab (B1) and obinutuzumab/GAZYVA®, which do not. Clustering by Type I antibodies promotes association with other cell surface proteins such as the B-cell receptor (BCR), and binding to C1q, resulting in potent complement-dependent cytotoxicity (CDC). IgM is highly potent at inducing complement dependent cytotoxicity, and as such IgM forms of CD20 antibodies can yield significantly greater efficacy. In contrast, Type II antibodies, such as tositumomab (B1), elicit antibody-dependent cellular cytotoxicity, but not complement-dependent cytotoxicity. Type II antibodies are very potent at directly triggering cell death via antibody-induced homotypic adhesion and lysosomal cell death. Oligomeric forms of antibodies, such as IgA and IgM exhibit increased multivalency and can display enhanced efficacy at inducing homotypic adhesion and cell death. Importantly, both type I and type II antibodies recruit FcR-expressing cells to mediate cellular effector functions such as antibody-dependent cellular cytotoxicity and antibody-dependent cellular phagocytosis.

Second-generation type I CD20 mAbs have been approved for human use. Ofatumumab is a fully human IgG1, type I CD20 mAb that exhibits antibody dependent cellular cytotoxicity (ADCC) but has stronger complement-dependent cytotoxicity (CDC) when compared to rituximab. As a type I antibody, ofatumumab is relatively ineffective in triggering cell death. Ofatumumab is FDA approved for treatment of chronic lymphocytic leukemia (CLL). Obinutuzumab/GA101 is a humanized IgG1 second-generation type II mAb which displays improved pro-apoptotic activity, enhanced ADCC but no complement-fixing activity. Obinutuzumab is FDA approved for treatment CLL. Another fully human IgG1K CD20 antibody huMAb 1.5.3 (see U.S. Patent Publication No. 2007-0014720), was designed for enhance potency. Preclinical studies have shown that huMAb 1.5.3 has greater apoptosis as compared to rituximab and exhibits both potent CDC as well as ADCC activity. HuMAb 1.5.3 appears to combine both type I and type II activities including effective cell killing through direct apoptosis induction, CDC and ADCC. IgM and IgA can contribute to further enhanced potency of CD20 antibodies with increased avidity which can mediate increased sensitivity and cytotoxicity on low CD20 expressing tumor cells. Furthermore, the efficacy of type I and type II CD20 activities can be increased with IgA or IgM formats allowing the development of most potent anti-tumor antibodies utilizing optimally combined mechanisms of action, including the triggering direct apoptosis, enhanced CDC and ADCC.

SUMMARY

This disclosure provides a multimeric binding molecule that includes at least two bivalent binding units or variants or fragments thereof, where each binding unit includes at least two heavy chain constant regions or fragments thereof, each associated with an antigen-binding domain. At least one antigen binding domain of the provided binding molecule is a CD20 antigen binding domain that includes six immunoglobulin complementarity determining regions HCDR1, HCDR2, HCDR3, LCDR1, LCDR2, and LCDR3, where the HCDR1 includes the amino acid sequence of SEQ ID NO: 39 or SEQ ID NO: 39 with one or two single amino acid substitutions; the HCDR2 includes the amino acid sequence of SEQ ID NO: 40 or SEQ ID NO: 40 with one or two single amino acid substitutions; the HCDR3 includes the amino acid sequence of SEQ ID NO: 41, SEQ ID NO: 41 with one or two single amino acid substitutions; the LCDR1 includes the amino acid sequence of SEQ ID NO: 43, or SEQ ID NO: 43 with one or two single amino acid substitutions; the LCDR2 includes the amino acid sequence of SEQ ID NO: 44 or SEQ ID NO: 44 with one or two single amino acid substitutions; and the LCDR3 includes the amino acid sequence of SEQ ID NO: 45 or SEQ ID NO: 45 with one or two single amino acid substitutions.

The disclosure further provides a multimeric binding molecule that includes at least two bivalent binding units or variants or fragments thereof, where each binding unit includes at least two heavy chain constant regions or fragments thereof, each associated with an antigen-binding domain. At least one antigen binding domain of the provided binding molecule is a CD20 antigen binding domain that includes an antibody heavy chain variable region (VH) and an antibody light chain variable region (VL), where the VH includes an amino acid sequence at least 80%, at least 85%, at least 90%, at least 95% or 100% identical to SEQ ID NO: 38, and the VL includes an amino acid sequence at least 80%, at least 85%, at least 90%, at least 95% or 100% identical to SEQ ID NO: 42.

In certain aspects a binding molecule provided by the disclosure is a dimeric binding molecule that includes two bivalent IgA binding units or fragments thereof and a J-chain or fragment or variant thereof, where each binding unit includes two IgA heavy chain constant regions or fragments thereof each associated with an antigen-binding domain. A dimeric IgA binding molecule as provided herein can further include a secretory component, or fragment or variant thereof. The IgA heavy chain constant regions or fragments thereof can each include a Cα2 domain or a Cα3-tp domain and can, in certain aspects, further include a Cα1 domain. In certain aspects, the IgA heavy chain constant regions can be human IgA constant regions. In certain aspects, each binding unit includes two IgA heavy chains each including a VH situated amino terminal to the IgA constant region or fragment thereof, and two immunoglobulin light chains each including a VL situated amino terminal to an immunoglobulin light chain constant region.

In certain aspects a binding molecule provided by the disclosure is a is a pentameric or a hexameric binding molecule including five or six bivalent IgM binding units, respectively, where each binding unit includes two IgM heavy chain constant regions or fragments thereof each associated with an antigen-binding domain. The IgM heavy chain constant regions or fragments thereof can each include a Cμ3 domain and a Cμ4-tp domain and can, in certain aspects further include a Cμ2 domain, a Cμ1 domain, or any combination thereof.

Where the binding molecule is pentameric, the binding molecule can further include a J-chain, or fragment thereof, or functional fragment thereof, or a functional variant thereof. In certain aspects, the J-chain or fragment thereof includes the amino acid sequence SEQ ID NO: 49 or a functional fragment thereof. In certain aspects, the J-chain or fragment thereof can further include a heterologous polypeptide. The heterologous polypeptide can be directly or indirectly fused to the J-chain or fragment thereof. In certain aspects the heterologous polypeptide can be indirectly fused to the J-chain or fragment thereof via a peptide linker. In certain aspects the peptide linker can include, e.g., at least 5 amino acids, but no more than 25 amino acids. In certain aspects the peptide linker consists of GGGGSGGGGSGGGGS (SEQ ID NO: 67). The heterologous polypeptide can be fused to or near the N-terminus of the J-chain or fragment thereof, the C-terminus of the J-chain or fragment thereof, or to both the N-terminus and C-terminus of the J-chain or fragment thereof. In certain aspects the heterologous polypeptide can include a binding domain, e.g., an antibody or antigen-binding fragment thereof. The antigen-binding fragment can be, for example, a Fab fragment, a Fab' fragment, an F(ab')2 fragment, an Fd fragment, an Fv fragment, a single-chain Fv (scFv) fragment, a disulfide-linked Fv (sdFv) fragment, or any combination thereof. In certain aspects the heterologous polypeptide can specifically bind to CD3ε. For example, in certain aspects the modified J-chain can include the amino acid sequence SEQ ID NO: 64 (V15J) or SEQ ID NO: 66 (J15V). Moreover, in certain aspects, these particular modified J-chains can further include a signal peptide, where the modified J-chain then includes the amino acid sequence SEQ ID NO: 63 (V15J) or SEQ ID NO: 65 (J15V).

In certain aspects, the IgM heavy chain constant regions can be human IgM heavy chain constant regions. In certain aspects, each binding unit includes two IgM heavy chains each including a VH situated amino terminal to the IgM constant region or fragment thereof, and two immunoglobulin light chains each including a VL situated amino terminal to an immunoglobulin light chain constant region.

In certain aspects, at least one binding unit of a multimeric binding molecule provided herein includes two of the CD20 antigen binding domains, which can be the same or different. In certain aspects, at least three, at least four, at least five, at least six, at least seven, at least eight, at least nine, at least ten, at least eleven, or at least twelve copies of the same CD20 antigen binding domain.

In certain aspects where the binding molecule is an IgM binding molecule, the two IgM heavy chains within at least one binding unit include the amino acid sequence SEQ ID NO: 56.

In certain aspects where the binding molecule includes immunoglobulin light chains, the two light chain constant regions of a given binding unit can be human lambda constant regions or a human kappa constant region. In certain aspects the two light chain constant regions are identical and include the amino acid sequence SEQ ID NO: 58.

In certain aspects, at least two, at least three, at least four, at least five, or at least six of the binding units of a multimeric binding molecule provided herein are identical.

In certain aspects, the binding molecule as described above can direct complement-mediated, T-cell-mediated, or both complement-mediated and T-cell-mediated killing of a CD-20-expressing cell at higher potency than an equivalent amount of a monospecific, bivalent IgG1 antibody or fragment thereof that specifically binds to the same CD20 epitope as the one or more CD20 antigen binding domains of the binding molecule. In certain aspects, the monospecific, bivalent IgG1 antibody is 1.5.3, which includes a VH having the amino acid sequence SEQ ID NO: 38 and a VL having the amino acid sequence SEQ ID NO: 42. In certain aspects, the CD-20-expressing cell is a lymphoma cell line, for example, a Ramos cell line, a Raji cell line, a Daudi cell line, a Namalwa cell line, a Granta cell line, a Z138 cell line, a DoHH2 cell line, or a DB cell line. In certain aspects, where the CD20-expressing cell is a Raji cell line, the binding molecule can direct complement-mediated killing with an $IC_{50}$ at least four-fold, at least ten-fold, at least 50-fold, or at least 100-fold lower than the $IC_{50}$ of an equivalent amount of the monospecific bivalent IgG1 antibody, as measured, e.g., in µg/ml. In certain aspects, where the CD20-expressing cell is a Ramos cell line, the binding molecule can direct complement-mediated killing with an $IC_{50}$ at least ten-fold, at least 20-fold, at least 30-fold, at least 40-fold, at least 50-fold, at least 60-fold, at least 70-fold, at least 80-fold, at least 90-fold, or at least 100-fold lower than the $IC_{50}$ of an equivalent amount of the monospecific bivalent IgG1 antibody, as measured, e.g., as molar equivalents. In certain aspects, the CD-20-expressing cell is a malignant B cell in a subject with cancer, e.g., a CD20-positive leukemia, lymphoma, or myeloma. In certain aspects, the cancer is minimally responsive or non-responsive to rituximab therapy. In certain aspects, the subject is human.

The disclosure further provides a composition that includes the binding molecule as described above.

The disclosure further provides a polynucleotide including a nucleic acid sequence that encodes a polypeptide subunit of a multimeric binding molecule as provided herein. In certain aspects, the disclosure provides a polynucleotide that includes a nucleic acid sequence encoding a heavy chain polypeptide subunit of a multimeric binding molecule as provided herein, where the heavy chain polypeptide subunit includes an IgM heavy chain constant region or fragment thereof or an IgA heavy chain constant region or fragment thereof, and at least the antibody VH portion of the CD20 antigen binding domain. In certain aspects, the heavy chain polypeptide subunit can include a human IgM constant region or fragment thereof fused to the C-terminal end of a VH that includes (a) an HCDR1, HCDR2, HCDR3, where the HCDR1 includes the amino acid sequence of SEQ ID NO: 39 or SEQ ID NO: 39 with one or two single amino acid substitutions; the HCDR2 includes the amino acid sequence of SEQ ID NO: 40 or SEQ ID NO: 40 with one or two single amino acid substitutions; the HCDR3 includes the amino acid sequence of SEQ ID NO: 41, SEQ ID NO: 41 with one or two single amino acid substitutions; or (b) an amino acid sequence at least 80%, at least 85%, at least 90%, at least 95% or 100% identical to SEQ ID NO: 38. In certain aspects the provided polynucleotide can encode the amino acid sequence SEQ ID NO: 56. The disclosure further provides a polynucleotide composition that includes a polynucleotide as described.

The provided polynucleotide composition can further include, e.g., a nucleic acid sequence that encodes a light chain polypeptide subunit, where the light chain polypeptide subunit includes the antibody VL portion of the CD20 antigen binding domain. In certain aspects the light chain polypeptide subunit can include a human antibody light chain constant region or fragment thereof fused to the C-terminal end of a VL that includes: (a) an LCDR1, LCDR2, and LCDR3, where the LCDR1 includes the amino acid sequence of SEQ ID NO: 43, or SEQ ID NO: 43 with one or two single amino acid substitutions; the LCDR2 includes the amino acid sequence of SEQ ID NO: 44 or SEQ ID NO: 44 with one or two single amino acid substitutions; and the LCDR3 includes the amino acid sequence of SEQ ID NO: 45 or SEQ ID NO: 45 with one or two single amino acid substitutions; or (b) an amino acid sequence at least 80%, at least 85%, at least 90%, at least 95% or 100% identical to SEQ ID NO: 42. In certain aspects the nucleic acid sequence that encodes the light chain polypeptide subunit can encode the amino acid sequence SEQ ID NO: 58.

In certain aspects of the provided polynucleotide composition, the nucleic acid sequence encoding the heavy chain polypeptide subunit and the nucleic acid sequence encoding the light chain polypeptide subunit can be on separate vectors, or they can be situated on a single vector.

The provided polynucleotide composition can further include, e.g., a nucleic acid sequence that encodes a J-chain, or functional fragment thereof, or a functional variant thereof. In certain aspects the J-chain or fragment thereof can include the amino acid sequence SEQ ID NO: 49 or a functional fragment thereof. Moreover, the J-chain or fragment thereof can be a modified J-chain that further includes a heterologous polypeptide. The heterologous polypeptide can, in certain aspects, be directly or indirectly fused to the J-chain or fragment thereof. In certain aspects, the heterologous polypeptide can include an antibody or antigen-binding fragment thereof. In certain aspects, the heterologous polypeptide can be, e.g., a scFv that can specifically bind to CD3ε. In certain aspects the modified J-chain can include the amino acid sequence SEQ ID NO: 64 (V15J) or SEQ ID NO: 66 (J15V). In those aspects where the modified J-chain further comprises a signal peptide, the modified J-chain can include the amino acid sequence SEQ ID NO: 63 (V15J) or SEQ ID NO: 65 (J15V). In certain aspects of the provided polynucleotide composition, the nucleic acid sequence that encodes a J-chain, or functional fragment thereof, or a functional variant thereof can include SEQ ID NO: 68 or SEQ ID NO: 69.

In certain aspects of the provided polynucleotide composition, the nucleic acid sequence encoding the heavy chain polypeptide subunit, the nucleic acid sequence encoding the light chain polypeptide subunit, and the nucleic acid sequence encoding the J-chain can be situated on a single vector, or they can be situated on two or three separate vectors. The disclosure further provides the vector or vectors that singly or collectively contain the provided polynucleotide composition. The disclosure further provides a host cell including the provided polynucleotide, the provided polynucleotide composition, or the provided vector or vectors, where the host cell can express a multivalent anti-CD20 binding molecule as provided herein. The disclosure further provides a method of producing a multivalent anti-CD20 binding molecule as provided herein, where the method includes culturing the provided host cell, and recovering the binding molecule.

In certain aspects, the disclosure provides a method for directing complement-mediated, T-cell-mediated, or both complement-mediated and T-cell-mediated killing of a CD20-expressing cell where the method includes contacting a CD20-expressing cell with a multimeric binding molecule as provided herein or a composition that includes the provided binding molecule. According to these aspects, the binding molecule can direct complement-mediated, T-cell-mediated, or both complement-mediated and T-cell-mediated killing of a CD-20-expressing cell at higher potency than an equivalent amount of a monospecific, bivalent IgG1 antibody or fragment thereof that specifically binds to the same CD20 epitope as the CD20 antigen binding domain. In certain aspects, the monospecific, bivalent IgG1 antibody is 1.5.3, which includes a VH having the amino acid sequence SEQ ID NO: 38 and a VL having the amino acid sequence SEQ ID NO: 42. In certain aspects, the CD-20-expressing cell is a lymphoma cell line, e.g., a Ramos cell line, a Raji cell line, a Daudi cell line, a Namalwa cell line, a Granta cell line, a Z138 cell line, a DoHH2 cell line, or a DB cell line. In certain aspects, the CD20-expressing cell is a Raji cell line, and the binding molecule directs complement-mediated killing with an IC$_{50}$ at least four-fold, at least ten-fold, at least 50-fold, or at least 100-fold lower than the IC$_{50}$ of an equivalent amount of the monospecific bivalent IgG1 antibody, as measured, e.g., in μg/ml. In certain aspects, where the CD20-expressing cell is a Ramos cell line, the binding molecule can direct complement-mediated killing with an IC$_{50}$ at least ten-fold, at least 20-fold, at least 30-fold, at least 40-fold, at least 50-fold, at least 60-fold, at least 70-fold, at least 80-fold, at least 90-fold, or at least 100-fold lower than the IC$_{50}$ of an equivalent amount of the monospecific bivalent IgG1 antibody, as measured, e.g., as molar equivalents. In certain aspects, the CD-20-expressing cell is a malignant B cell in a subject with cancer, e.g., a CD20-positive leukemia, lymphoma, or myeloma. In certain aspects, the cancer is minimally responsive or non-responsive to rituximab therapy. In certain aspects the subject is a human.

In other aspects, the disclosure provides a method for directing complement-mediated, T-cell-mediated, or both complement-mediated and T-cell-mediated killing of a CD20-expressing cell, where the method includes contacting a CD20-expressing cell with a dimeric, pentameric, or hexameric binding molecule including two, five, or six bivalent binding units, respectively, where each binding unit includes two IgA or IgM heavy chain constant regions or fragments thereof and two antigen binding domains, where at least one antigen binding domain of the binding molecule is a CD20 antigen binding domain, and where the binding molecule can direct complement-mediated, T-cell-mediated, or both complement-mediated and T-cell-mediated killing of a CD-20-expressing cell at higher potency than an equivalent amount of a monospecific, bivalent IgG1 antibody or fragment thereof that specifically binds to the same CD20 epitope as the CD20 antigen binding domain.

According to these provided methods, the CD20 antigen binding domain can include six immunoglobulin complementarity determining regions HCDR1, HCDR2, HCDR3, LCDR1, LCDR2, and LCDR3, where the HCDR1 includes the amino acid sequence of SEQ ID NO: 2 or SEQ ID NO: 2 with one or two single amino acid substitutions; the HCDR2 includes the amino acid sequence of SEQ ID NO: 3 or SEQ ID NO: 3 with one, two, three, four, or five single amino acid substitutions; the HCDR3 includes the amino acid sequence of SEQ ID NO: 4, SEQ ID NO: 4 with one, two, or three single amino acid substitutions, SEQ ID NO: 10, or SEQ ID NO: 31, the LCDR1 includes the amino acid sequence of SEQ ID NO: 6, or SEQ ID NO: 6 with one, two, or three single amino acid substitutions; the LCDR2 includes the amino acid sequence of SEQ ID NO: 7 or SEQ ID NO: 7 with one or two single amino acid substitutions; and the LCDR3 includes the amino acid sequence of SEQ ID NO: 8 or SEQ ID NO: 8 with one or two single amino acid substitutions.

According to these provided methods, the CD20 antigen binding domain can include a VH and a VL including, respectively: (a) an amino acid sequence at least 80%, at least 85%, at least 90%, at least 95% or 100% identical to SEQ ID NO: 1 and an amino acid sequence at least 80%, at least 85%, at least 90%, at least 95% or 100% identical to SEQ ID NO: 5; (b) an amino acid sequence at least 80%, at least 85%, at least 90%, at least 95% or 100% identical to SEQ ID NO: 9 and an amino acid sequence at least 80%, at least 85%, at least 90%, at least 95% or 100% identical to SEQ ID NO: 11; (c) an amino acid sequence at least 80%, at least 85%, at least 90%, at least 95% or 100% identical to SEQ ID NO: 15 and an amino acid sequence at least 80%, at least 85%, at least 90%, at least 95% or 100% identical to SEQ ID NO: 18; (d) an amino acid sequence at least 80%, at least 85%, at least 90%, at least 95% or 100% identical to SEQ ID NO: 22 or SEQ ID NO: 23 and an amino acid sequence at least 80%, at least 85%, at least 90%, at least 95% or 100% identical to SEQ ID NO: 24, SEQ ID NO: 26, SEQ ID NO: 28, or SEQ ID NO: 29; (e) an amino acid sequence at least 80%, at least 85%, at least 90%, at least 95% or 100% identical to SEQ ID NO: 30 and an amino acid sequence at least 80%, at least 85%, at least 90%, at least 95% or 100% identical to SEQ ID NO: 32; or (f) an amino acid sequence at least 80%, at least 85%, at least 90%, at least 95% or 100% identical to SEQ ID NO: 35 and an amino acid sequence at least 80%, at least 85%, at least 90%, at least 95% or 100% identical to SEQ ID NO: 37.

According to these provided methods, the IgA heavy chain constant regions or fragments thereof of the binding molecule can each include a Cα2 domain or a Cα3-tp domain, and one or more IgA heavy chain constant regions or fragments thereof can further include a Cα1 domain. In certain aspects, the IgA heavy chain constant region is a human IgA constant region. In certain aspects a dimeric binding molecule according to these provided methods can further include a secretory component According to these provided methods, the IgM heavy chain constant regions or fragments thereof of the binding molecule each include a Cμ3 domain and a Cμ4-tp domain, and in certain aspects can further include a Cμ2 domain, a Cμ1 domain, or any combination thereof. In certain aspects the IgM heavy chain constant region is a human IgM constant region.

According to these provided methods, where the binding molecule is dimeric or pentameric, the binding molecule can further include a J-chain, or functional fragment thereof, or a functional variant thereof. In certain aspects, the J-chain or fragment thereof includes the amino acid sequence SEQ ID NO: 49 or a functional fragment thereof. In certain aspects, the J-chain or fragment thereof can further include a heterologous polypeptide. The heterologous polypeptide can be directly or indirectly fused to the J-chain or fragment thereof. In certain aspects the heterologous polypeptide can be indirectly fused to the J-chain or fragment thereof via a peptide linker. In certain aspects the peptide linker can include, e.g., at least 5 amino acids, but no more than 25 amino acids. In certain aspects the peptide linker consists of GGGGSGGGGSGGGGS (SEQ ID NO: 67). The heterologous polypeptide can be fused to or near the N-terminus of the J-chain or fragment thereof, the C-terminus of the J-chain or fragment thereof, or to both the N-terminus and C-terminus of the J-chain or fragment thereof. In certain aspects the heterologous polypeptide can include a binding domain, e.g., an antibody or antigen-binding fragment thereof. The antigen-binding fragment can be, for example, a Fab fragment, a Fab' fragment, an F(ab')$_2$ fragment, an Fd fragment, an Fv fragment, a single-chain Fv (scFv) fragment, a disulfide-linked Fv (sdFv) fragment, or any combination thereof. In certain aspects the heterologous polypeptide can specifically bind to CD3ε. For example, in certain aspects the modified J-chain can include the amino acid sequence SEQ ID NO: 64 (V15J) or SEQ ID NO: 66 (J15V). Moreover, in certain aspects, these particular modified J-chains can further include a signal peptide, where the modified J-chain then includes the amino acid sequence SEQ ID NO: 63 (V15J) or SEQ ID NO: 65 (J15V).

According to these provided methods, each binding unit of the binding molecule can include two IgA or IgM heavy chains each including a VH situated amino terminal to the IgA or IgM constant region or fragment thereof, and two immunoglobulin light chains each including a VL situated amino terminal to an immunoglobulin light chain constant region. In certain aspects, at least one binding unit of the binding molecule includes two identical CD20 antigen binding domains, and where the two IgA or IgM heavy chains within the at least one binding unit are identical. In some aspects, the two IgM heavy chains within at least one binding unit include the amino acid sequence SEQ ID NO: 52. In some aspects, the two light chain constant regions are human lambda constant regions or human kappa constant regions that can be identical and include the amino acid sequence SEQ ID NO: 54.

According to these provided methods, the binding molecule can include at least two, at least three, at least four, at least five, at least six, at least seven, at least eight, at least nine, at least ten, at least eleven, or at least twelve CD20 antigen binding domains that in certain aspects can be identical. According to these provided methods at least two, at least three, at least four, at least five, or at least six of the binding units within the binding molecule can be identical.

According to these provided methods, the reference monospecific, bivalent IgG1 antibody can be rituximab, which includes a VH having the amino acid sequence SEQ ID NO: 1 and a VL having the amino acid sequence SEQ ID NO: 5.

According to these provided methods, the CD-20-expressing cell can be a lymphoma cell line, e.g., a Ramos cell line, a Raji cell line, a Daudi cell line, a Namalwa cell line, a Granta cell line, a Z138 cell line, a DoHH2 cell line, or a DB cell line. In certain aspects where the cell line is a Granta cell line, the binding molecule can direct complement-mediated killing of the cell line at about six times the potency of rituximab. In certain aspects where the cell line is a Raji cell line or a Ramos cell line, and where the binding molecule can direct complement-mediated killing of the cell line at about three times the potency of rituximab.

According to these provided methods, the CD-20-expressing cell can be a malignant B cell in a subject with cancer, e.g., a CD20-positive leukemia, lymphoma, or myeloma. In certain aspects, the cancer is minimally responsive or non-responsive to rituximab therapy. In certain aspects, the subject is human.

BRIEF DESCRIPTION OF THE DRAWINGS/FIGURES

FIG. 1: The molecular diagram of CD20 molecule. CD20 is a tetraspanning-transmembrane protein that predominantly remains on the membrane of B cells without internalization upon antibody binding. The binding sites of CD20 monoclonal antibodies, rituximab and ofatumumab, are indicated. A linear diagram of CD20 is included to display the orientation of transmembrane (TM), extracellular domains (ECD) and cytoplasmic regions.

FIG. 2: Schematic diagrams of IgG, IgM hexamer and IgM pentamer. IgG is displayed as 150 kDa protein with heavy and light chains indicated. IgM including a J-chain is indicated as a pentamer of approximately 915 kDa. IgM without a J-chain is shown as a hexamer having a molecular weight of approximately 1080 kDa.

Figure 3:
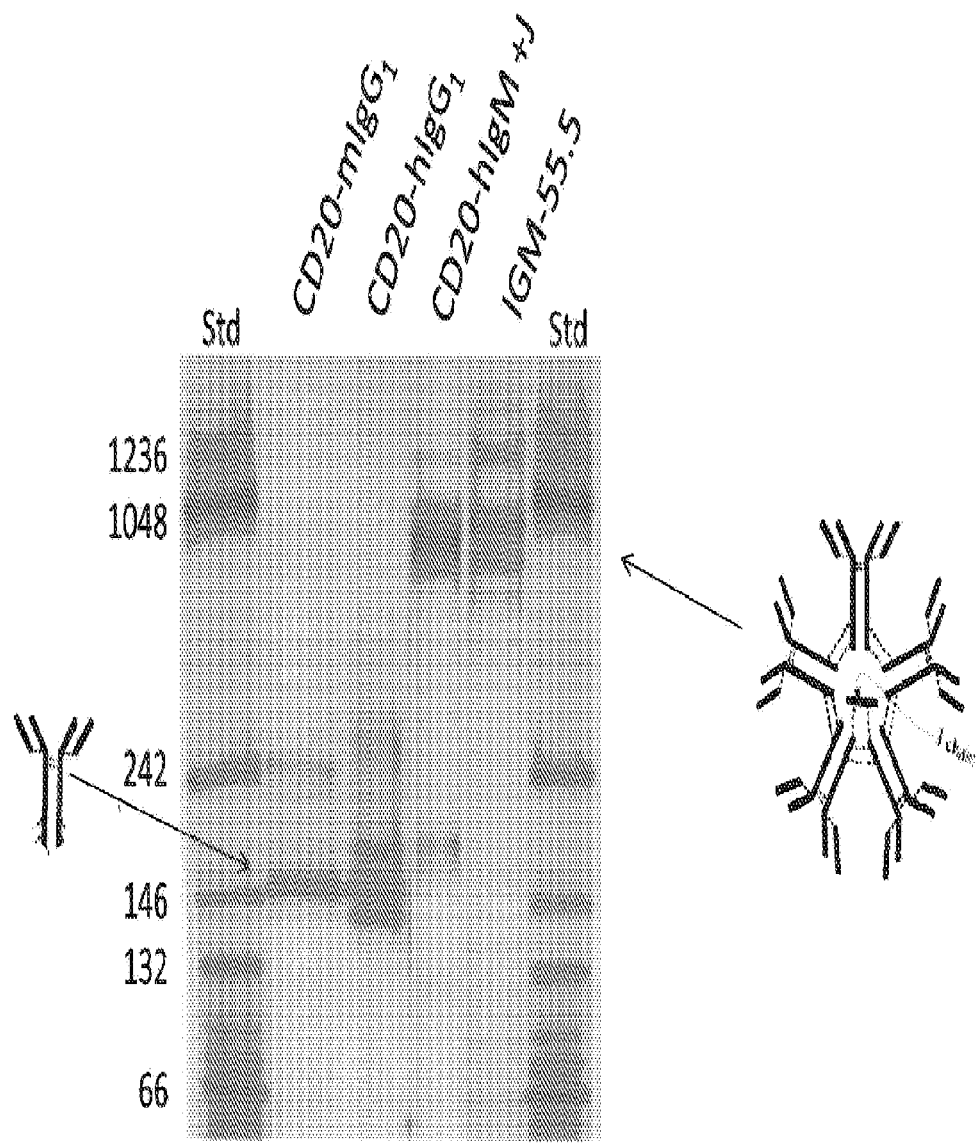

FIG. 3: Non-reducing SDS-PAGE of IgG and IgM. IgG and IgM CD20 antibodies based on rituximab run on non-reducing, SDS denatured polyacrylamide gel electrophoresis. The first and last lanes are molecular weight standards. The murine and human IgG1 antibodies (second and third lanes, respectively) exhibit molecular weights of approximately 150 kDa. The IgM+J-chain version (a commercially available CD20 IgM antibody available from Invivogen) exhibits a molecular weight of about 1050 kDa (fourth lane). The anti-CDIM antibody IGM-55.5 (see PCT Publication No. WO 2013/120012) (fifth lane) is included as another IgM for comparison.

Figure 4:
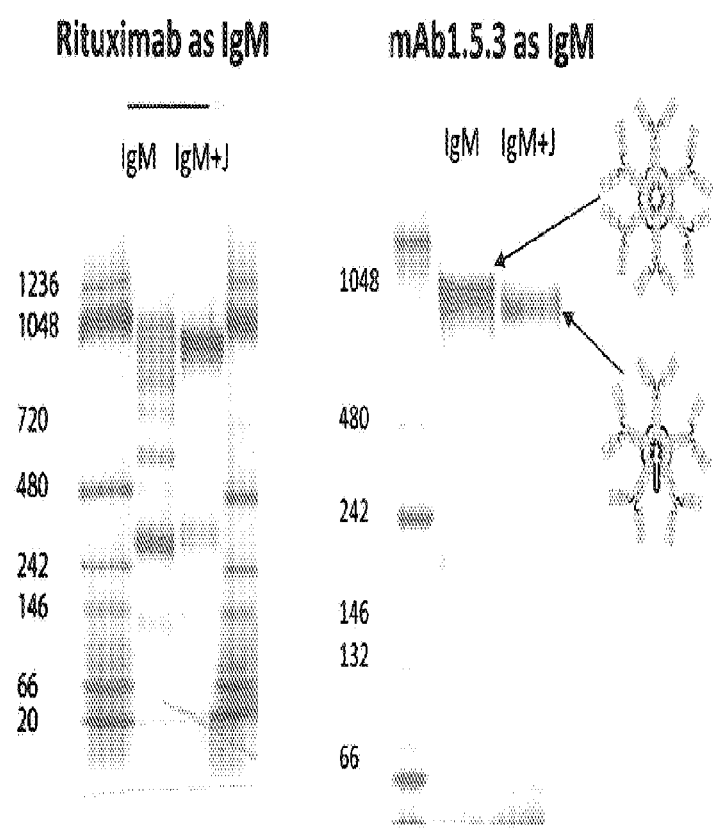
Figure 5:
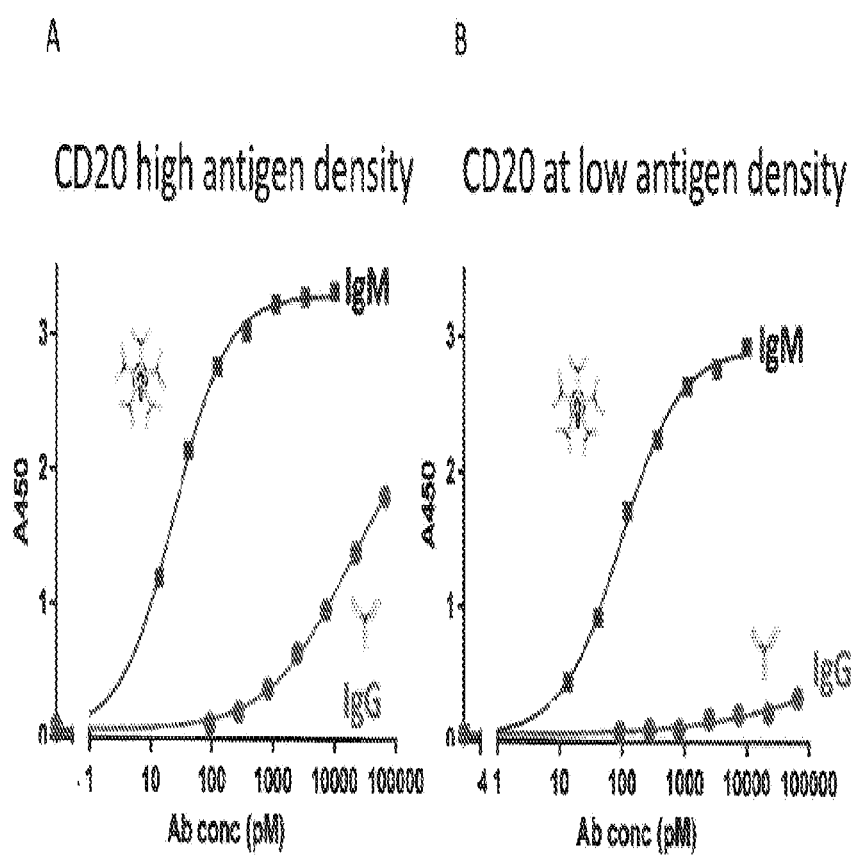

FIG. 4: Assembly of Anti-CD20 IgM Oligomers. Non-reducing SDS-PAGE shows that anti-CD20 antibodies comprising the variable domains of rituximab and 1.5.3 can assemble as IgM. The rituximab IgM is shown in the first panel without J-chain (lane 2), and with J-chain (lane 3). The 1.5.3 IgM is shown in the second panel without J-chain (lane 2) and with J-chain (lane 3).

FIG. 5A: ELISA results showing binding of 1.5.3 IgM and 1.5.3 IgG to CD20 at high antigen density (10 µg/ml).

FIG. 5B: ELISA results showing binding of 1.5.3 IgM and 1.5.3 IgG to CD20 at low antigen density (0.3 µg/ml).

FIG. 6A-E Anti-CD20 IgM is more potent than anti-CD20 IgG at complement dependent cytotoxicity. Human cultured leukemia or lymphoma cells were incubated with commercially-available anti-CD20 IgM or IgG plus 10% human complement. Cell viability was measured after 4 hours using a metabolic indicator dye (CCK8). In most of the lymphoma cell lines (Granta (FIG. 6A), Raji (FIG. 6B), and Ramos (FIG. 6C)), the IgM isotype of anti-CD20 was more potent than the corresponding IgG isotype, in the presence of complement. For comparison, the assay was also carried out in Namalwa cells (FIG. 6E), which exhibit minimal expression of CD20, and Nalm-6 cells (FIG. 6D), which are devoid of CD20 expression.

Figure 7:
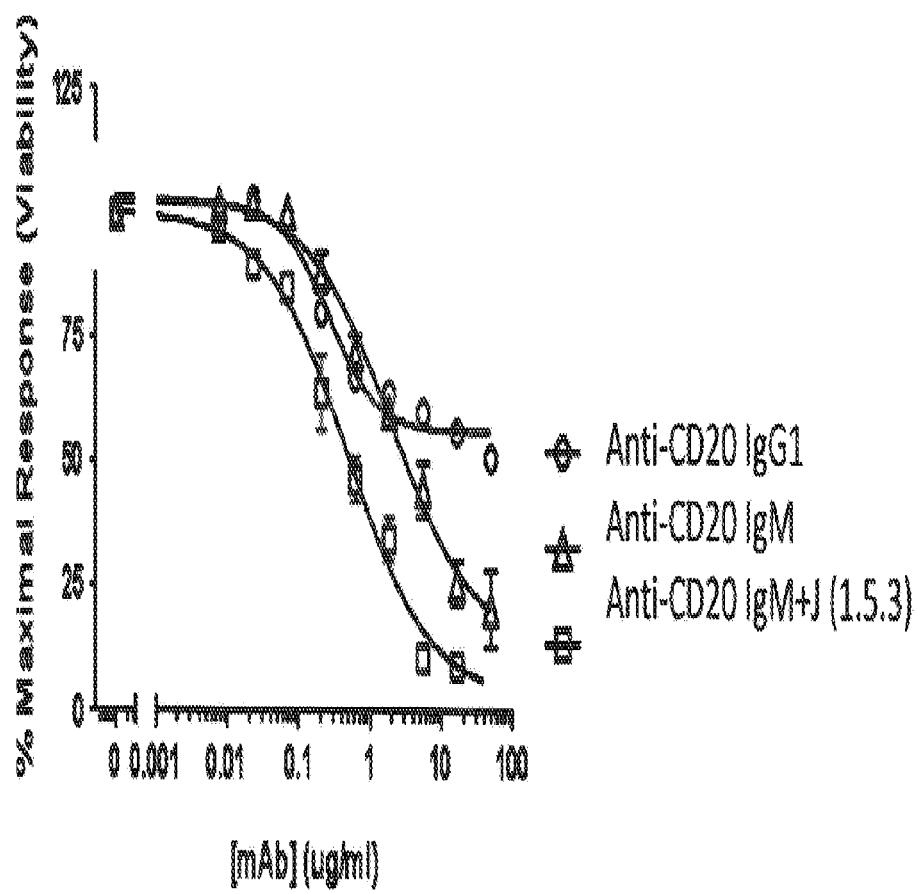

FIG. 7: Anti-CD20 IgM is more potent than rituximab at complement dependent cytotoxicity in the Raji cell line as measured on a µg/ml basis.

Figure 8A:
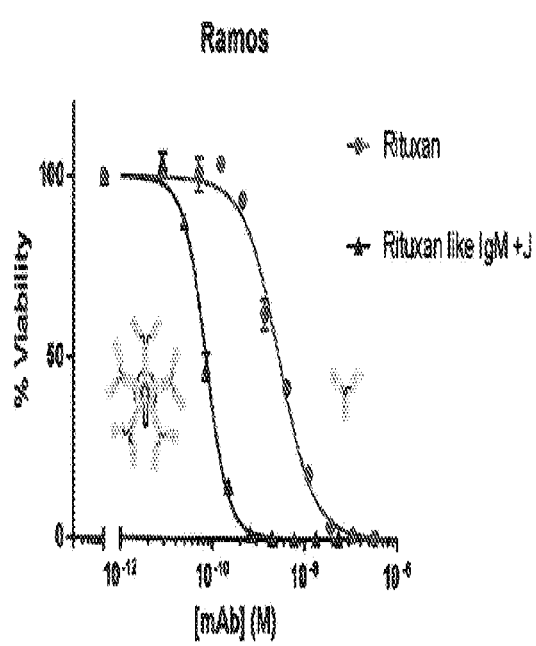
Figure 8B:
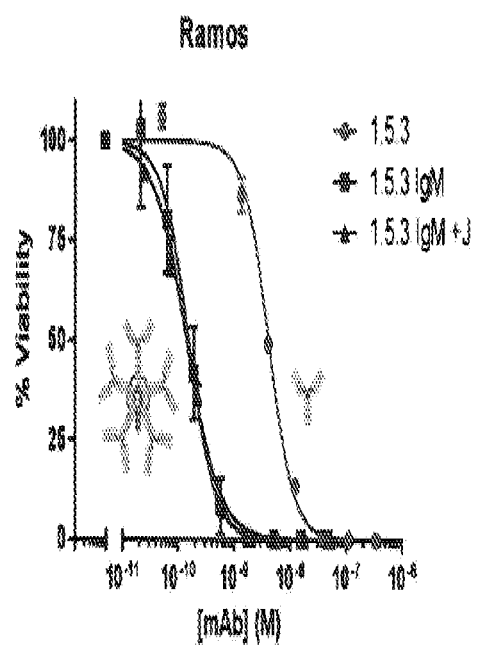

FIG. 8A-B: Anti-CD20 IgM is more effective than rituximab and 1.5.3 IgG at complement dependent cytotoxicity. Ramos cells were incubated with increasing concentrations of anti-CD20 IgM or IgG and 10% human complement. Cell viability was measured after 4 hours. FIG. 8A compares rituximab (IgG) and a rituximab-like IgM+J-chain. FIG. 8B compares 1.5.3 (IgG), 1.5.3 IgM, and 1.5.3 IgM+J-chain. The tables in each panel show EC50 results in molar concentrations.

Figure 9:
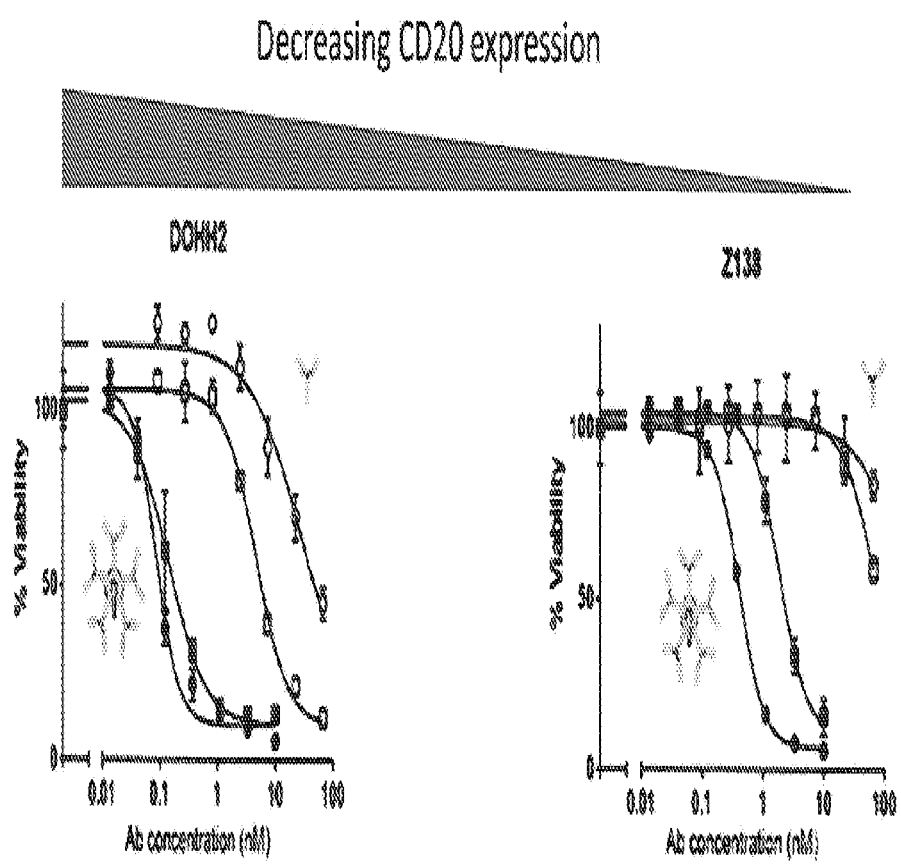

FIG. 9: Complement-dependent cytotoxicity (CDC) activity of rituximab IgG1 (open circles), rituximab-derived anti-human CD20 IgM+J (closed circles), 1.5.3 IgG1 (open squares), and 1.5.3 anti-CD20 IgM+J (closed squares) on DOHH2 and Z138 cells.

FIG. 10: Characterization of 1.5.3 IgM antibodies by gel electrophoresis and western blotting. Lane Key: 1: Marker; 2: 1.5.3 IgM+V15J; 3: 1.5.3 IgM+wtJ; 4: 1.5.3 IgM (hexamer); 5: Marker. FIG. 10A shows the hexamer and pentamer forms on a hybrid gel. FIG. 10B shows the antibodies resolved by non-reducing SDS-PAGE. FIG. 10C shows the antibodies resolved by reducing SDS-PAGE. The gel in FIG. 10C was transferred to a membrane and J-chain was detected by western blotting, shown in FIG. 10D.

Figure 11:
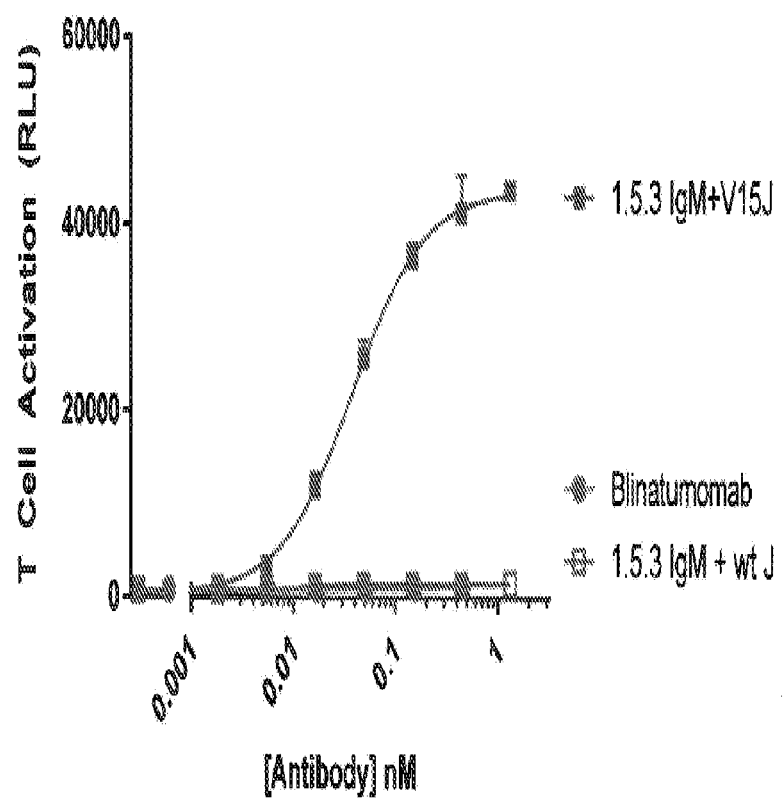

FIG. 11: 1.5.3 IgM+V15J (closed squares) elicits T-cell activation in a coculture of CD20+ RPMI8226 cells and engineered Jurkat T-cells to a greater extent than blinatumomab (closed circles) or 1.5.3 IgM+wt J (open squares).

Figure 12:
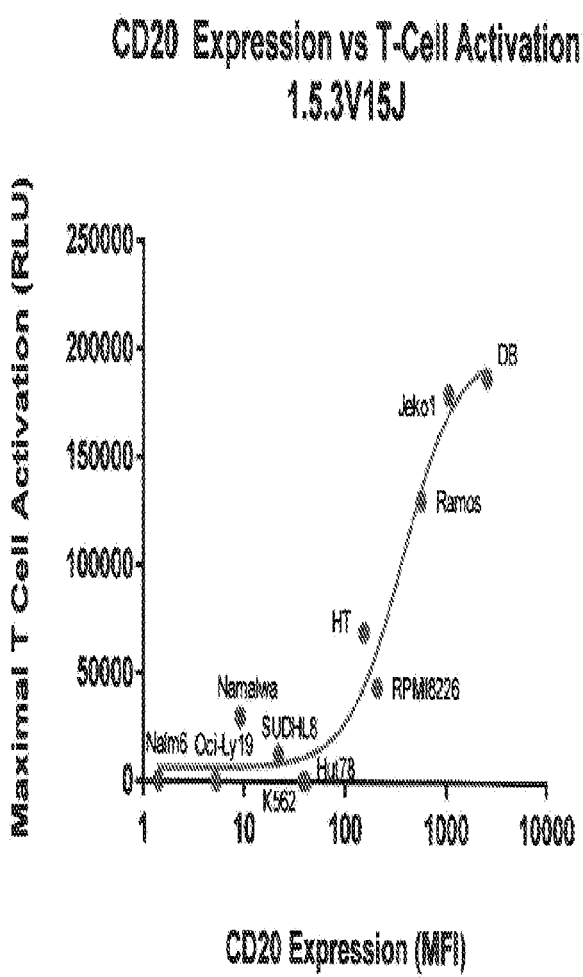

FIG. 12: T-cell activation by 1.5.3 IgM V15J as a function of CD20 expression using a series of tumor cell lines each expressing a different level of CD20 antigen (expressed as mean fluorescence intensity or MFI).

Figure 13:
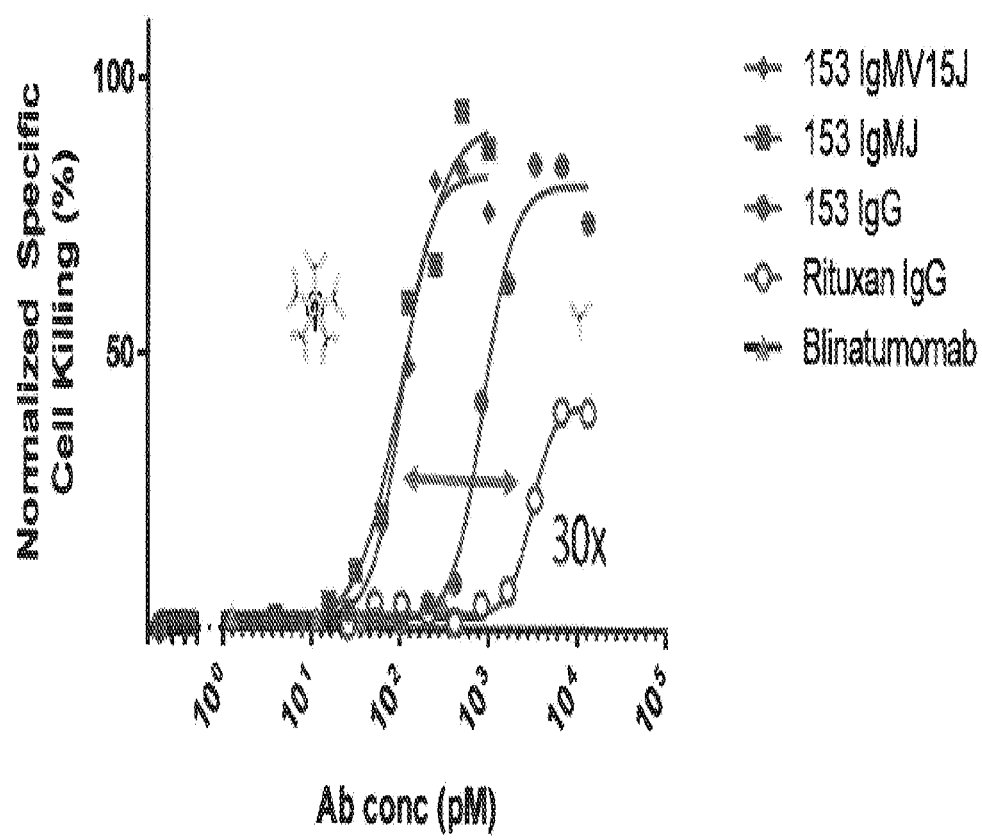

FIG. 13: Tumor cell killing in human blood using the KILR™ detection assay. Key: diamonds: 1.5.3 IgM+V15J; squares: 1.5.3 IgM+wild type J; closed circles: 1.5.3 IgG; open circles Rituxan IgG; triangles: blinatumomab.

FIG. 14A-B: T-cell directed B-cell killing in vivo in NSG mice engrafted with CD34+ cells to generate a human hematopoietic system. The mice were dosed with monospecific or bispecific 1.5.3 IgM and the number of human B-cells measured before and at 6 hours post dosing. FIG. 14A shows the results for the monospecific antibody with wild-type J-chain, and FIG. 14B shows the results for the bispecific with the V15J anti-CD3 J-chain.

Figure 15:
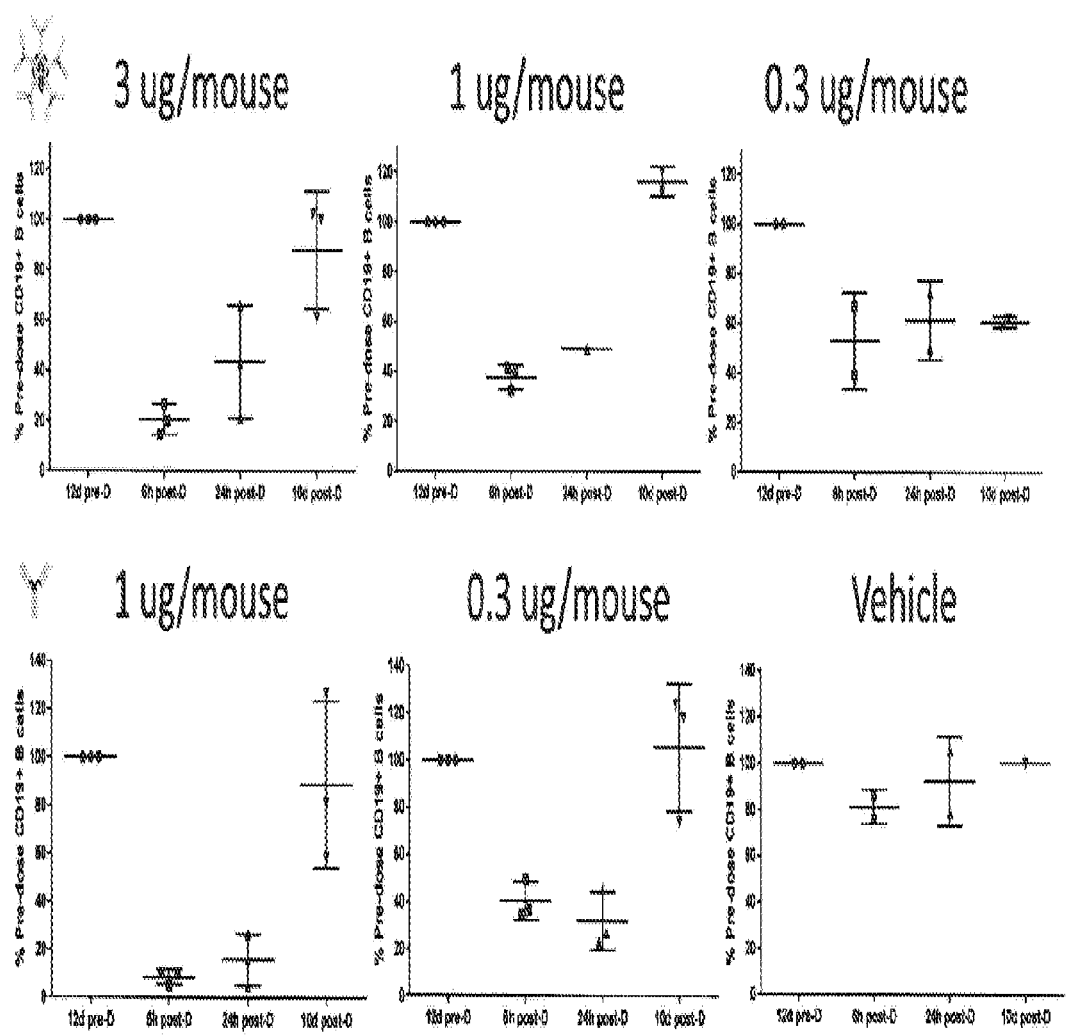

FIG. 15: Comparison of B-cell killing and recovery (at 10-days post dose) between 1.5.3+V15J (top row) and rituximab (bottom row).

DETAILED DESCRIPTION

Definitions

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

As used herein, the term "a non-naturally occurring polypeptide" or any grammatical variants thereof, is a conditional definition that explicitly excludes, but only excludes, those forms of the polypeptide that are, or could be, determined or interpreted by a judge or an administrative or judicial body, to be "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides which retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plural nucleic acids and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, the term "a non-naturally occurring polynucleotide" or any grammatical variants thereof, is a conditional definition that explicitly excludes, but only excludes, those forms of the nucleic acid or polynucleotide that are, or could be, determined or interpreted by a judge, or an administrative or judicial body, to be "naturally-occurring."

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

As used herein, the term "CD20" refers to a membrane protein expressed on the surface of B lymphocytes. The CD20 protein is referred to in the literature by other names, e.g., B-lymphocyte antigen CD20, B-lymphocyte cell-surface antigen B1, Bp35, CVID5, LEU-16, Membrane-spanning 4-domains subfamily A member 1, or MS4A2. The amino acid sequence for human CD20 (GenBank Accession No. NP_690605.1) is disclosed herein as SEQ ID NO: 50 (Table 2).

Disclosed herein are certain binding molecules, or antigen-binding fragments, variants, or derivatives thereof. Unless specifically referring to full-sized antibodies, the term "binding molecule" encompasses full-sized antibodies as well as antigen-binding subunits, fragments, variants, analogs, or derivatives of such antibodies, e.g., engineered antibody molecules or fragments that bind antigen in a manner similar to antibody molecules, but which use a different scaffold.

As used herein, the term "binding molecule" refers in its broadest sense to a molecule that specifically binds to a target or molecular determinant, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

As used herein, the terms "binding domain" or "antigen binding domain" refer to a region of a binding molecule that is sufficient to specifically bind to an epitope. For example, an "Fv," e.g., a variable heavy chain and variable light chain of an antibody, either as two separate polypeptide subunits or as a single chain, is considered to be a "binding domain." Other antigen binding domains include, without limitation, the variable heavy chain (VHH) of an antibody derived from a camelid species, or six immunoglobulin complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable domain of a heavy chain (for camelid species) or at least the variable domains of a heavy chain and a light chain. Basic immunoglobulin structures in vertebrate systems are relatively well understood. (See, e.g., Harlow et al., Antibodies: A Laboratory Manual, Cold Spring Harbor Laboratory Press, 2nd ed. 1988). Unless otherwise stated, the term "antibody" encompasses anything ranging from a small antigen-binding fragment of an antibody to a full sized antibody, e.g., an IgG antibody that includes two complete heavy chains and two complete light chains, an IgA antibody that includes four complete heavy chains and four complete light chains and can include a J-chain and/or a secretory component, or an IgM antibody that includes ten or twelve complete heavy chains and ten or twelve complete light chains and can include a J-chain.

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "isotype" of the antibody as IgG, IgM, IgA IgG, or IgE, respectively. The immunoglobulin subclasses (subtypes) e.g., $IgG_1$, $IgG_2$, $IgG_3$, $IgG_4$, $IgA_1$, $IgA_2$, are well characterized and are known to confer functional specialization. Modified versions of each of these immunoglobulins are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are expressed, e.g., by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure, or a "binding unit."

The term "binding unit" is used herein to refer to the portion of a binding molecule, e.g., an antibody or antigen-binding fragment thereof, which corresponds to a standard immunoglobulin structure, e.g., two heavy chains or fragments thereof and two light chains or fragments thereof, or two heavy chains or fragments thereof derived, e.g., from a camelid or condricthoid antibody. In certain aspects, e.g., where the binding molecule is a bivalent IgG antibody or antigen-binding fragment thereof, the terms "binding molecule" and "binding unit" are equivalent. In other aspects, e.g., where the binding molecule is an IgA dimer, an IgM pentamer, or an IgM hexamer, the binding molecule comprises two or more "binding units." Two in the case of an IgA dimer, or five or six in the case of an IgM pentamer or hexamer, respectively. A binding unit need not include full-length antibody heavy and light chains, but will typically be bivalent, i.e., will include two "antigen binding domains," as defined below. Certain binding molecules provided in this disclosure are dimeric, pentameric, or hexameric, and include two, five, or six bivalent binding units that include IgA or IgM constant regions or fragments thereof. As used herein, a binding molecule comprising two or more binding units, e.g., two, five, or six binding units, can be referred to as "multimeric."

The term "native sequence J-chain" or "native J-chain" as used herein refers to J-chain of native sequence IgM or IgA antibodies of any animal species, including mature human J-chain, the amino acid sequence of which is presented as SEQ ID NO: 49.

The term "modified J-chain" is used herein to refer to variants of native sequence J-chain polypeptides comprising a heterologous moiety, e.g., a heterologous polypeptide, e.g., an extraneous binding domain introduced into the native sequence. The introduction can be achieved by any means, including direct or indirect fusion of the heterologous polypeptide or other moiety or by attachment through a peptide or chemical linker. The term "modified human J-chain" encompasses, without limitation, a native sequence human J-chain of the amino acid sequence of SEQ ID NO: 49 or functional fragment thereof modified by the introduction of a heterologous moiety, e.g., a heterologous polypeptide, e.g., an extraneous binding domain. In certain aspects the heterologous moiety does not interfere with efficient polymerization of IgM into a pentamer or IgA into a dimer and binding of such polymers to a target. Exemplary modified J-chains can be found, e.g., in PCT Publication No. WO 2015/153912, which is incorporated herein by reference in its entirety.

The terms "valency," "bivalent," "multivalent" and grammatical equivalents, refer to the number of antigen binding domains in given binding molecule or binding unit. As such, the terms "bivalent", "tetravalent", and "hexavalent" in reference to a given binding molecule, e.g., an IgM antibody or fragment thereof, denote the presence of two antigen binding domains, four antigen binding domains, and six antigen binding domains, respectively. In a typical IgM-derived binding molecule where each binding unit is bivalent, the binding molecule itself can have 10 or 12 valencies. In a typical IgA-derived binding molecule where each binding unit is bivalent, the binding molecule itself can have 4 valencies. A bivalent or multivalent binding molecule can be monospecific, i.e., all of the antigen binding domains are the same, or can be bispecific or multispecific, e.g., where two or more antigen binding domains are different, e.g., bind to different epitopes on the same antigen, or bind to entirely different antigens.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three-dimensional structural characteristics, and or specific charge characteristics. An epitope is a region of a target that is bound by an antibody.

"Multispecific binding molecules or antibodies" or "bispecific binding molecules or antibodies" refer to binding molecules, antibodies, or antigen-binding fragments thereof that have the ability to specifically bind to two or more different epitopes on the same or different target(s). "Monospecific" refers to the ability to bind only one epitope.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (e.g., CH1, CH2, CH3, or CH4) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

A "full length IgM antibody heavy chain" is a polypeptide that includes, in N-terminal to C-terminal direction, an antibody heavy chain variable domain ($V_H$), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4) that can include a tailpiece.

A "full length IgA antibody heavy chain" is a polypeptide that includes, in N-terminal to C-terminal direction, an antibody heavy chain variable domain ($V_H$), an antibody constant heavy chain constant domain 1 (CA1 or Cα1), an antibody heavy chain constant domain 2 (CA2 or Cα2), an antibody heavy chain constant domain 3 (CA3 or Cα3) that can include a tailpiece. The structure of monomeric and secretory IgA is described, e.g., in Woof, J M and Russell, M W, *Mucosal Immunology* 4:590-597 (2011).

As indicated above, a variable region (i.e., the "antigen binding domain") allows a binding molecule to selectively recognize and specifically bind epitopes on antigens. That is, the VL domain and VH domain (or just a VH domain for camelid or condricthoid antibodies (designated as VHH)), or subset of the complementarity determining regions (CDRs), of a binding molecule, e.g., an antibody, can combine to form the antigen binding domain. More specifically, an antigen binding domain can be defined by three CDRs on each of the VH and VL chains (or 3 CDRs on a VHH). Certain antibodies form larger structures. For example, IgA can form a molecule that includes two H2L2 binding units, a J-chain, and a secretory component, covalently connected via disulfide bonds; and IgM can form a dimeric, pentameric, or hexameric molecule that includes two, five, or six H2L2 binding units and optionally a J-chain covalently connected via disulfide bonds.

The six "complementarity determining regions" or "CDRs" present in an antibody antigen binding domain are short, non-contiguous sequences of amino acids that are specifically positioned to form the antigen binding domain as the antibody assumes its three-dimensional configuration in an aqueous environment. The remainder of the amino acids in the antigen binding domain, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids which encompass the CDRs as defined by each of the above cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions*

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Immunoglobulin variable domains can also be analyzed, e.g., using the IMGT information system (www://imgt.cines.fr/) (IMGT®/V-Quest) to identify variable region segments, including CDRs. See, e.g., Brochet, X. et al., *Nucl. Acids Res.* 36:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for amino acid sequences in this disclosure.

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5 \times 10^{-2}$ sec$^{-1}$, $10^{-2}$ sec$^{-1}$, $5 \times 10^{-3}$ sec$^{-1}$, $10^{-3}$ sec$^{-1}$, $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein can be said to bind a target antigen with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$, $5 \times 10^4$ M$^{-1}$ sec$^{-1}$, $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross-reactive epitope generally contains many of the same complementary structural features as the inducing epitope, and in some cases, can actually fit better than the original.

A binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, $10^{-3}$M, $5\times10^{-4}$ M, $10^{-4}$ M, $5\times10^{-5}$M, $10^{-5}$M, $5\times10^{-6}$ M, $10^{-6}$ M, $5\times10^{-7}$ M, $10^{-7}$ M, $5\times10^{-8}$M, $10^{-8}$M, $5\times10^{-9}$M, $10^{-9}$M, $5\times10^{-10}$ M, $10^{-10}$ M, $5\times10^{-11}$M, $10^{-11}$M, $5\times10^{-12}$ M, $10^{-12}$ M, $5\times10^{-13}$M, $10^{-13}$M, $5\times10^{-14}$M, $10^{-14}$ M, $5\times10^{-15}$M, or $10^{-15}$ M.

Antibody fragments including single-chain antibodies or other antigen binding domains can exist alone or in combination with one or more of the following: hinge region, CH1, CH2, CH3, or CH4 domains, J-chain, or secretory component. Also included are antigen-binding fragments that can include any combination of variable region(s) with one or more of a hinge region, CH1, CH2, CH3, or CH4 domains, a J-chain, or a secretory component. Binding molecules, e.g., antibodies, or antigen-binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and can in some instances express endogenous immunoglobulins and some not, as described infra and, for example in, U.S. Pat. No. 5,939,598 by Kucherlapati et al.

As used herein, the term "heavy chain subunit" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof. For example, a binding molecule, e.g., an antibody or fragment, variant, or derivative thereof can include, without limitation, in addition to a VH domain: a CH1 domain; a CH1 domain, a hinge, and a CH2 domain; a CH1 domain and a CH3 domain; a CH1 domain, a hinge, and a CH3 domain; or a CH1 domain, a hinge domain, a CH2 domain, and a CH3 domain. In certain aspects a binding molecule, e.g., an antibody or fragment, variant, or derivative thereof can include, in addition to a VH domain, a CH3 domain and a CH4 domain; or a CH3 domain, a CH4 domain, and a J-chain. Further, a binding molecule for use in the disclosure can lack certain constant region portions, e.g., all or part of a CH2 domain. It will be understood by one of ordinary skill in the art that these domains (e.g., the heavy chain subunit) can be modified such that they vary in amino acid sequence from the original immunoglobulin molecule.

As used herein, the term "light chain subunit" includes amino acid sequences derived from an immunoglobulin light chain. The light chain subunit includes at least a VL, and can further include a CL (e.g., Cκ or Cλ) domain.

Binding molecules, e.g., antibodies or antigen-binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As used herein the term "disulfide bond" includes the covalent bond formed between two sulfur atoms. The amino acid cysteine comprises a thiol group that can form a disulfide bond or bridge with a second thiol group.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "multispecific antibody, e.g., "bispecific antibody" refers to an antibody that has antigen binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Ströhlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an immunoglobulin variable region can be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide. A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain. For example, in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into RNA, e.g., messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of a binding molecule such as an antibody, comprising one or more antigen binding domains. Such binding molecules, e.g., antibodies, can be used, e.g., for diagnostic procedures and/or for treatment or prevention of a disease.

IgM Binding Molecules

IgM is the first immunoglobulin produced by B cells in response to stimulation by antigen and is present at around 1.5 mg/ml in serum with a half-life of 5 days. IgM is a dimeric, pentameric, or hexameric molecule. An IgM binding unit includes two light and two heavy chains. While IgG contains three heavy chain constant domains (CH1, CH2 and CH3), the heavy (0 chain of IgM additionally contains a fourth constant domain (CH4), that includes a C-terminal "tailpiece." The human IgM constant region typically comprises the amino acid sequence SEQ ID NO: 47. The human Cμ1 region ranges from about amino acid 5 to about amino acid 102 of SEQ ID NO: 47; the human Cμ2 region ranges from about amino acid 114 to about amino acid 205 of SEQ ID NO: 47, the human Cμ3 region ranges from about amino acid 224 to about amino acid 319 of SEQ ID NO: 47, the Cμ4 region ranges from about amino acid 329 to about amino acid 430 of SEQ ID NO: 47, and the tailpiece ranges from about amino acid 431 to about amino acid 453 of SEQ ID NO: 47 (Table 2).

Five IgM binding units can form a complex with an additional small polypeptide chain (the J-chain) to form an IgM antibody. The human J-chain comprises the amino acid sequence SEQ ID NO: 49 (Table 2). A typical IgM pentamer is depicted in FIG. 2. Without the J-chain, IgM binding units typically assemble into a hexamer. A typical IgM hexamer is depicted in FIG. 2. While not wishing to be bound by theory, the assembly of IgM binding units into a hexameric or pentameric binding molecule is thought to involve the Cμ3 and Cμ4 domains. Accordingly, a hexameric or pentameric binding molecule provided in this disclosure typically includes IgM constant regions that include at least the Cμ3 and Cμ4 domains. A comparison of IgG antibodies and IgM antibodies by non-reducing polyacrylamide gel electrophoresis is shown in FIG. 3.

An IgM heavy chain constant region can additionally include a Cμ2 domain or a fragment thereof, a Cμ1 domain or a fragment thereof, and/or other IgM heavy chain domains. In certain aspects, a binding molecule as provided herein can include a complete IgM heavy (μ) chain constant domain (e.g., SEQ ID NO: 47), or a variant, derivative, or analog thereof.

Pentameric or Hexameric CD20 Binding Molecules

This disclosure provides a hexameric or pentameric binding molecule, i.e., a binding molecule with five or six "binding units" as defined herein, that can specifically bind to CD20, e.g., human CD20. A binding molecule as provided herein can possess improved binding characteristics or biological activity as compared to a binding molecule composed of a single binding unit, e.g., a bivalent IgG antibody. In certain aspects, the disclosure provides a pentameric or hexameric binding molecule comprising five or six bivalent binding units, respectively, where each binding unit includes two IgM heavy chain constant regions or fragments thereof. In certain aspects, the two IgM heavy chain constant regions are human heavy chain constant regions.

Where the binding molecule provided herein is pentameric, the binding molecule can further comprise a J-chain, or functional fragment thereof, or variant thereof. In certain aspects, the J-chain is a modified J-chain comprising a heterologous moiety or one or more heterologous moieties, e.g., a heterologous polypeptide sequence, e.g., an extraneous binding domain introduced into the native sequence. In certain aspects the extraneous binding domain specifically binds to CD3, e.g., CD3ε. In certain aspects the modified J-chain comprises V15J (SEQ ID NO: 64) or J15V (SEQ ID NO: 66).

An IgM heavy chain constant region can include one or more of a Cµ1 domain, a Cµ2 domain, a Cµ3 domain, and/or a Cµ4 domain, provided that the constant region can serve a desired function in the binding molecule, e.g., associate with second IgM constant region to form an antigen binding domain, or associate with other binding units to form a hexamer or a pentamer. In certain aspects the two IgM heavy chain constant regions or fragments thereof within an individual binding unit each comprise a Cµ3 domain or fragment thereof, a Cµ4 domain or fragment thereof, a tailpiece (TP) or fragment thereof, or any combination of a Cµ3 domain a Cµ domain, and a TP or fragment thereof. In certain aspects the two IgM heavy chain constant regions or fragments thereof within an individual binding unit each further comprise a Cµ2 domain or fragment thereof, a Cµ1 domain or fragment thereof, or a Cµ1 domain or fragment thereof and a Cµ2 domain or fragment thereof.

In certain aspects each of the two IgM heavy chain constant regions in a given binding unit is associated with an antigen binding domain, for example an Fv portion of an antibody, e.g., a VH and a VL of a human or murine antibody. In a binding molecule as provided herein at least one antigen binding domain of the binding molecule is an anti-CD20 antigen binding domain, i.e., an antigen binding domain that can specifically bind to CD20, e.g., human CD20.

IgA Binding Molecules

IgA plays a role in mucosal immunity and comprises about 15% of total immunoglobulin produced. IgA is a monomeric or dimeric molecule. An IgA binding unit typically includes two light and two heavy chains. IgA contains three heavy chain constant domains (Cα1, Cα2 and Cα3), and includes a C-terminal "tailpiece." Human IgA has two subtypes, IgA1 and IgA2. The human IgA1 constant region typically comprises the amino acid sequence SEQ ID NO: 59. The human Cα1 region ranges from about amino acid 6 to about amino acid 98 of SEQ ID NO: 59; the human Cα2 region ranges from about amino acid 125 to about amino acid 220 of SEQ ID NO: 59, the human Cα3 region ranges from about amino acid 228 to about amino acid 330 of SEQ ID NO: 59, and the tailpiece ranges from about amino acid 331 to about amino acid 352 of SEQ ID NO: 59 (Table 2). The human IgA2 constant region typically comprises the amino acid sequence SEQ ID NO: 60. The human Cα1 region ranges from about amino acid 6 to about amino acid 98 of SEQ ID NO: 60 (Table 2); the human Cα2 region ranges from about amino acid 112 to about amino acid 207 of SEQ ID NO: 60, the human Cα3 region ranges from about amino acid 215 to about amino acid 317 of SEQ ID NO: 60, and the tailpiece ranges from about amino acid 318 to about amino acid 340 of SEQ ID NO: 60.

Two IgA binding units can form a complex with two additional polypeptide chains, the J-chain (SEQ ID NO: 49) and the secretory component (SEQ ID NO: 62) to form a secretory IgA (sIgA) antibody. While not wishing to be bound by theory, the assembly of IgA binding units into a dimeric sIgA binding molecule is thought to involve the Cα3 and tailpiece domains. Accordingly, a dimeric sIgA binding molecule provided in this disclosure typically includes IgA constant regions that include at least the Cα3 and tailpiece domains.

An IgA heavy chain constant region can additionally include a Cα2 domain or a fragment thereof, a Cα1 domain or a fragment thereof, and/or other IgA heavy chain domains. In certain aspects, a binding molecule as provided herein can include a complete IgA heavy (α) chain constant domain (e.g., SEQ ID NO: 59 or SEQ ID NO: 60), or a variant, derivative, or analog thereof.

Dimeric CD20 Binding Molecules

This disclosure provides a dimeric binding molecule, e.g., a binding molecule with two IgA "binding units" as defined herein, which can specifically bind to CD20, e.g., human CD20. A dimeric binding molecule as provided herein can possess improved binding characteristics or biological activity as compared to a binding molecule composed of a single binding unit, e.g., a bivalent IgG antibody. For example, an IgA binding molecule can reach mucosal sites providing greater tissue distribution for the binding molecules provided herein. In certain aspects, the disclosure provides a dimeric binding molecule comprising two bivalent binding units, where each binding unit includes two IgA heavy chain constant regions or fragments thereof. In certain aspects, the two IgA heavy chain constant regions are human heavy chain constant regions.

A dimeric IgA binding molecule as provided herein can further comprise a J-chain, or fragment thereof, or variant thereof. A dimeric IgA binding molecule as provided herein can further comprise a secretory component, or fragment thereof, or variant thereof. In certain aspects, the J-chain is a modified J-chain comprising a heterologous moiety or one or more heterologous moieties, e.g., a heterologous polypeptide, e.g., an extraneous binding domain introduced into the native sequence. In certain aspects the extraneous binding domain specifically binds to CD3, e.g., CD3ε. In certain aspects the modified J-chain comprises V15J (SEQ ID NO: 64) or J15V (SEQ ID NO: 66).

An IgA heavy chain constant region can include one or more of a Cα1 domain, a Cα2 domain, and/or a Cα3 domain, provided that the constant region can serve a desired function in the binding molecule, e.g., associate with a light chain constant region to facilitate formation of an antigen binding domain, or associate with another IgA binding unit to form a dimeric binding molecule. In certain aspects the two IgA heavy chain constant regions or fragments thereof within an individual binding unit each comprise a Cα3 domain or fragment thereof, a tailpiece (TP) or fragment thereof, or any combination of a Cα3 domain, a TP, or fragment thereof. In certain aspects the two IgA heavy chain constant regions or fragments thereof within an individual binding unit each further comprise a Cα2 domain or fragment thereof, a Cα1 domain or fragment thereof, or a Cα1 domain or fragment thereof and a Cα2 domain or fragment thereof.

In certain aspects each of the two IgA heavy chain constant regions in a given antigen binding domain is associated with an antigen binding domain, for example an Fv portion of an antibody, e.g., a VH and a VL of a human or murine antibody. In a binding molecule as provided herein at least one antigen binding domain of the binding molecule can be a CD20 antigen binding domain, e.g., a human CD20 antigen binding domain.

Modified J-Chains

In certain aspects CD20 binding molecules provided herein can be bispecific, incorporating a modified J-chain. As provided herein and in PCT Publication No. WO 2015/153912, a modified J-chain can comprise a heterologous moiety, e.g., a heterologous polypeptide, e.g., an extraneous binding domain, which can include, for example, a polypeptide binding domain capable of specifically binding to a target. The binding domain can be, for example, an antibody or antigen-binding fragment thereof, an antibody-drug conjugate or antigen-binding fragment thereof, or an antibody-like molecule. A polypeptide binding domain can be introduced into a J-chain by appropriately selecting the location and type of addition (e.g. direct or indirect fusion, chemical tethering, etc.).

In certain aspects, the binding domain can be an antibody or an antigen-binding fragment of an antibody, including monospecific, bispecific, and multi-specific antibodies and antibody fragments. The antibody fragment can be, without limitation, a Fab fragment, a Fab' fragment, a F(ab')$_2$ fragment, an scFv, (scFv)$_2$ fragment, single-chain antibody molecules, minibodies, or multispecific antibodies formed from antibody fragments. In certain aspects, the antibody fragment is a scFv.

In other aspects, the binding domain can be an antibody-like molecule, for example, a human domain antibody (dAb), Dual-Affinity Re-Targeting (DART) molecule, a diabody, a di-diabody, dual-variable domain antibody, a Stacked Variable Domain antibody, a Small Modular Immuno Pharmaceutical (SMIP), a Surrobody, a strand-exchange engineered domain (SEED)-body, or TandAb.

The binding domain can be introduced into the native J-chain sequence at any location that allows the binding of the binding domain to its binding target without interfering with the binding of the recipient IgM or IgA molecule to its binding target or binding targets or the ability of the J-chain to effectively incorporated into an IgA dimer or an IgM pentamer. In certain aspects the binding domain can be inserted at or near the C-terminus, at or near the mature N-terminus (i.e., amino acid number 23 of SEQ ID NO: 49 following cleavage of the signal peptide) or at an internal location that, based on the three-dimensional structure of the J-chain is accessible. In certain aspects, the binding domain can be introduced into the native sequence J-chain without about 10 residues from the C-terminus or without about 10 amino acid residues from the mature N-terminus, of the human J-chain of SEQ ID NO: 49. In another aspect, the binding domain can be introduced into the native sequence human J-chain of SEQ ID NO: 49 in between cysteine residues 114 and 123 of SEQ ID NO: 49, or at an equivalent location of another native sequence J-chain. In a further aspect, the binding domain can be introduced into a native sequence J-chain, such as a J-chain of SEQ ID NO: 49, at or near a glycosylation site. In certain aspects, the binding domain can be introduced into the native sequence human J-chain of SEQ ID NO: 49 within about 10 amino acid residues from the C-terminus.

Introduction can be accomplished by direct or indirect fusion, i.e. by the combination of the J-chain and binding domain in one polypeptide chain by in-frame combination of their coding nucleotide sequences, with or without a peptide linker. The peptide linker (indirect fusion), if used, can be about 1 to 50, or about 1 to 40, or about 1 to 30, or about 1 to 20, or about 1 to 10, or about 10 to 20 amino acids in length, and can be present at one or both ends of the binding domain to be introduced into the J-chain sequence. In certain aspects, the peptide linker is about 10 to 20, or 10 to 15 amino acids long. In certain aspects the peptide linker is 15 amino acids long. In certain aspects the peptide linker is (GGGGS)$_3$ (SEQ ID NO: 67).

It is also possible to introduce more than one heterologous polypeptide, e.g., more than one binding domain, into a J-chain.

The modified J-chain can be produced by well-known techniques of recombinant DNA technology, by expressing a nucleic acid encoding the modified J-chain in a suitable prokaryotic or eukaryotic host organism.

The modified J-chain can also be co-expressed with the heavy and light chains of the recipient IgM or IgA binding molecules as described elsewhere herein. The recipient binding molecule, prior to modified J-chain incorporation, can be monospecific, bispecific or multi-specific, e.g., a monospecific, bispecific, or multispecific IgA or IgM antibody. Bispecific and multi-specific IgM and IgA binding molecules, including antibodies, are described, for example, in U.S. Application Ser. Nos. 61/874,277 and 61/937,984, the entire contents of which are hereby expressly incorporated by reference.

In certain aspects, an anti-CD20 IgM or IgA binding molecule as described herein can include a modified J-chain with binding specificity for an immune effector cell, such as a T-cell, NK-cell, a macrophage, or a neutrophil. In certain aspects the effector cell is a T-cell and the binding target is CD3 (discussed below). By activating and redirecting effector cells, e.g. effector T-cells, to CD20-expressing B cells, e.g., malignant B cells, a bispecific anti-CD20×anti-CD3 IgM or IgA binding molecule as provided herein can produce an enhanced immune response against the target, the response comprising, e.g., complement-mediated cytotoxicity and/or antibody dependent cellular cytotoxicity (ADCC), thereby further increasing potency and efficacy. In certain aspects, a bispecific anti-CD20×anti-CD3 IgM or IgA binding molecule as provided herein comprising a modified J-chain can be used for the treatment of B-cell related cancers.

In the case of T-cells, cluster of differentiation 3 (CD3) is a multimeric protein complex, known historically as the T3 complex, and is composed of four distinct polypeptide chains (ε, γ, δ, ζ) that assemble and function as three pairs of dimers (εγ, εδ, ζζ). The CD3 complex serves as a T-cell co-receptor that associates non-covalently with the T-cell receptor (TCR). Components of this CD3 complex, especially CD3ε, can be targets for a modified J-chain of a bispecific IgM or IgA binding molecule provided herein.

In certain aspects, a bispecific anti-CD20×anti-CD3 IgM or IgA binding molecule binds to CD20 via the antibody binding domains, while the J-chain is modified to bind to CD3ε.

In certain aspects the anti-CD3ε binding domain of a modified J-chain provided herein is a scFv. The anti CD3ε scFv can be fused at or near the N-terminus of the J-chain, or at or near the C-terminus of the J-chain either directly or indirectly with a synthetic linker introduced in between the scFv and the J-chain sequences, e.g., a (GGGGS)$_3$ linker (SEQ ID NO: 67). In certain aspects the scFv comprises the VH and VL regions of visilizumab (Nuvion). In certain aspects the modified J-chain comprises a scFv comprising the VH of visilizumab, a (GGGGS)$_3$ linker, and the VL of visilizumab.

In certain aspects the modified J-chain comprises a scFv of visilizumab fused to the N-terminus of the human J-chain through a 15-amino acid (GGGGS)$_3$ linker, a modified J-chain referred to herein as V15J. V15J can further include a signal peptide to facilitate transport and assembly into an IgM or IgA binding molecules. The mature V15J protein is presented as SEQ ID NO: 64, the precursor version, comprising a 19-amino acid-immunoglobulin heavy chain signal peptide is presented as SEQ ID NO: 63. In certain aspects the modified J-chain comprises a scFv of visilizumab fused to the C-terminus of the human J-chain through a 15-amino acid (GGGGS)$_3$ linker, a modified J-chain referred to herein as J15V. J15V can further include a signal peptide to facilitate transport and assembly into an IgM or IgA binding molecules. The mature J15V protein is presented as SEQ ID NO: 65, the precursor version, comprising the 22-amino acid-human J-chain signal peptide is presented as SEQ ID NO: 66. In certain aspects, other signal peptides can be used. Selection and inclusion of suitable signal peptides to facilitate expression, secretion, and incorporation of a modified J-chain into an anti-CD20 IgM or IgA binding molecule as provided herein is well within the capabilities of a person of ordinary skill in the art.

CD20 Binding Domains

In certain aspects the CD20 antigen binding domain comprises six immunoglobulin complementarity determining regions HCDR1, HCDR2, HCDR3, LCDR1, LCDR2, and LCDR3, wherein at least one, at least two, at least three, at least four, at least five, or at least six CDRs are related to the corresponding CDRs of 1.5.3 disclosed in U.S. Patent Publication No. 2007-0014720. The CD20 antigen binding domain can include an HCDR1 comprising the amino acid sequence of SEQ ID NO: 39 or SEQ ID NO: 39 with one, two, three, four, or five single amino acid substitutions, e.g., one or two single amino acid substitutions. The CD20 antigen binding domain can include an HCDR2 comprising the amino acid sequence of SEQ ID NO: 40 or SEQ ID NO: 40 with one, two, three, four, or five single amino acid substitutions, e.g., one or two single amino acid substitutions. The CD20 antigen binding domain can include an HCDR3 comprising the amino acid sequence of SEQ ID NO: 41, or SEQ ID NO: 41 with one, two, three, four, or five single amino acid substitutions, e.g., one or two single amino acid substitutions. The CD20 antigen binding domain can include an LCDR1 comprising the amino acid sequence of SEQ ID NO: 43, or SEQ ID NO: 43 with one, two, three, four, or five single amino acid substitutions, e.g., one or two single amino acid substitutions. The CD20 antigen binding domain can include an LCDR2 comprising the amino acid sequence of SEQ ID NO: 44 or SEQ ID NO: 44 with one, two, three, four, or five single amino acid substitutions, e.g., one or two single amino acid substitutions. The CD20 antigen binding domain can include an LCDR3 comprising the amino acid sequence of SEQ ID NO: 45 or SEQ ID NO: 45 with one, two, three, four, or five single amino acid substitutions, e.g., one or two single amino acid substitutions. The CD20 antigen binding domain can include any one, any two, any three, any four, any five or all six of the CDR amino acid sequences as described above. In certain aspects the CD20 antigen binding domain includes an HCDR1 comprising the amino acid sequence SEQ ID NO: 39, an HCDR2 comprising the amino acid sequence SEQ ID NO: 40, an HCDR3 comprising the amino acid sequence SEQ ID NO: 41, an LCDR1 comprising the amino acid sequence SEQ ID NO: 43, an LCDR2 comprising the amino acid sequence SEQ ID NO: 44, and an LCDR3 comprising the amino acid sequence SEQ ID NO: 45.

In certain aspects the CD20 antigen binding domain comprises an antibody heavy chain variable region (VH) and an antibody light chain variable region (VL), wherein the VH region, the VL region, or both the VH and VL regions are related to the corresponding VH and VL of 1.5.3 disclosed in U.S. Patent Publication No. 2007-0014720. In certain aspects the VH can comprise an amino acid sequence at least 60%, at least 65%, at least 70%, at least 75%, at least 80%, at least 85%, at least 90%, at least 95% or 100% identical to SEQ ID NO: 38. In certain aspects the VL can comprise an amino acid sequence at least at least 60%, at least 65%, at least 70%, at least 75%, at least 80%, at least 85%, at least 90%, at least 95% or 100% identical to SEQ ID NO: 42. In certain aspects the VH comprises the amino acid sequence SEQ ID NO: 38 and the VL comprises the amino acid sequence SEQ ID NO: 42.

While a variety of different dimeric, pentameric, or hexameric binding molecules can be contemplated by a person of ordinary skill in the art based on this disclosure, and as such are included in this disclosure, in certain aspects, a binding molecule as described above is provided in which each binding unit comprises two IgA or IgM heavy chains each comprising a VH situated amino terminal to the IgA or IgM constant region or fragment thereof, and two immunoglobulin light chains each comprising a VL situated amino terminal to an immunoglobulin light chain constant region.

Moreover, in certain aspects, at least one binding unit of the binding molecule, or at least two, at least three, at least four, at least five, or at least six binding units of the binding molecule, comprises or comprise two of the CD20 antigen binding domains as described above. In certain aspects the two CD20 antigen binding domains in the binding unit of the binding molecule, or the two, three, four, five, or six binding units of the binding molecule, can be different from each other, or they can be identical.

In certain aspects, the two IgM heavy chains within the one, two, three, four, five, or six binding unit(s) of the binding molecule are identical. In certain aspects, two identical IgM heavy chains within at least one binding unit, or within at least two, at least three, at least four, at least five, or at least six binding units of the binding molecule comprise the amino acid sequence SEQ ID NO: 56.

In certain aspects, the two light chains within the one, two, three, four, five, or six binding unit(s) of the binding molecule are identical. In certain aspects, two identical light chains within at least one binding unit, or within at least two, at least three, at least four, at least five, or at least six binding units of the binding molecule are kappa light chains, e.g., human kappa light chains, or lambda light chains, e.g., human lambda light chains. In certain aspects, two identical light chains within at least one binding unit, or within at least two, at least three, at least four, at least five, or at least six binding units of the binding molecule each comprise the amino acid sequence SEQ ID NO: 58.

In certain aspects at least one, at least two, at least three, at least four, at least five, or at least six binding units of a dimeric, pentameric, or hexameric binding molecule provided by this disclosures comprises or each comprise two identical IgM heavy chains each comprising the amino acid sequence SEQ ID NO: 56, and two identical light chains each comprising the amino acid sequence SEQ ID NO: 58. According to this aspect, the CD20 antigen binding domains in the one, two, three, four, five, or six binding unit(s) of the binding molecule, can be identical. Further according to this aspect, a dimeric, pentameric, or hexameric binding molecule as provided herein can comprise at least one, at least two, at least three, at least four, at least five, at least six, at least seven, at least eight, at least nine, at least ten, at least eleven, or at least twelve copies of a CD20 antigen binding domain as described above. In certain aspects at least two, at least three, at least four, at least five, or at least six of the binding units can be identical and, in certain aspects the binding units can comprise identical antigen binding domains, e.g., at least two, at least three, at least four, at least five, at least six, at least seven, at least eight, at least nine, at least ten, at least eleven, or at least twelve CD20 antigen binding domains can be identical. In certain aspects the identical CD20 antigen binding domain can comprise a VH with the amino acid sequence SEQ ID NO: 38, and a VL with the amino acid sequence SEQ ID NO: 42.

In certain aspects, a dimeric, pentameric, or hexameric CD20 binding molecule as provided herein can possess advantageous structural or functional properties compared to other binding molecules. For example, the dimeric, pentameric, or hexameric CD20 binding molecule can possess improved activity in a biological assay, either in vitro or in vivo, than a corresponding binding molecule, e.g., an IgG1 1.5.3 as disclosed in U.S. Patent Publication No. 2007-0014720. Biological assays include, but are not limited to, complement-dependent cellular cytotoxicity (CDC) and antibody dependent cellular cytotoxicity (ADCC).

In certain aspects a dimeric, pentameric, or hexameric binding molecule as provided herein can direct complement-mediated, T-cell-mediated, or both complement-mediated and T-cell-mediated killing of a CD-20-expressing cell, e.g., a CD20-expressing B cell, at higher potency than an equivalent amount of a monospecific, bivalent IgG1 antibody or fragment thereof that specifically binds to the same CD20 epitope as the CD20 antigen binding domain, e.g., an IgG1 version of 1.5.3 comprising human IgG1 and a VH with the amino acid sequence SEQ ID NO: 38 and a VL with the amino acid sequence SEQ ID NO: 42. In certain aspects a dimeric, pentameric, or hexameric binding molecule as provided herein can direct complement-mediated, T-cell-mediated, or both complement-mediated and T-cell-mediated killing of a CD20-expressing cell, e.g., a CD20-expressing B cell at higher potency than an equivalent amount of monospecific, bivalent CD20 monoclonal antibody or fragment thereof, where the antibody is, or comprises the same VH and VL regions as, e.g., rituximab (Genentech), ofatumumab (Glaxo SmithKline), veltuzumab (Takeda), ocaratuzumab (Lilly), tositumumab (Glaxo SmithKline), or obinutumumab (Roche/Genentech).

By "potency" is meant the least amount of a given binding molecule necessary to achieve a given biological result, e.g., killing of 50% of the cells in a given assay, e.g., a CDC or ADCC assay ($IC_{50}$). Potency can be expressed as a curve in which % survival of cells is on the Y axis, and binding molecule concentration (in, e.g., µg/ml or µM) is on the X axis.

In certain aspects CDC can be measured in vitro, and the CD20-expressing cell can be an immortalized cell line, e.g., a B-cell lymphoma cell line, e.g., a Ramos cell line, a Raji cell line, a Daudi cell line, a Namalwa cell line, a Granta cell line, a Z138 cell line, a DoHH2 cell line, or a DB cell line. Similar cell lines are known and are easily obtained by a person of ordinary skill in the art.

In certain aspects, CDC can be measured or demonstrated in vitro or in vivo, and the CD-20-expressing cell line is a malignant B cell obtained from, or in, a subject, e.g., a human patient, with cancer, e.g., a B-cell related lymphoma, leukemia, or myeloma. In certain aspects the cancer is minimally responsive or non-responsive to conventional therapy, e.g., chemotherapy, or monoclonal antibody therapy with one or more of, e.g., rituximab (Genentech), ofatumumab (Glaxo SmithKline), veltuzumab (Takeda), ocaratu- zumab (Lilly), tositumumab (Glaxo SmithKline), or obinutumumab (Roche/Genentech). In certain aspects a dimeric, pentameric, or hexameric binding molecule comprising any one or more of the binding domains described herein, e.g., in Table 5, is provided.

In certain aspects, ADCC can be measured in vitro through T-cell activation assays, e.g., by co-culturing CD20-expressing B-cells and engineered CD3-expression T-cells in the presence of a bispecific anti-CD20×anti-CD3 IgM binding molecule as provided herein, and measuring T-cell activation through cytokine release, target cell lysis, or other detection method. In certain aspects ADCC can be measured through T-cell directed B-cell killing. In certain aspects the CD20-expressing cell can be an immortalized cell line, e.g., a B-cell lymphoma cell line, e.g., a Ramos cell line, a Raji cell line, a Daudi cell line, a Namalwa cell line, a Granta cell line, a Z138 cell line, a DoHH2 cell line, or a DB cell line. Similar cell lines are known and are easily obtained by a person of ordinary skill in the art. In certain aspects the CD20-expressing cell line can be derived from a patient suffering from a B-cell related cancer.

In certain aspects, the totality of killing of CD20+ cells, e.g., by CDC, ADCC, and other modes of killing, e.g., apoptosis, can be tested in vitro in an assay using whole blood that includes both T-cells and complement.

In certain aspects, e.g., where the binding molecule is a pentameric binding molecule comprising five identical binding units each comprising two identical CD20 binding domains with, e.g., the VH and VL of 1.5.3, tested in a CDC assay using, e.g., the CD20-expressing Raji cell line, the binding molecule can direct complement mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of the monospecific bivalent IgG1 antibody, e.g., 1.5.3 or rituximab, as measured, e.g., in µg/ml. In certain aspects, where the CD20-expressing cell is a Ramos cell line, the binding molecule can direct complement-mediated killing with an $IC_{50}$ at least ten-fold, at least 20-fold, at least 30-fold, at least 40-fold, at least 50-fold, at least 60-fold, at least 70-fold, at least 80-fold, at least 90-fold, or at least 100-fold lower than the $IC_{50}$ of an equivalent amount of the monospecific bivalent IgG1 antibody, as measured, e.g., as molar equivalents.

In certain aspects, e.g., a pentameric binding molecule comprising five identical binding units each comprising two identical binding domains with, e.g., the VH and VL of 1.5.3, or the VH and VL of rituximab, plus a wild-type or modified J-chain as provided herein can exhibit increased potency in a CDC assay performed in cells exhibiting lower CD20 expression levels. For example, rituximab-derived anti-human CD20 IgM+J or 1.5.3 anti-CD20 IgM+J, tested in a CDC assay using the CD20-expressing DoHH2 (CD20 high expression) and Z138 (CD20 low expression) cell lines, can direct complement-mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of the monospecific bivalent IgG1 antibody equivalents, e.g., rituximab (IgG1), or 1.5.3 (IgG1), as measured, e.g., as molar equivalents. In certain aspects, rituximab-derived anti-human CD20 IgM+J and 1.5.3 anti-CD20 IgM+J, tested in a CDC assay using the Z138 (CD20 low expression) cell line, can direct complement-mediated killing of the cell line under conditions where 50% killing ($EC_{50}$) with the equivalent IgG molecules cannot be achieved even at a concentration of 100 nM.

In certain aspects, a bispecific pentameric binding molecule comprising five identical binding units each comprising two identical CD20 binding domains with, e.g., the VH and VL of 1.5.3, or the VH and VL of rituximab, plus a modified J-chain capable of binding to human CD3, e.g., V15J or J15V as provided herein, can exhibit increased potency in an ADCC assay. For example, rituximab-derived anti-human CD20 IgM+ V15J or J15V, or 1.5.3 anti-CD20 IgM+ V15J or J15V, tested in a T-cell activation assay, e.g., using the CD20-expressing DB cell line co-cultured with engineered Jurkat T-cells, can facilitate T-cell mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of a monovalent bispecific binding molecule that binds B-cells and T-cells, e.g., a bispecific anti-CD19 (monovalent)×anti-CD3 (monovalent) molecule blinatumomab.

In certain aspects, a monospecific or bispecific pentameric binding molecule comprising five identical binding units each comprising two identical binding domains with, e.g., the VH and VL of 1.5.3, or the VH and VL of rituximab, plus a wild-type J-chain or a modified J-chain capable of binding to human CD3, e.g., V15J or J15V as provided herein, can exhibit increased potency in a whole-blood in vitro cytotoxicity assay. For example, 1.5.3 anti-CD20 IgM+V15J or J15V, or 1.5.3 anti-CD20 IgM+J, tested in a KILR™ in vitro cytotoxicity assay using the CD20-expressing KILR™ ARH-77 cell line co-cultured with Hirudin anti-coagulated human blood can achieve killing of the KILR™ ARH-77 cell line with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of a monospecific bivalent anti-CD20 binding molecule, e.g., 1.5.3 IgG, or a monovalent bispecific binding molecule that binds B-cells and T-cells, e.g., a bispecific anti-CD19 (monovalent)×anti-CD3 (monovalent) molecule blinatumomab.

In certain aspects, a monospecific or bispecific pentameric binding molecule comprising five identical binding units each comprising two identical binding domains with, e.g., the VH and VL of 1.5.3, or the VH and VL of rituximab, plus a wild-type J-chain or a modified J-chain capable of binding to human CD3, e.g., V15J or J15V as provided herein, can exhibit significant B-cell killing in vivo, for example in a humanized mouse model as described elsewhere herein.

Polynucleotides, Vectors, and Host Cells

The disclosure further provides a polynucleotide, e.g., an isolated, recombinant, and/or non-naturally-occurring polynucleotide, comprising a nucleic acid sequence that encodes a polypeptide subunit of the dimeric, pentameric, or hexameric binding molecule as described above. By "polypeptide subunit" is meant a portion of a binding molecule, binding unit, or antigen binding domain that can be independently translated. Examples include, without limitation, an antibody variable domain, e.g., a VH or a VL, a single chain Fv, an antibody heavy chain, an antibody light chain, an antibody heavy chain constant region, an antibody light chain constant region, and/or any fragment thereof.

In certain aspect, the polypeptide subunit can comprise an IgA or IgM heavy chain constant region and at least the antibody VH portion of the CD20 antigen binding domain. In certain aspects the polynucleotide can encode a polypeptide subunit comprising a human IgA or IgM constant region or fragment thereof fused to the C-terminal end of a VH, where the VH comprises an HCDR1, HCDR2, and HCDR3, wherein the HCDR1 comprises the amino acid sequence of SEQ ID NO: 39 or SEQ ID NO: 39 with one, two, three, four, or five single amino acid substitutions, e.g., one or two single amino acid substitutions; the HCDR2 comprises the amino acid sequence of SEQ ID NO: 40 or SEQ ID NO: 40 with one, two, three, four, or five single amino acid substitutions, e.g., or two single amino acid substitutions; the HCDR3 comprises the amino acid sequence of SEQ ID NO: 41, SEQ ID NO: 41 with one, two, three, four, or five single amino acid substitutions, e.g., one or two single amino acid substitutions; or the VH comprises an amino acid sequence at least 60%, at least 65%, at least 70%, at least 75%, at least 80%, at least 85%, at least 90%, at least 95% or 100% identical to SEQ ID NO: 38. In certain aspects the polypeptide subunit comprises the amino acid sequence SEQ ID NO: 56.

In certain aspects, the polypeptide subunit can comprise an antibody VL portion of a CD20 antigen binding domain as described above. In certain aspects the polypeptide subunit can comprise a human antibody light chain constant region or fragment thereof fused to the C-terminal end of a VL, where the VL comprises an LCDR1, LCDR2, and LCDR3, wherein the LCDR1 comprises the amino acid sequence of SEQ ID NO: 43, or SEQ ID NO: 43 with one, two, three, four, or five single amino acid substitutions, e.g., one or two single amino acid substitutions; the LCDR2 comprises the amino acid sequence of SEQ ID NO: 44 or SEQ ID NO: 44 with one, two, three, four, or five single amino acid substitutions, e.g., one or two single amino acid substitutions; and the LCDR3 comprises the amino acid sequence of SEQ ID NO: 45 or SEQ ID NO: 45 with one, two, three, four, or five single amino acid substitutions, e.g., one or two single amino acid substitutions; or the VL comprises an amino acid sequence at least 60%, at least 65%, at least 70%, at least 75%, at least 80%, at least 85%, at least 90%, at least 95% or 100% identical to SEQ ID NO: 42. In certain aspects the polypeptide subunit comprises the amino acid sequence SEQ ID NO: 58.

In certain aspects, the polypeptide subunit can comprise an antibody VH or an antibody VL portion of a CD20 antigen binding domain comprising any one or more of the VH or VL amino acid sequences described above and/or in Table 5.

The disclosure further provides a composition comprising two or more polynucleotides, where the two or more polynucleotides collectively can encode a dimeric, pentameric, or hexameric binding molecule as described above. In certain aspects the composition can include a polynucleotide encoding an IgA or IgM heavy chain or fragment thereof, e.g, a human IgA or IgM heavy chain as described above where the IgA or IgM heavy chain comprises at least the VH of a CD20 antigen binding domain, and a polynucleotide encoding a light chain or fragment thereof, e.g., a human kappa or lambda light chain that comprises at least the VL of a CD20 antigen binding domain. A polynucleotide composition as provided can further include a polynucleotide encoding a J-chain, e.g., a human J-chain, or a fragment thereof or a variant thereof. In certain aspects the polynucleotides making up a composition as provided herein can be situated on two or three separate vectors, e.g., expression vectors. Such vectors are provided by the disclosure. In certain aspects two or more of the polynucleotides making up a composition as provided herein can be situated on a single vector, e.g., an expression vector. Such a vector is provided by the disclosure.

The disclosure further provides a host cell, e.g., a prokaryotic or eukaryotic host cell, comprising a polynucleotide or two or more polynucleotides encoding a dimeric, pentameric, or hexameric CD20 binding molecule as provided herein, or any subunit thereof, a polynucleotide composition as provided herein, or a vector or two, three, or more vectors that collectively encode a dimeric, pentameric, or hexameric CD20 binding molecule as provided herein, or any subunit thereof. In certain aspects a host cell provided by the disclosure can express a dimeric, pentameric, or hexameric CD20 binding molecule as provided by this disclosure, or a subunit thereof.

In a related aspect, the disclosure provides a method of producing a dimeric, pentameric, or hexameric CD20 binding molecule as provided by this disclosure, where the method comprises culturing a host cell as described above and recovering the binding molecule.

Methods of Use

This disclosure provides improved methods for directing complement-mediated, T-cell-mediated, or both complement-mediated and T-cell-mediated killing of cells that express CD20, e.g., B cells, e.g., malignant or immortalized B cells, using a dimeric, pentameric, or hexameric IgA- or IgM-based CD20 binding molecule. The methods described below can utilize binding molecules comprising CD20 antigen binding domains derived from any CD20 antibody, including without limitation 1.5.3 as disclosed in U.S. Patent Publication No. 2007-0014720, rituximab, ofatumumab, veltuzumab, ocaratuzumab, obinutumumab, or variants, derivatives, or analogs thereof, where the dimeric, pentameric, or hexameric CD20 binding molecule can provide improved complement-mediated, T-cell-mediated, or both complement-mediated and T-cell-mediated killing of CD20-expressing cells as compared to an equivalent IgG antibody, fragment, variant, derivative, or analog thereof, comprising the same antigen binding domain. In certain aspects the IgA- or IgM-based CD20 binding molecule further comprises a J-chain, either a wild-type J-chain or a modified J-chain capable of binding to human CD3, e.g., V15J or J15V as provided herein. Based on this disclosure, construction of a dimeric, pentameric, or hexameric IgM-based CD20 binding molecule comprising any CD20 antigen binding domain of interest is well within the capabilities of a person of ordinary skill in the art. The improved activity can, for example, allow a reduced dose to be used, or can result in more effective killing of cells that are resistant to killing by the original antibody. By "resistant" is meant any degree of reduced activity of a CD20 antibody, e.g., rituximab, on the CD20-expressing cell. Use of an IgA-based binding molecule can allow, for example, greater tissue distribution for a binding molecule provided herein.

In certain aspects, this disclosure provides a method for directing improved complement-mediated, T-cell-mediated, or both complement-mediated and T-cell-mediated killing of a CD20-expressing cell, where the method includes contacting a CD20-expressing cell with a dimeric, pentameric, or hexameric binding molecule as described herein, where the binding molecule can direct complement-mediated, T-cell-mediated, or both complement-mediated and T-cell-mediated killing of a CD-20-expressing cell, e.g., a CD20-expressing B cell, at higher potency than an equivalent amount of a monospecific, bivalent IgG, e.g., IgG1 antibody or fragment thereof that specifically binds to the same CD20 epitope as the CD20 antigen binding domain, e.g., rituximab, which comprises a human IgG1 and a VH with the amino acid sequence SEQ ID NO: 1 and a VL with the amino acid sequence SEQ ID NO: 5. The dimeric or pentameric binding molecule can further include a wild-type J-chain or a modified J-chain capable of binding to human CD3, e.g., V15J or J15V as provided herein. In certain aspects a dimeric, pentameric, or hexameric binding molecule as provided herein can direct complement-mediated, T-cell-mediated, or both complement-mediated and T-cell-mediated killing of a CD20-expressing cell, e.g., a CD20-expressing B cell at higher potency than an equivalent amount of monospecific, bivalent CD20 monoclonal antibody or fragment thereof, where the antibody is, or comprises the same VH and VL regions as, e.g., ofatumumab, veltuzumab, ocaratuzumab, or obinutumumab.

This disclosure thus provides a method for directing complement-mediated, T-cell-mediated, or both complement-mediated and T-cell-mediated killing of a CD20-expressing cell, where the method includes: contacting a CD20-expressing cell with a dimeric, pentameric, or hexameric binding molecule comprising two, five, or six bivalent binding units, respectively, wherein each binding unit comprises two IgA or IgM heavy chain constant regions or fragments thereof and two antigen binding domains. Non-limiting examples of suitable binding molecules include 1.5.3-based dimeric, pentameric, or hexameric binding molecule provided by this disclosure, or other binding molecules as described elsewhere in this disclosure. The dimeric or pentameric binding molecule can further include a wild-type J-chain or a modified J-chain capable of binding to human CD3, e.g., V15J or J15V as provided herein. According to the method at least one antigen binding domain of the binding molecule is a CD20 antigen binding domain. Moreover, according to the method the binding molecule can direct complement-mediated, T-cell-mediated, or both complement-mediated and T-cell-mediated killing of a CD-20-expressing cell at higher potency than an equivalent amount of a monospecific, bivalent IgG, e.g., IgG1 antibody or fragment thereof that specifically binds to the same CD20 epitope as the CD20 antigen binding domain, e.g., a bivalent IgG1 antibody comprising a CD20 antigen binding domain similar to, e.g., identical to, a CD20 antigen binding domain of the dimeric, pentameric, or hexameric binding molecule provided by this disclosure.

For example, the disclosure provides a method for directing complement-mediated, T-cell-mediated, or both complement-mediated and T-cell-mediated killing of a CD20-expressing cell, where the method includes: contacting a CD20-expressing cell with a dimeric, pentameric, or hexameric binding molecule comprising at least one antigen binding domain related to 1.5.3, as described elsewhere herein, where the binding molecule can direct complement-mediated, T-cell-mediated, or both complement-mediated and T-cell-mediated killing of a CD-20-expressing cell at higher potency than an equivalent amount of a monospecific, bivalent IgG1 antibody or fragment thereof that specifically binds to the same CD20 epitope as 1.5.3-related CD20 antigen binding domain. The dimeric or pentameric binding molecule can further include a wild-type J-chain or a modified J-chain capable of binding to human CD3, e.g., V15J or J15V as provided herein. In certain aspects the monospecific, bivalent IgG1 antibody is 1.5.3, and comprises a VH having the amino acid sequence SEQ ID NO: 38 and a VL having the amino acid sequence SEQ ID NO: 42.

In certain aspects, e.g., where the binding molecule is a pentameric binding molecule comprising five identical binding units each comprising two identical binding domains with the VH and VL of 1.5.3, tested in a CDC assay using the CD20-expressing Raji cell line, the binding molecule can direct complement-mediated killing with an $IC_{50}$ at least one-fold, at least two-fold, at least three-fold, at least four-fold, at least five-fold, at least ten-fold, at least 20-fold, at least thirty-fold, at least forty-fold, at least 50-fold, at least 100-fold, at least 150-fold, at least 200-fold or more lower than the $IC_{50}$ of an equivalent amount of the monospecific bivalent IgG1 antibody, e.g., 1.5.3, as measured, e.g., in µg/ml or in molar equivalents.

In certain aspects the CD-20-expressing cell is an immortalized cell line, e.g. a B cell leukemia or lymphoma cell line. The cell line can be, without limitation, a Ramos cell line, a Raji cell line, a Daudi cell line, a Namalwa cell line, a Granta cell line, a Z138 cell line, a DoHH2 cell line, or a DB cell line. Other cell lines that can be useful in the methods provided herein can easily be identified by a person of ordinary skill in the art.

In certain aspects the cell line is a Granta cell line, and the dimeric, pentameric, or hexameric binding molecule can direct complement-mediated killing of the cell line at about six times the potency of rituximab as measured in µg/ml. In certain aspects the cell line is a Ramos cell line, and the dimeric, pentameric, or hexameric binding molecule can direct complement-mediated killing of the cell line at about 30-40 times the potency of rituximab as measured in molar equivalents.

In certain aspects the cell line is a Raji cell line or a Ramos cell line, and the dimeric, pentameric, or hexameric binding molecule can direct complement-mediated killing of the cell line at about three times the potency of rituximab.

In certain aspects the CD20-expressing cell is a malignant B cell in a subject, e.g., a human patient, with cancer. The cancer can be, for example, a CD20-positive leukemia, lymphoma, or myeloma. In certain aspects the CD20-expressing cell line or malignant B cell is resistant, e.g., minimally responsive or non-responsive to killing by a commercially-available CD20 monoclonal antibody, e.g., the CD20-expressing cell line or malignant B cell in a subject with cancer is minimally responsive or non-responsive to rituximab therapy.

In another aspect the disclosure provides a method for directing complement-mediated, T-cell-mediated, or both complement-mediated and T-cell-mediated killing of a CD20-expressing cell, where the method includes: contacting a CD20-expressing cell with a dimeric, pentameric, or hexameric binding molecule comprising at least one antigen binding domain related to the CD20 mAb rituximab, or a fragment, variant, derivative, or analog thereof. The dimeric or pentameric binding molecule can further include a wild-type J-chain or a modified J-chain capable of binding to human CD3, e.g., V15J or J15V as provided herein.

In certain aspects the CD20 antigen binding domain of the dimeric, pentameric, or hexameric binding molecule comprises six immunoglobulin complementarity determining regions HCDR1, HCDR2, HCDR3, LCDR1, LCDR2, and LCDR3, wherein at least one, at least two, at least three, at least four, at least five, or at least six CDRs are related to the corresponding CDRs of the CD20 mAb rituximab. The CD20 antigen binding domain can include an HCDR1 comprising the amino acid sequence of SEQ ID NO: 2 or SEQ ID NO: 2 with one, two, three, four, or five single amino acid substitutions, e.g. one or two single amino acid substitutions. The CD20 antigen binding domain can include an HCDR2 comprising the amino acid sequence of SEQ ID NO: 3 or SEQ ID NO: 3 with one, two, three, four, or five single amino acid substitutions. For example, the HCDR2 can comprise the amino acid sequence SEQ ID NO: 16. The CD20 antigen binding domain can include an HCDR3 comprising the amino acid sequence of SEQ ID NO: 4, or SEQ ID NO: 4 with one, two, three, four, or five single amino acid substitutions, e.g., one, two, or three single amino acid substitutions. For example, the HCDR3 can comprise the amino acid sequence SEQ ID NO: 17, SEQ ID NO: 31, or SEQ ID NO: 36. The CD20 antigen binding domain can, in other aspects, include an HCDR3 comprising the amino acid sequence SEQ ID NO: 10, or SEQ ID NO: 10 with one, two, three, four, or five single amino acid substitutions. The CD20 antigen binding domain can, in other aspects, include an HCDR3 comprising the amino acid sequence SEQ ID NO: 31, or SEQ ID NO: 31 with one, two, three, four, or five single amino acid substitutions. The CD20 antigen binding domain can include an LCDR1 comprising the amino acid sequence of SEQ ID NO: 6, or SEQ ID NO: 6 with one, two, three, four, or five single amino acid substitutions, e.g., one, two, or three single amino acid substitutions. For example, the LCDR1 can comprise the amino acid sequence SEQ ID NO: 12, SEQ ID NO: 19, SEQ ID NO: 25, SEQ ID NO: 27, or SEQ ID NO: 33. The CD20 antigen binding domain can include an LCDR2 comprising the amino acid sequence of SEQ ID NO: 7 or SEQ ID NO: 7 with one, two, three, four, or five single amino acid substitutions, e.g., one or two single amino acid substitutions. For example, the LCDR2 can comprise the amino acid sequence SEQ ID NO: 13 or SEQ ID NO: 20. The CD20 antigen binding domain can include an LCDR3 comprising the amino acid sequence of SEQ ID NO: 8 or SEQ ID NO: 8 with one, two, three, four, or five single amino acid substitutions, e.g., one or two single amino acid substitutions. For example, the LCDR3 can comprise the amino acid sequence SEQ ID NO: 14, SEQ ID NO: 21, or SEQ ID NO: 34.

In certain aspects the CD20 antigen binding domain of the dimeric, pentameric, or hexameric binding molecule comprises a VH and a VL, wherein the VH region, the VL region, or both the VH and the VL regions are related to the corresponding VH and VL of rituximab. In certain aspects the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 1 and a VL amino acid sequence at least 60%, at least 65%, at least 70%, at least 75%, at least 80%, at least 85%, at least 90%, at least 95% or 100% identical to SEQ ID NO: 5.

In certain aspects the VH and VL can be derived from the CD20 mAb described in U.S. Pat. No. 7,679,900. For example, the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 9 and a VL amino acid sequence at least 60%, at least 65%, at least 70%, at least 75%, at least 80%, at least 85%, at least 90%, at least 95% or 100% identical to SEQ ID NO: 11.

In certain aspects the VH and VL can be derived from the CD20 mAb described in U.S. Pat. No. 8,153,125. For example, the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 15 and a VL amino acid sequence at least 60%, at least 65%, at least 70%, at least 75%, at least 80%, at least 85%, at least 90%, at least 95% or 100% identical to SEQ ID NO: 18.

In certain aspects the VH and VL can be derived from the CD20 mAb described in U.S. Pat. No. 8,337,844. For example, the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 22 or SEQ ID NO: 23 and a VL amino acid sequence at least 60%, at least 65%, at least 70%, at least 75%, at least 80%, at least 85%, at least 90%, at least 95% or 100% identical to SEQ ID NO: 24, SEQ ID NO: 26, SEQ ID NO: 28, or SEQ ID NO: 29.

In certain aspects the VH and VL can be derived from the CD20 mAb described in U.S. Pat. No. 8,337,844. For example, the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 30 and a VL amino acid sequence at least 60%, at least 65%, at least 70%, at least 75%, at least 80%, at least 85%, at least 90%, at least 95% or 100% identical to SEQ ID NO: 32.

In certain aspects the VH and VL can be derived from the CD20 mAb described in U.S. Pat. No. 7,151,164. For example, the CD20 antigen binding domain can comprise a VH amino acid sequence at least 60%, at least 65%, at least 70%, at least 75%, at least 80%, at least 85%, at least 90%, at least 95% or 100% identical to SEQ ID NO: 35 and a VL amino acid sequence at least 60%, at least 65%, at least 70%, at least 75%, at least 80%, at least 85%, at least 90%, at least 95% or 100% identical to SEQ ID NO: 37.

A dimeric, pentameric, or hexameric binding molecule for use in the methods provided herein, is a binding molecule with two, five, or six "binding units" as defined herein, that can specifically bind to CD20, e.g., human CD20. In certain aspects, a dimeric, pentameric, or hexameric binding molecule for use in the methods provided herein comprises two, five, or six bivalent binding units, respectively, where each binding unit includes two IgA or IgM heavy chain constant regions or fragments thereof. In certain aspects, the two IgA or IgM heavy chain constant regions are human heavy chain constant regions.

Where the binding molecule for use in the methods provided herein is pentameric, the binding molecule can further comprise a J-chain, or fragment thereof, or variant thereof. The J-chain can be a wild-type J-chain or a modified J-chain capable of binding to human CD3, e.g., V15J or J15V as provided herein.

An IgM heavy chain constant region of a binding molecule for use in the methods provided herein can include one or more of a Cµ1 domain, a Cµ2 domain, a Cµ3 domain, and/or a Cµ4 domain, provided that the constant region can serve a desired function in the binding molecule, e.g., associate with second IgM constant region to form an antigen binding domain, or associate with other binding units to form a hexamer or a pentamer. In certain aspects the two IgM heavy chain constant regions or fragments thereof within an individual binding unit each comprise a Cµ3 domain or fragment thereof, a Cµ4 domain or fragment thereof, a tailpiece (TP) or fragment thereof, or any combination of a Cµ3 domain a Cµ domain, and a TP or fragment thereof. In certain aspects the two IgM heavy chain constant regions or fragments thereof within an individual binding unit each further comprise a Cµ2 domain or fragment thereof, a Cµ1 domain or fragment thereof, or a Cµ1 domain or fragment thereof and a Cµ2 domain or fragment thereof.

While a variety of different dimeric, pentameric, or hexameric binding molecules for use in the methods provided herein can be contemplated by a person of ordinary skill in the art based on this disclosure, and as such are included in this disclosure, in certain aspects, a binding molecule for use in the methods provided herein is provided in which each binding unit comprises two IgA or IgM heavy chains each comprising a VH situated amino terminal to the IgA or IgM constant region or fragment thereof, and two immunoglobulin light chains each comprising a VL situated amino terminal to an immunoglobulin light chain constant region.

Moreover, in certain aspects, at least one binding unit of the binding molecule for use in the methods provided herein, or at least two, at least three, at least four, at least five, or at least six binding units of the binding molecule for use in the methods provided herein, comprises or comprise two of the CD20 antigen binding domains as described above. In certain aspects the two CD20 antigen binding domains in the one, two, three, four, five, or six binding unit(s) of the binding molecule for use in the methods provided herein can be different from each other, or they can be identical.

In certain aspects, the two IgM heavy chains within the one, two, three, four, five, or six binding unit(s) of the binding molecule for use in the methods provided herein are identical. In certain aspects, two identical IgM heavy chains within at least one binding unit, or within at least two, at least three, at least four, at least five, or at least six binding units of the binding molecule for use in the methods provided herein comprise the amino acid sequence SEQ ID NO: 52.

In certain aspects, the two light chains within the one, two, three, four, five, or six binding unit(s) of the binding molecule for use in the methods provided herein are identical. In certain aspects, two identical light chains within at least one binding unit, or within at least two, at least three, at least four, at least five, or at least six binding units of the binding molecule for use in the methods provided herein are kappa light chains, e.g., human kappa light chains, or lambda light chains, e.g., human lambda light chains. In certain aspects, two identical light chains within at least one binding unit, or within at least two, at least three, at least four, at least five, or at least six binding units of the binding molecule for use in the methods provided herein each comprise the amino acid sequence SEQ ID NO: 54.

In certain aspects at least one, at least two, at least three, at least four, at least five, or at least six binding units of a pentameric or hexameric binding molecule for use in the methods provided herein comprises or each comprise two identical IgM heavy chains each comprising the amino acid sequence SEQ ID NO: 52, and two identical light chains each comprising the amino acid sequence SEQ ID NO: 54. According to this aspect, the CD20 antigen binding domains in the one, two, three, four, five, or six binding unit(s) of the binding molecule can be identical. Further according to this aspect, a dimeric, pentameric, or hexameric binding molecule for use in the methods provided herein can comprise at least one, at least two, at least three, at least four, at least five, at least six, at least seven, at least eight, at least nine, at least ten, at least eleven, or at least twelve copies of a CD20 antigen binding domain as described above. In certain aspects at least two, at least three, at least four, at least five, or at least six of the binding units can be identical and, in certain aspects the binding units can comprise identical antigen binding domains, e.g., at least two, at least three, at least four, at least five, at least six, at least seven, at least eight, at least nine, at least ten, at least eleven, or at least twelve CD20 antigen binding domains can be identical. In certain aspects the identical CD20 antigen binding domain can comprise a VH with the amino acid sequence SEQ ID NO: 1 and a VL with the amino acid sequence SEQ ID NO: 5.

Dimeric, pentameric, or hexameric CD20 binding molecules for use in the methods provided herein can possess advantageous structural or functional properties compared to other binding molecules. For example, a dimeric, pentameric, or hexameric CD20 binding molecule for use in the methods provided herein can possess improved activity in a biological assay, either in vitro or in vivo, than a corresponding binding molecule, e.g., rituximab or a variant, analog, or derivative thereof. Biological assays include, but are not limited to, complement-dependent cellular cytotoxicity (CDC) and/or antibody dependent cellular cytotoxicity (ADCC).

Pharmaceutical Compositions and Administration Methods

Methods of preparing and administering a dimeric, pentameric, or hexameric CD20 binding molecule as provided herein to a subject in need thereof are well known to or are readily determined by those skilled in the art in view of this disclosure. The route of administration of a CD20 binding molecule can be, for example, oral, parenteral, by inhalation or topical. The term parenteral as used herein includes, e.g., intravenous, intraarterial, intraperitoneal, intramuscular, subcutaneous, rectal, or vaginal administration. While these forms of administration are contemplated as suitable forms, another example of a form for administration would be a solution for injection, in particular for intravenous or intraarterial injection or drip. A suitable pharmaceutical composition can comprise a buffer (e.g. acetate, phosphate or citrate buffer), a surfactant (e.g. polysorbate), optionally a stabilizer agent (e.g. human albumin).

As discussed herein, a dimeric, pentameric, or hexameric CD20 binding molecule as provided herein can be administered in a pharmaceutically effective amount for the in vivo treatment of diseases or disorders in which it's desirable to deplete B cells. In this regard, it will be appreciated that the disclosed binding molecules can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a dimeric, pentameric, or hexameric CD20 binding molecule as provided herein means an amount sufficient to achieve effective binding to a target and to achieve a therapeutic benefit. Suitable formulations are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a dimeric, pentameric, or hexameric CD20 binding molecule that can be combined with carrier materials to produce a single dosage form will vary depending, e.g., upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, a dimeric, pentameric, or hexameric CD20 binding molecule as provided herein can be administered to a subject in need of therapy in an amount sufficient to produce a therapeutic effect. A dimeric, pentameric, or hexameric CD20 binding molecule as provided herein can be administered to the subject in a conventional dosage form prepared by combining the antibody or antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of a dimeric, pentameric, or hexameric CD20 binding molecule, that when administered brings about a positive therapeutic response with respect to treatment of a patient with a disease or condition to be treated.

Therapeutically effective doses of the compositions disclosed herein, for treatment of diseases or disorders in which B cell depletion is desired, can vary depending upon many different factors, including means of administration, target site, physiological state of the patient, whether the patient is human or an animal, other medications administered, and whether treatment is prophylactic or therapeutic. In certain aspects, the subject or patient is a human, but non-human mammals including transgenic mammals can also be treated. Treatment dosages can be titrated using routine methods known to those of skill in the art to optimize safety and efficacy.

The amount of a dimeric, pentameric, or hexameric CD20 binding molecule to be administered is readily determined by one of ordinary skill in the art without undue experimentation given this disclosure. Factors influencing the mode of administration and the respective amount of a dimeric, pentameric, or hexameric CD20 binding molecule include, but are not limited to, the severity of the disease, the history of the disease, and the age, height, weight, health, and physical condition of the individual undergoing therapy. Similarly, the amount of a dimeric, pentameric, or hexameric CD20 binding molecule to be administered will be dependent upon the mode of administration and whether the subject will undergo a single dose or multiple doses of this agent.

This disclosure also provides for the use of a dimeric, pentameric, or hexameric CD20 binding molecule in the manufacture of a medicament for treating, preventing, or managing a disease or disorder in which B cell depletion is desirable, e.g., B cell lymphoma, leukemia, or myeloma.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds.

(1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freeman & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Generation of DNA Constructs for Expression of CD20-hIgM

Plasmid constructs that can express pentameric or hexameric IgM binding molecules that can specifically bind to CD20 were produced by the following method.

DNA fragments encoding the VH and VL regions of rituximab (SEQ ID NOs 1 and 5, respectively) or 1.5.3 (SEQ ID NOs 38 and 42, respectively) were synthesized by a commercial vendor (Genescript), with an EcoRV restriction site on the '5 end and an XbaI restriction site on the 3' end for subcloning into heavy chain and light chain expression vectors. The synthesized DNA constructs were re-suspended in Tris-EDTA buffer at 1 µg/ml. DNA samples (1 µg) were digested with EcoRV and XbaI, and the synthesized VH and VL were separated from the carrier plasmid DNA by electrophoresis. The digested DNA was ligated to pre-digested plasmid DNA (pFUSEss-CHIg-hM*03 for µ chain, pFUSE2ss-CLIg-hk for kappa chain, available from Invivogen) by standard molecular biology techniques. The ligated DNAs were transformed into competent bacteria and plated on LB plates with multiple selective antibiotics. Several bacterial colonies were picked, and DNA preparations were made by standard molecular biology techniques. The constructs encoding the heavy chain and light chains were verified by sequencing. The DNA and amino acid sequences of the rituximab IgM heavy chain are presented as SEQ ID NO: 51 and SEQ ID NO: 52, respectively, and the DNA and amino acid sequences of the rituximab light chain are presented as SEQ ID NO: 53 and SEQ ID NO: 54, respectively. The DNA and amino acid sequences of 1.5.3 IgM heavy chain are presented as SEQ ID NO: 55 and SEQ ID NO: 56, respectively, and the DNA and amino acid sequences of 1.5.3 light chain are presented as SEQ ID NO: 57 and SEQ ID NO: 58, respectively. The amino acid sequence of the human J-chain is presented as SEQ ID NO: 49.

The plasmid constructs encoding the IgM heavy chains and light chains, or the heavy chains, light chains, and J-chain were cotransfected into CHO cells, and cells that express the CD20 IgM antibody, either with or without J-chain, were selected, all according to standard methods.

Antibodies present in the cell supernatants were recovered using Capture Select IgM (Catalog 2890.05, BAC, Thermo Fisher) according to the manufacturer's protocol. Antibodies were evaluated on SDS PAGE under non-reducing conditions to show assembly of pentamers and hexamers. NuPage LDS Sample Buffer (Life Technologies) was added to samples before loading onto a NativePage Novex 3-12% bis-Tris Gel (Life Technologies Catalog # BN1003). Novex Tris-Acetate SDS Running Buffer (Life Technologies Catalog # LA0041) was used for gel electrophoresis. The gel was run until the dye front reached the bottom of the gel. After electrophoresis, the gel was stained with Colloidal Blue Stain (Life Technologies Catalog # LC6025). The results are shown in FIG. 4. Under non-reducing conditions, the pentameric 1.5.3 IgM (five H2L2 IgM units plus J-chain, FIG. 4, second panel, lane 3) and the pentameric rituximab IgM (first panel, lane 3) produced a protein band of approximately 1,000,000 molecular weight, and hexameric 1.5.3 IgM (six H2L2 IgM units, FIG. 4, second panel, lane 2) produced a protein band of approximately 1,180,000.

Example 2: Binding and Activity of CD20-hIgM

Detection of Binding Via CD20 ELISA Assay 96-well white polystyrene ELISA plates (Pierce 15042) were coated with 100 µL per well of 10 µg/mL or 0.3 µg/mL human CD20 with N-Fc fusion (AcroBiosystems, CD0-H526a) overnight at 4° C. Plates were then washed with 0.05% PBS-Tween and blocked with 2% BSA-PBS. After blocking, 100 µL of serial dilutions of 1.5.3 IgM, 1.5.3 IgG, standards, and controls were added to the wells and incubated at room temperature for 2 hours. The plates were then washed and incubated with HRP conjugated mouse anti-human kappa (Southern Biotech, 9230-05. 1:6000 diluted in 2% BSA-PBS) for 30 min. After 10 final washes using 0.05% PBS-Tween, the plates were read out using Super- Signal chemiluminescent substrate (ThermoFisher, 37070). Luminescent data were collected on an EnVision plate reader (Perkin-Elmer) and analyzed with GraphPad Prism using a 4-parameter logistic model.

The results are shown in FIG. 5A and FIG. 5B, comparing IgM vs. IgG by molar concentrations. The anti-CD20 IgM antibody exhibited more effective binding, at both CD20 antigen densities, and especially at the low CD20 antigen concentration (FIG. 5B).

Complement Dependent Cytotoxicity—Colorimetric Assay

Granta (DSMZ cat. # ACC 342), Raji (ATCC cat. # CCL-86), Ramos (ATCC cat. # CRL-1596), Nalm-6 (DSMZ cat. # ACC 128), and Namalwa (ATCC cat. # CRL-1432) cell lines were from ATCC and DSMZ. 50,000 cells of each cell line were seeded in a 96-well plate. Cells were treated with serially diluted commercially-available anti-human CD20 IgM (Invivogen cat. # hcd20-mab5) or anti-human CD20 IgG1 (Invivogen cat. # hcd20-mab1). Human serum complement (Quidel cat. # A113) was added to each well at a final concentration of 10%. The reaction mixtures were incubated at 37° C. for 1 hr. Cell Counting Kit-SK reagent (CCK-SK) (Dojindo cat. # CK04-13) was added at 1/10 the total reaction volume and plate was incubated for an additional 3 hours at 37° C. Absorbance at 450 nm was measured on a spectrophotometer.

Figure 6:
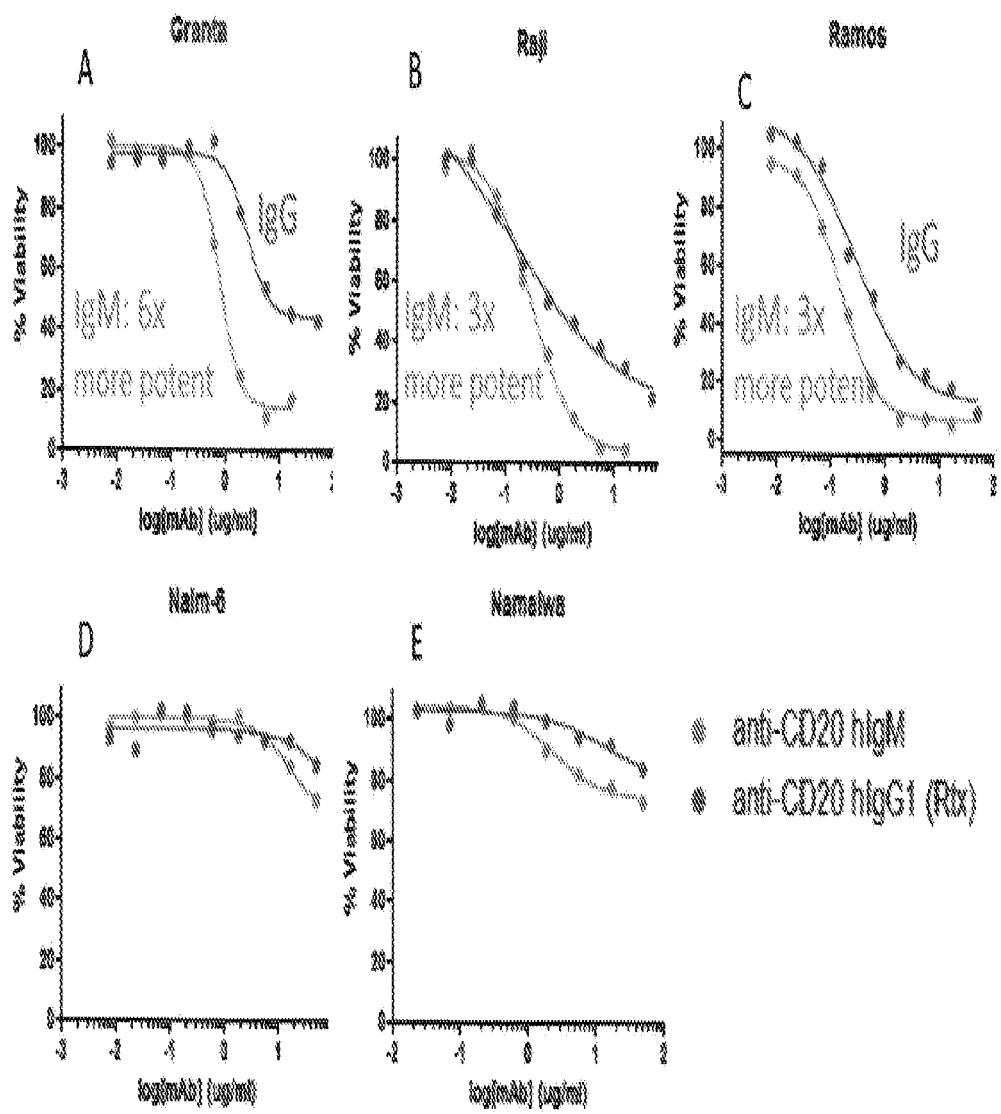

The results are shown in FIG. 6A-E. The IgM CD20 antibody was 6 times more potent at cell killing than IgG in Granta cells (FIG. 6A), three time more potent in Raji cells (FIG. 6B), and three times more potent in Ramos cells (FIG. 6C). Neither antibody was effective in killing Nalm-6 cells (FIG. 6D) or Namalwa cells (FIG. 6E), which express no, or low levels of CD20, respectively.

Complement Dependent Cytotoxicity—Luminescent Assay (a) The CD20-expressing Raji cell line (ATCC cat. # CCL-86) was used. 50,000 cells were seeded in a 96-well plate. Cells were treated with the following serially diluted antibodies: rituximab (IgG1), rituximab-derived anti-human CD20 IgM+J as produced in Example 1, or 1.5.3 anti-human CD20 IgM+J, produced as described in Example 1. Human serum complement (Quidel cat. # A113) was added to each well at a final concentration of 10%. The reaction mixtures were incubated at 37° C. for 4 hours. Cell Titer Glo reagent (Promega cat. # G7572) was added at a volume equal to the volume of culture medium present in each well. The plate was shaken for 2 minutes, incubated for 10 minutes at room temperature, and luminescence was measured on a luminometer.

The results are shown in FIG. 7 and Table 2. Anti-CD20 as an IgG (rituximab) achieved approximately half-maximal Raji cell killing with complement, whereas the IgM isotype (rituximab) achieved nearly maximal complement dependent cytotoxicity. Both IgM antibodies were more potent at complement dependent cytotoxicity than rituximab, and in this experiment, the 1.5.3-like IgM antibody was more potent than the anti-human IgM CD20 antibody carrying the rituximab VH and VL. The 1.5.3-like IgM antibody exhibited four-fold increased potency compared to that of the type 1 anti-CD20 (rituximab as IgM).

TABLE 2

| CDC ($IC_{50}$) on Raji cells (µg/ml) | |
|---|---|
| | $IC_{50}$ (µg/ml) |
| Anti-CD20 IgG1 (rituximab) | >50 |
| Anti-CD20 IgM | 2.0 |
| 1.5.3 IgM + J | 0.5 |

(b) The CDC assay as described above was repeated using the CD20-expressing Ramos cell line with the following serially diluted antibodies: rituximab (IgG1), rituximab-derived anti-human CD20 IgM+J as produced in Example 1, 1.5.3 (IgG1), 1.5.3 anti-CD20 IgM, or 1.5.3 anti-CD20 IgM+J, produced as described in Example 1.

The results are shown in FIG. 8A (rituximab and rituximab-like IgM) and FIG. 8B (1.5.3, 1.5.3 IgM+J, and huMAb-like IgM. In this experiment, the IgG and IgM versions were compared on a molar equivalent basis. The $IC_{50S}$ for the IgM versions were all about 30 to 40 times more effective at complement dependent cytotoxicity than the IgG versions.

(c) Next, the antibodies were then compared for CDC activity on different cell lines with decreasing CD20 expression levels. The assay was carried out with the following serially diluted antibodies: rituximab (IgG1), rituximab-derived anti-human CD20 IgM+J as produced in Example 1, 1.5.3 (IgG1), and 1.5.3 anti-CD20 IgM+J, produced as described in Example 1. The cells used were DoHH2 cells (DSMZ No. ACC 47), and Z138 cells (ATCC CRL-3001) were used in this assay. Z138 cells exhibit lower expression levels of CD20 than DoHH2 cells, as shown Table 4 below. The target cells were washed and resuspended in CDC assay medium (RPMI 1640, 10% heat-inactivated FBS) at a density of $1.0×10^6$ cells/mL and 10 µL/well was added to a Nunc 384-well tissue culture-treated white polystyrene plate. Serial 3-fold dilutions of test antibodies were prepared in assay medium, 10 µL/well was added to the assay plate, and the plate was incubated for 2 hr at 37° C. in a 5% $CO_2$ incubator to allow opsonization to occur. Normal human serum complement (Quidel) was frozen in aliquots, thawed once for use, diluted to 30% in assay medium, and 10 µL/well was added to the assay plate. The plate was incubated for 4 hr at 37° C. in a 5% $CO_2$ incubator. Cell Titer-Glo reagent (Promega) was thawed for use and 15 µL/well was added to the assay plate. The plate was gently mixed for 2 min on a plate shaker to lyse the cells and then for another 10 min at room temperature before measuring luminescence on an EnVision plate reader (Perkin-Elmer). After subtracting background signal, percent viability was plotted against antibody concentration and EC50 values were determined using GraphPad Prism.

The results are shown in FIG. 9 and in Table 3. On both cell lines, the IgM versions of the antibodies exhibited greater CDC killing than the IgG versions. On the lower CD20-expressing Z-138 cells, the CDC activity of the IgM versions were more than 100-fold improved relative to the IgG versions.

TABLE 3

CDC Activity Depends on CD20 Antigen Expression Level

| | EC$_{50}$ (nM) | |
|---|---|---|
| | DOHH-2 | Z-138 |
| Anti-CD20 IgG1 (rituximab) | 22 | >100 |
| 1.5.3 IgG | 4.6 | >100 |
| Anti-CD20 IgM + J | 0.09 | 0.41 |
| 1.5.3 IgM + J | 0.14 | 1.9 |

Example 3: Preparation of a Bispecific Anti-CD20 IgM Comprising a Modified J-Chain Binding CD3

Rituxan-like anti-human CD20 IgM and 1.5.3 anti-CD20 IgM were produced as described in Example 1.

Two different J-chain variants were constructed with distinct fusion sites incorporating variable regions from the anti-CD3 antibody visilizumab (Nuvion). Shown below are the sequences for two J-chains with the scFv corresponding to visilizumab (V) (VH-(GGGGS)$_3$-VL, double-underlined) fused to the J-chain (italics) through a (GGGGS)$_3$ linker (SEQ ID NO: 67, underlined) containing 15 amino acids in two different orientations—V15J and J15V. Each sequence contains an N-terminal signal peptide that is shown without underlining or italics. In certain aspects, other signal peptide sequences can be substituted for the signal peptides shown here.

```
SEQ ID NO: 63: precursor modified J-chain sequence
for V15J (DNA Sequence: SEQ ID NO: 68):
MGWSYIILFLVATATGVHSQVQLVQSGAEVKKPGASVKVSCKASGYTFIS

YTME1WVRQAPGQGLEWMGYINPRSGYTHYNQKLKDKATLTADKSASTAY

MELSSLRSEDTAVYYCARSAYYDYDGFAYWGQGTLVTVSSGGGGSGGGGS

GGGGSDIQMTQSPSSLSASVGDRVTITCSASSSVSYMNWYQQKPGKAPKR

LIYDTSKLASGVPSRFSGSGSGTDFTLTISSLQPEDFATYYCQQWSSNPP

TFGGGTKLEIKGGGGSGGGGSGGGGSQEDERIVLVDNKCKCARITSRIIR

SSEDPNEDIVERNIRIIVPLNNRENISDPTSPLRTRFVYHTSDLCKKCDP

TEVELDNQIVTATQSNICDEDSATETCYTYDRNKCYTAVVPLVYGGETKN

IVETATTPDACYPD

SEQ ID NO: 64: mature modified J-chain sequence
for V15J:
QVQLVQSGAEVKKPGASVKVSCKASGYTFISYTMHWVRQAPGQGLEWMGY

INPRSGYTHYNQKLKDKATLTADKSASTAYMELSSLRSEDTAVYYCARSA

YYDYDGFAYWGQGTLVTVSSGGGGSGGGGSGGGGSDIQMTQSPSSLSASV

GDRVTITCSASSSVSYMNWYQQKPGKAPKRLIYDTSKLASGVPSRFSGSG

SGTDFTLTISSLQPEDFATYYCQQWSSNPPTFGGGTKLEIKGGGGSGGGG

SGGGGSQEDERIVLVDNKCKCARITSRIIRSSEDPNEDIVERNIRIIVPL

NNRENISDPTSPLRTRFVYHLSDLCKKCDPTEVELDNQIVTATQSNICDE

DSATETCYTYDRNKCYTAVVPLVYGGETKNIVETALTPDACYPD

SEQ ID NO: 65: precursor modified J-chain sequence
for J15V (DNA sequence: SEQ ID NO: 69):
MKNHLLFWGVLAVFIKAVHVKAQEDERIVLVDNKCKCARITSRHRSSEDP

NEDIVERNIRIIVPLNNRENISDPTSPLRTRFVYHTSDLCKKCDPTEVEL

DNQIVTATQSNICDEDSATETCYTYDRNKCYTAVVPLVYGGETKMVETAL

TPDACYPDGGGGSGGGGSGGGGSQVQLVQSGAEVKKPGASVKVSCKASGY

TFISYTMHWVRQAPGQGLEWMGYINPRSGYTHYNQKLKDKATLTADKSAS

TAYMELSSLRSEDTAVYYCARSAYYDYDGFAYWGQGTLVTVSSGGGGSGG

GGSGGGGSDIQMTQSPSSLSASVGDRVTITCSASSSVSYMNWYQQKPGKA

PKRLIYDTSKLASGVPSRFSGSGSGTDFTLTISSLQPEDFATYYCQQWSS

NPPTFGGGTKLEIK

SEQ ID NO: 66: mature modified J-chain sequence
for J15V:
QEDERIVLVDNKCKCARITSRIIRSSEDPNEDIVERNIRIIVPLNNRENI

SDPTSPLRTRFVYHTSDLCKKCDPTEVELDNQIVTATQSNICDEDSATET

CYTYDRNKCYTAVVPLVYGGETKNIVETATTPDACYPDGGGGSGGGGSGG

GGSQVQLVQSGAEVKKPGASVKVSCKASGYTFISYTMHWVRQAPGQGLEW

MGYINPRSGYTHYNQKLKDKATLTADKSASTAYMELSSLRSEDTAVYYCA

RSAYYDYDGFAYWGQGTLVTVSSGGGGSGGGGSGGGGSDIQMTQSPSSLS

ASVGDRVTITCSASSSVSYMNWYQQKPGKAPKRLIYDTSKLASGVPSRFS

GSGSGTDFTLTISSLQPEDFATYYCQQWSSNPPTFGGGTKLEIK
```

The mature constructs each have a molecular weight of about 45 kD and can bind to soluble epsilon chain of CD3 (Sino Biological), or T-cells (data not shown).

The DNA constructs corresponding to the anti-CD20 heavy and light chains as well as those corresponding to either the wild-type (wt) J-chain, V15J or J15V J-chain sequences were cotransfected into mammalian cells, e.g., HEK293 or CHO cells, and proteins were expressed and purified according to standard methods. See, e.g., PCT Publication No. WO 2015/153912, which is incorporated herein by reference in its entirety. The J-chains fused to the anti-CD3 scFv with the 15 amino acid linker were able to incorporate with the anti-CD20 heavy and light chains to produce a pentameric form of bi-specific IgM.

Agarose-Acrylamide Hybrid Gel.

IgM Constructs were separated by non-reducing SDS-PAGE adapted from a previously described method (Chugai Seiyaki Kabushiki Kaisha, 2010, Pub. No.: US 2010/0172899 A1). Briefly, the hybrid gel was mixed with 40% Acrylamide/Bis-Acrylamide, 37.5:1 (Sigma-Aldrich) and Ultrapure Agarose (Invitrogen) to final concentrations of 3.6% and 0.5%, respectively, in 0.375 M Tris Buffer, pH 8.8 and 15% glycerol. The resulting mixture was heated to 50° C. and polymerization was initiated with the addition of 0.08% TEMED and 0.08% of ammonium persulfate. The resulting solution was poured between two plates and the acrylamide was allowed to polymerize at 37° C. for 1 hour and then left at room temperature for 30 min to ensure complete polymerization. Protein samples were loaded into the resulting hybrid gel and the gel was run in Tris-Acetate SDS Running Buffer (Novex) for 800 Vh. The gel was then fixed in 40% methanol, 10% acetic for 10 minutes, stained using a Colloidal Blue Staining Kit (Novex) for at least 3 hours and subsequently de-stained in water.

Non-Reducing SDS-Native-PAGE.

Protein samples were loaded into a NativePAGE 3-12% Bis-Tris gel (Novex). Tris-Acetate SDS Running Buffer (Novex) was added and the gel was run at 40V for 15 min and then at 90V for 2 hours. The gel was then fixed in 40% methanol, 10% acetic acid for 10 minutes, stained using a Colloidal Blue Staining Kit (Novex) for at least 3 hours and subsequently de-stained in water.

J-Chain Western Blot.

An acrylamide gel run under reducing conditions was washed in a 20% ethanol solution for 10 minutes and then the protein was transferred to an iBlot PVDF membrane (Invitrogen) using the iBlot Dry Blotting System (Invitrogen) at 20V for 10 minutes. After transfer the PVDF membrane was blocked using 2% bovine serum albumin, 0.05% Tween 20 for at least 12 hours. A ⅟₅₀₀ dilution of Pierce J-chain antibody (ThermoFisher) was added to the membrane, incubated for 1 hour, and then a ⅟₅₀₀₀ dilution of peroxidase-conjugated goat anti-rabbit IgG (Jackson ImmunoResearch) was added and allowed to incubate in darkness for 30 minutes. Finally, Super Signal West Pico Chemiluminescent Substrate (ThermoFisher) was added to the blot and the resulting signal was visualized using the ChemiDoc-It HR410 Imaging System (UVP) or by exposing the blot to X-ray film.

As shown in FIG. 10A and FIG. 10B, the 1.5.3 IgM+wt J and 1.5.3 IgM+V15J proteins are visible as faster migrating pentamers distinguishable on a hybrid gel from the slower migrating hexamer form not containing a J-chain. Integration of the J-chain is confirmed on the reducing gel (FIG. 10C) as well as western blot with antibodies to the J-chain (FIG. 10D).

Example 4: T-Cell Activation Assay

To demonstrate that a bispecific anti-CD20/anti-CD3 antibody could activate T-cells upon binding to the CD20 target the following assay was performed. Engineered Jurkat T-cells (Promega CS176403) and RPMI8226 cells (ATCC CCL-155) were cultured in RPMI (Invitrogen) supplemented with 10% Fetal Bovine Serum (Invitrogen). Serial dilutions of purified 1.5.3 IgM+V15J, Blinatumomab (bispecific CD19×CD3), and monospecific 1.5.3 IgM were incubated with 7500 RPMI8226 cells in 20 µL in a white 384 well assay plate for 2 h at 37° C. with 5% $CO_2$. The engineered Jurkat cells (25000) were added to mixture to final volume of 40 µL. The mixture was incubated for 5 h at 37° C. with 5% $CO_2$. The cell mixtures were then mixed with 20 µL lysis buffer containing luciferin (Promega, Cell Titer Glo) to measure luciferase reporter activity. Light output was measured by EnVision plate reader. EC50 was determined by 4 parameter curve fit using Prism software.

The results are shown in FIG. 11. T-cell activation with the 1.5.3-V15J antibody was greater than that seen with Blinatumomab on the RPMI8226 cell line. The maximal level of T-cell activation showed good correlation with the level of CD20 expression on cell surface as shown in FIG. 12 using a series of tumor cell lines each expressing a different level of CD20 antigen.

Example 5: T-Cell Directed B-Cell Killing—LDH Release Assay

In order to demonstrate that bispecific CD20×CD3 IgM binding molecules can kill target cells in the presence of CD8+ T-cell acute lymphoblastic leukemia (TALL) cells, we performed co-culture experiments. $6\times10^3$ cancerous B cells were co-cultured with $3\times10^4$ TALL cells (ATCC CRL-11386) in the presence of different concentrations of test compounds (Rituxan IgM+V15J and 1.5.3 IgM+V15J) in 45 µL total volume of RPMI 1640 media supplemented with 10% heat-inactivated FBS per well on a 384-well black tissue culture plate. After 24 hours of incubation at 37° C. in a 5% $CO_2$ incubator, 15 µL of CytoTox-ONE substrate reagent (Promega, G7891) was added to each well to measure the level of LDH released from dead cells. The plates were shaken briefly to mix the reagents, and then incubated at room temperature for 90 min before measuring fluorescence signal (485 nm for excitation and 615 nm for emission) on an EnVision plate reader (Perkin-Elmer). The data was then analyzed with GraphPad Prism to determine the $EC_{50}$. As shown Table 4, the $EC_{50}$ of cell killing correlated with the expression level of CD20 antigen on cell surface using both 1.5.3 IgM V15J and Rituximab IgM V15J with EC50 on DB cell line as low as 0.4 ng/mL (0.4 pM).

TABLE 4

T-cell Directed B-Cell Killing

| | | $EC_{50}$ (ng/mL) | |
|---|---|---|---|
| Cell lines | MFI | Rituxan IgM + V15J | IgM 1.5.3 + V15J |
| DB | 3400 | 0.5 | 0.4 |
| DOHH2 | 1300 | 13 | 12 |
| Z-138 | 800 | 30 | 33 |

Example 6: In Vitro Cytotoxicity Assay Using KILR™ Detection Kit

In order to examine the ability of 1.5.3 IgM+V15J to kill CD20+ tumor cells in whole blood (i.e., with the inclusion of T-cells and complement), the KILR™ in vitro cytotoxicity detection kit was used. The KILR™ ARH-77 cell line (CD20+) was purchased from DiscoverX (97-1001C017) as target cells. $5$-$10\times10^3$ KILR™ ARH-77 cells were co-cultured with either human CD8+ T-cells (Precision for Medicine), PBMC (AllCells or Precision for Medicine), or Hirudin anti-coagulated human blood (AllCells) in the presence of different concentrations of test compounds (1.5.3 IgM+V15J, 1.5.3 IgM+wtJ, 1.5.3 IgG, Rituximab IgG and blinatumomab) in 200 µL total volume of RPMI 1640 media supplemented with 10% heat-inactivated FBS (when human blood was used for co-culture, less media were used because the whole blood took up 20-50% of the volume) on a 96-well U-bottom non-tissue culture-treated polystyrene plate (Corning Falcon). After 4-48 hours of incubation at 37° C. in a 5% $CO_2$ incubator, the plates were centrifuged at 27×g for 5 min. 50 µL of the supernatants were transferred to a 96-well flat-bottom white polystyrene plate (Greiner Bio-One) to be mixed with 25 µL of KILR detection working solution (KILR™ detection kit: DiscoverX 97-0001M) for a 1-hour incubation at room temperature before measuring luminescence on an EnVision plate reader (Perkin-Elmer). The target cells were lysed with the lysis buffer supplied with the KILR™ detection kit to establish total lysis control. Percent killing was plotted against antibody concentration and EC50 values were determined using GraphPad Prism.

The results in the presence of normal human complement in whole blood (with hirudin) are shown in FIG. 13. The 1.5.3 IgM+wtJ (diamonds) and IgM+V15J (squares) antibodies both showed very potent killing at four hours. Rituxan IgG (open circles) and Blinatumomab (triangles) were at least 30 times less potent.

Example 7: In Vivo Efficacy Study Using Humanized NOD/SCID Gamma Knock-Out (NSG) Mouse Models CD34+ humanized NSG mouse studies were performed by In-Vivo Technologies, Inc. These mice are surrogates for human immuno-oncology studies, in that they possess develop multi-lineage human immune cells. The mice were purchased from the Jackson Laboratory, and dosed with test articles through tail vein injection. In addition to a vehicle control, the test articles included 1.5.3 IgM+V15J at 3 µg, 1 µg, and 0.3 µg per mouse and rituximab at 1 µg and 0.3 µg per mouse. Blood samples were collected at 6 h, 24 h, and 10 days post dose through facial vein. For the PBMC humanized NSG mouse studies, frozen PBMCs from All-Cells were sent to the Jackson Laboratory for injection. Each NSG mouse was injected with 10 million PBMCs after 100 cGy whole body irradiation. Blood samples were collected before and after tail vein dosing of test articles (as above) via retro-orbital bleeding at designated time points. Blood samples from both the CD34+ and PBMC mouse studies were sent back to IGM Biosciences Inc. for lymphocyte analysis. Blood samples were stained for human CD56, CD3, CD19 and CD45 markers to identify different population of human lymphocytes. CountBright Absolute Counting Beads (LifeTechnologies, C36950) were used to quantify the absolute number of lymphocytes in the blood samples. The lymphocyte levels were plotted and analyzed using GraphPad Prism.

Results at 6 hours post-dose for 1.5.3 IgM with wild-type J and 1.5.3 IgM with V15J, normalized to pre-dose B cell levels, are shown in FIG. 14A and FIG. 14B, respectively. The bispecific 1.5.3 IgM×V15J antibody showed potent T-cell dependent B-cell killing in the engrafted NSG mice with as little as 3 µg per mouse.

A comparison of the results over the full assay period between 1.5.3 IgM×V15J and rituximab are shown in FIG. 15.

TABLE 5

Sequences in the Disclosure

| SEQ ID NO | Short Name | Sequence |
|---|---|---|
| 1 | Rituximab VH | QVQLQQPGAELVKPGASVKMSCKASGYTFTSYNMHWVKQTPGRGLEWIGAIYPGNGDT SYNQKFKGKATLTADKSSSTAYMQLSSLTSEDSAVYYCARSTYYGGDWYFNVWGAGTT VTVSA |
| 2 | Rituximab HCDR1 | SYNMH |
| 3 | Rituximab HCDR2 | AIYPGNGDTSYNQKFKG |
| 4 | Rituximab HCDR3 | STYYGGDWYFNV |
| 5 | Rituximab VL | QIVLSQSPAILSASPGEKVTMTCRASSSVSYTHWFQQKPGSSPKPWIYATSNLASGVP VRFSGSGSGTSYSLTISRVEAEDAATYYCQQWTSNPPTFGGGTKLEIKR |
| 6 | Rituximab LCDR1 | RASSSVSYIH |
| 7 | Rituximab LCDR2 | ATSNLAS |
| 8 | Rituximab LCDR3 | QQWTSNPPT |
| 9 | 900 VH | EVQLVESGGG LVQPGGSLRL SCAASGYTFT SYNMHWVRQA PGKGLEWVGA IYPGNGDTSY NQKFKGRFTI SVDKSKNTLY LQMNSLRAED TAVYYCARVV YYSNSYWYFD VWGQGTLVTV SSASTKGPSV FPLAPSSKST SGGTAALGCL VKDYFPEPVT VSWNSGALTS GVHTFPAVLQ SSGLYSLSSV VTVPSSSLGT |
| 10 | 900HCDR3 | VVYYSNSYWY FDV |
| 11 | 900 VL | DIQMTQSPSS LSASVGDRVT ITCRASSSVS YMHWYQQKPG KAPKPLIYAP SNLASGVPSR FSGSGSGTDF TLTISSLQPE DFATYYCQQW SFNPPTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL |
| 12 | 900LCDR1 | RASSSVSYMH |
| 13 | 900LCDR2 | APSNLAS |
| 14 | 900LCDR3 | QQWSFNPPT |
| 15 | 125 VH | EVQLVQSGAEVKKPGESLKISCKGSGRTFTSYNMHWVRQMPGKGLEWMGAIYPLTGDT SYNQKSKLQVTISADKSISTAYLQWSSLKASDTAMYYCARSTYVGGDWQFDVWGKGTT VTVSS |
| 16 | 125HCDR2 | aiypltgdtsynqkskl |
| 17 | 125HCDR3 | styvggdwqfdv |
| 18 | 125 VL | EIVLTQSPGTLSLSPGERATLSCRASSSVPYIHWYQQKPGQAPRLLIYATSALASGIP DRFSGSGSGTDFTLTISRLEPEDFAVYYCQQWLSNPPTFGQGTKLEIK |
| 19 | 125LCDR1 | RASSSVPYIH |

TABLE 5-continued

Sequences in the Disclosure

| SEQ ID NO | Short Name | Sequence |
|---|---|---|
| 20 | 125LCDR2 | ATSALAS |
| 21 | 125LCDR3 | QQWLSNPPT |
| 22 | 844 VH #2 | QVQLQQPGAELKKPGASVKVSCKASGYTFTSYNMHWVKQTPGRGLEWTGAIYPGNGDT SYNQKFKGKTTLTADKSSSTAYMELSSLRSEDTAVYYCARSTYYGGDWYFNVWGAGTT VTVSA |
| 23 | 844 VH #3 | QVQLQQPGAELKKPGASVKVSCKASGYTFTSYNMHWVKQTPGRGLEWIGAIYPGNGDT SYNQKFKGKTTLTADKSSSTAYMELSSLRSEDTAVYYCARSTYYGGDWYFNVWGAGTT VTVSA |
| 24 | 844 VL #5 | QIVLSQSPAIITASPGEKVTMTCRASTSASYTHWFQQKPTSSPKPWIYATSNLASGVP SRFSGSGSGTTYSMTISSLEAEDAATYYCQQWTSNPPTFGGGTKLEIK |
| 25 | 844 VL #5 LCDR1 | RASTSASYIH |
| 26 | 844 VL #6 | QIVLSQSPAIITASPGEKVTMTCRASTSVSYIHWFQQKPTSSPKPWIYATSNLASGVP SRFSGSGSGTTYSMTISSLEAEDAATYYCQQWTSNPPTFGGGTKLEIK |
| 27 | 844 VL #6, #7 LCDR1 | RASTSVSYIH |
| 28 | 844 VL #7 | QIVLSQSPAIITASPGEKVTMTCRASTSVSYIHWFQQKPGSSPKPWIYATSNLASGVP SRFSGSGSGTTYSMTISSLEAEDAATYYCQQWTSNPPTFGGGTKLEIK |
| 27 | null | |
| 29 | 844 VL #8 | QIVLSQSPAIITASPGEKVTMTCRASSSVSYIHWFQQKPGSSPKPWIYATSNLASGVP SRFSGSGSGTTYSMTISSLEAEDAATYYCQQWTSNPPTFGGGTKLEIK |
| 30 | 844 VH #10 | EVQLQQSGAELKKPGASVKVSCKASGYTFTSYNMHWVKQTPGQGLEWIGAIYPGNGDT SYNQKFKGKTTLTADKSSSTAYMELSSLRSEDTAVYYCARSNYYGSSYWFFDVWGTGT TVTVSS |
| 31 | 844 VH #10 HCDR3 | SNYYGSSYWFFDV |
| 32 | 844 VL #12 | DIVLTQSPAIITASPGEKVTMTCRASSSVNYMDWYQKKPGSSPKPWIYATSNLASGVP SRFSGSGSGTTYSMTISSLEAEDAATYYCQQWSFNPPTFGGGTKLEIK |
| 33 | 844 VL #12 LCDR1 | RASSSVNYMD |
| 34 | 844 VL #12 LCDR3 | QQWSFNPPT |
| 35 | 164 VH | QVQLQQSGAEVKKPGSSVKVSCKASGYTFTSYNMHWVKQAPGQGLEWIGAIYPGNGDT SYNQKFKGKATLTADESTNTAYMELSSLRSEDTAFYYCARSTYYGGDWYFDVWGQGTT VTVSS |
| 36 | 164 VH HCDR3 | STYYGGDWYFDV |
| 37 | 164 VL | MGWSCIILFLVATATGVHSDIQLTQSPSSLSASVGDRVTMTCRASSSVSYIHWFQQKP GKAPKPWIYATSNLASGVPVRFSGSGSGTDYTFTISSLQPEDIATYYCQQWTSNPPTF GGGTKLEIK |
| 38 | 1.5.3 VH | EVQLVQSGAEVKKPGESLKISCKGSGYSFTSYWIGWVRQMPGKGLEWMGIIYPGDSDT RYSPSFQGQVTISADKSITTAYLQWSSLKASDTAMYYCARHPSYGSGSPNFDYWGQGT LVTVSS |
| 39 | 1.5.3 HCDR1 | GYSFTSYWIG |
| 40 | 1.5.3 HCDR2 | IIYPGDSDTRYSPSFQG |
| 41 | 1.5.3 HCDR3 | HPSYGSGSPNFDY |
| 42 | 1.5.3 VL | DIVMTQTPLSSPVTLGQPASISCRSSQSLVYSDGNTYLSWLQQRPGQPPRLLIYKISN RFSGVPDRFSGSGAGTDFTLKISRVEAEDVGVYYCVQATQFPLTFGGGTKVEIK |
| 43 | 1.5.3 LCDR1 | RSSQSLVYSDGNTYLS |
| 44 | 1.5.3 LCDR2 | KISNRFS |

TABLE 5-continued

Sequences in the Disclosure

| SEQ ID NO | Short Name | Sequence |
|---|---|---|
| 45 | 1.5.3 LCDR3 | VQATQFPLT |
| 46 | human IgM constant region DNA | GCCCCAACCCTTTTCCCCCTCGTCTCCTGTGAGAATTCCCCGTCGGATACGAGCAGCG<br>TGGCCGTTGGCTGCCTCGCACAGGACTTCCTTCCCGACTCCATCACTTTCTCCTGGAA<br>ATACAAGAACAACTCTGACATCAGCAGCACCCGGGGCTTCCCATCAGTCCTGAGAGGG<br>GGCAAGCACGCAGCCACCTCACAGGTGCTGCTGCCTTCCAAGGACGTCATGCAGGGCA<br>CAGACGAACACGTGGTGTGCAAAGTCCAGCACCCCAACGGCAACAAAGAAAAGAACGT<br>GCCTCTTCCAGTGATTGCTGAGCTGCCTCCCAAAGTGAGCGTCTTCGTCCCACCCCGC<br>GACGGCTTCTTCGGCAACCCCCGCAAGTCCAAGCTCATCTGCCAGGCCACGGGTTTCA<br>GTCCCCGGCAGATTCAGGTGTCCTGGCTGCGCGAGGGGAAGCAGGTGGGGTCTGGCGT<br>CACCACGGACCAGGTGCAGGCTGAGGCAAAGGAGTCTGGGACCACGACCTACAAGGTG<br>ACCAGCACACTGACCATCAAAGAGAGCGACTGGCTCAGCCAGAGCATGTTCACCTGCC<br>GCGTGGATCACAGGGGCCTGACCTTCCAGCAGAATGCGTCCTCCATGTGTGGCCCCGA<br>TCAAGACACAGCCATCCGGGTCTTCTCCATCCCCCCATCCTTTGCCAGCATCTTCCTC<br>ACCAAGTCCACCAAGTTGACCTGCCTGGTCACAGACCTGACCACCTATGACAGCGTGA<br>CCATCTCCTGGACCCGCCAGAATGGCGAAGCTGTGAAAACCCACACCAACATCTCCGA<br>GAGCCACCCCAATGCCACTTTCAGCGCCGTGGGTGAGGCCAGCATCTGCGAGGATGAC<br>TGGAATTCCGGGGAGAGGTTCACGTGCACCGTGACCCACACAGACCTGCCCTCGCCAC<br>TGAAGCAGACCATCTCCCGGCCCAAGGGGGTGGCCCTGCACAGGCCCGATGTCTACTT<br>GCTGCCACCAGCCCGGGAGCAGCTGAACCTGCGGGAGTCGGCCACCATCACGTGCCTG<br>GTGACGGGCTTCTCTCCCGCGGACGTCTTCGTGCAGTGGATGCAGAGGGGGCAGCCCT<br>TGTCCCCGGAGAAGTATGTGACCAGCGCCCCAATGCCTGAGCCCCAGGCCCCAGGCCG<br>GTACTTCGCCCACAGCATCCTGACCGTGTCCGAAGAGGAATGGAACACGGGGGAGACC<br>TACACCTGCGTGGTGGCCCATGAGGCCCTGCCCAACAGGGTCACCGAGAGGACCGTGG<br>ACAAGTCCACCGGTAAACCCACCCTGTACAACGTGTCCCTGGTCATGTCCGACACAGC<br>TGGCACCTGCTAC |
| 47 | human IgM constant region AA | GSASAPTLFPLVSCENSPSDTSSVAVGCLAQDFLPDSITFSWKYKNNSDISSTRGFPS<br>VLRGGKYAATSQVLLPSKDVMQGTDEHVVCKVQHPNGNKEKNVPLPVIAELPPKVSVF<br>VPPRDGFFGNPRKSKLICQATGFSPRQIQVSWLREGKQVGSGVTTDQVQAEAKESGPT<br>TYKVTSTLTIKESDWLSQSMFTCRVDHRGLTFQQNASSMCVPDQDTAIRVFAIPPSFA<br>SIFLTKSTKLTCLVTDLTTYDSVTISWTRQNGEAVKTHTNISESHPNATFSAVGEASI<br>CEDDWNSGERFTCTVTHTDLPSPLKQTISRPKGVALHRPDVYLLPPAREQLNLRESAT<br>ITCLVTGFSPADVFVQWMQRGQPLSPEKYVTSAPMPEPQAPGRYFAHSILTVSEEEWN<br>TGETYTCVVAHEALPNRVTERTVDKSTGKPTLYNVSLVMSDTAGTCY |
| 48 | J-chain DNA | ATGAAGAACCATTTGCTTTTCTGGGGAGTCCTGGCCGGTTTTTATTAAGGCTGTTCATG<br>TGAAAGCCCAAGAAGATGAAAGGATTGTTCTTGTTGACAACAAATGTAAGTGTGCCCG<br>GATTACTTCCAGGATCATCCGTTCTTCCGAAGATCCTAATGAGGACATTGTGGAGAGA<br>ACATCCGAATTATTGTTCCTCTGAACAACAGGGAGAATATCTCTGATCCCACCTCAC<br>CATTGAGAACCAGATTTGTGTACCATTTGTCTGACCTCTGTAAAAAATGTGATCCTAC<br>AGAAGTGGAGCTGGATAATCAGATAGTTACTGCTACCCAGAGCAATATCTGTGATGAA<br>GACAGTGCTACAGAGACCTGCTACACTTATGACAGAAACAAGTGCTACACAGCTGTGG<br>TCCCACTCGTATATGGTGGTGAGACCAAAATGGTGGAAACAGCCTTAACCCCAGATGC<br>CTGCTATCCTGACTAA |
| 49 | J-chain AA | mknhllfwgvlavfikavhvkagederivlvdnkckcaritsriirssedpnediver<br>niiivplnnrenisdptsplrtrfvyhlsdlckkcdpteveldnlivtatqsnicded<br>satetcytydrnkcytavvplvyggetkmvetaltpdacypd |
| 50 | human CD20 amino acid | MTTPRNSVNGTFPAEPMKGPIAMQSGPKPLFRRMSSLVGPTQSFFMRESKTLGAVQIM<br>NGLFHIALGGLLMIPAGIYAPICVTVWYPLWGGIMYIISGSLLAATEKNSRKCLVKGK<br>MIMNSLSLFAAISGMILSIMDILNIKISHFLKMESLNFIRAHTPYINIYNCEPANPSE<br>KNSPSTQYCYSIQSLFLGILSVMLIFAFFQELVIAGIVENEWKRTCSRPKSNIVLLSA<br>EEKKEQTIEIKEEVVGLTETSSQPKNEEDIETIPIQEEEEEETETNFPEPPQDQESSP<br>IENDSSP |
| 51 | Ritux-IgM heavy chain DNA | CAGGTTCAGCTGCAGCAGCCCGGAGCCGAGCTGGTCAAACCTGGCGCTAGTGTGAAAA<br>TGTCATGCAAGGCATCCGGATACACATTCACTAGCTATAACATGCACTGGGTGAAGCA<br>GACCCCCGGCAGGGGTCTGGAGTGGATCGGAGCTATCTACCCCGGCAACGGAGACACA<br>TCTTATAATCAGAAGTTTAAAGGCAAGGCCACCCTGACAGCTGATAAGTCCAGCTCTA<br>CCGCATACATGCAGCTGAGTTCACTGACAAGCGAGGACTCCGCCGTGTACTATTGCGC<br>CCGGTCCACTTACTATGGCGGAGATTGGTATTTCAATGTGTGGGGAGCAGGCACCACA<br>GTCACCGTCTCGAGCGGCAGTGCTAGCGCCCCAACCCTTTTCCCCCTCGTCTCCTGTG<br>AGAATTCCCCGTCGGATACGAGCAGCGTGGCCGTTGGCTGCCTCGCACAGGACTTCCT<br>TCCCGACTCCATCACTTTCTCCTGGAAATACAAGAACAACTCTGACATCAGCAGCACC<br>CGGGGCTTCCCATCAGTCCTGAGAGGGGCAAGTACGCAGCCACCTCACAGGTGCTGC<br>TGCCTTCCAAGGACGTCATGCAGGGCACAGACGAACACGTGGTGTGCAAAGTCCAGCA<br>CCCCAACGGCAACAAAGAAAAGAACGTGCCTCTTCCAGTGATTGCTGAGCTGCCTCCC<br>AAAGTGAGCGTCTTCGTCCCACCCCGCGACGGCTTCTTCGGCAACCCCCGCAAGTCCA<br>AGCTCATCTGCCAGGCCACGGGTTTCAGTCCCCGGCAGATTCAGGTGTCCTGGCTGCG<br>CGAGGGGAAGCAGGTGGGGTCTGGCGTCACCACGGACCAGGTGCAGGCTGAGGCCAAA<br>GAGTCTGGGCCCACGACCTACAAGGTGACCAGCACACTGACCATCAAAGAGAGCGACT<br>GGCTCAGCCAGAGCATGTTCACCTGCCGCGTGGATCACAGGGGCCTGACCTTCCAGCA<br>GAATGCGTCCTCCATGTGTGTCCCCGATCAAGACACAGCCATCCGGGTCTTCGCCATC |

TABLE 5-continued

Sequences in the Disclosure

| SEQ ID NO | Short Name | Sequence |
|---|---|---|
| | | CCCCCATCCTTTGCCAGCATCTTCCTCACCAAGTCCACCAAGTTGACCTGCCTGGTCA<br>CAGACCTGACCACCTATGACAGCGTGACCATCTCCTGGACCCGCCAGAATGGCGAAGC<br>TGTGAAAACCCACACCAACATCTCCGAGAGCCACCCCAATGCCACTTTCAGCGCCGTG<br>GGTGAGGCCAGCATCTGCGAGGATGACTGGAATTCCGGGGAGAGGTTCACGTGCACCG<br>TGACCCACACAGACCTGCCCTCGCCACTGAAGCAGACCATCTCCCGGCCCAAGGGGGT<br>GGCCCTGCACAGGCCCGATGTCTACTTGCTGCCACCAGCCCGGGAGCAGCTGAACCTG<br>CGGGAGTCGGCCACCATCACGTGCCTGGTGACGGGCTTCTCTCCCGCGGACGTCTTCG<br>TGCAGTGGATGCAGAGGGGGCAGCCCTTGTCCCCGGAGAAGTATGTGACCAGCGCCCC<br>AATGCCTGAGCCCCAGGCCCCAGGCCGGTACTTCGCCCACAGCATCCTGACCGTGTCC<br>GAAGAGGAATGGAACACGGGGGAGACCTACACCTGCGTGGTGGCCCATGAGGCCCTGC<br>CCAACAGGGTCACCGAGAGGACCGTGGACAAGTCCACCGGTAAACCCACCCTGTACAA<br>CGTGTGTCCCTGGTCATGTCCGACACAGCTGGCACCTGCTACTGA |
| 52 | Ritux-IgM<br>heavy chain | QVQLQQPGAELVKPGASVKMSCKASGYTFTSYNMHWVKQTPGRGLEWIGAIYPGNGDT<br>SYNQKFKGKATLTADKSSSTAYMQLSSLTSEDSAVYYCARSTYYGGDWYFNVWGAGTT<br>VTVSSGSASAPTLFPLVSCENSPSDTSSVAVGCLAQDFLPDSITFSWKYKNNSDISST<br>RGFPSVLRGGKYAATSQVLLPSKDVMQGTDEHVVCKVQHPNGNKEKNVPLPVIAELPP<br>KVSVFVPPRDGFFGNPRKSKLICQATGFSPRQIQVSWLREGKQVGSGVTTDQVQAEAK<br>ESGPTTYKVTSTLTIKESDWLSQSMFTCRVDHRGLTFQQNASSMCVPDQDTAIRVFAI<br>PPSFASIFLTKSTKLTCLVTDLTTYDSVTISWTRQNGEAVKTHTNISESHPNATFSAV<br>GEASICEDDWNSGERFTCTVTHTDLPSPLKQTISRPKGVALHRPDVYLLPPAREQLNL<br>RESATITCLVTGFSPADVFVQWMQRGQPLSPEKYVTSAPMPEPQAPGRYFAHSILTVS<br>EEEWNTGETYTCVVAHEALPNRVTERTVDKSTGKPTLYNVSLVMSDTAGTCY- |
| 53 | Ritux-light<br>chain DNA | CAAATTGTGCTGTCTCAGAGTCCAGCTATCCTGAGCGCATCTCCCGGAGAGAAGGTGA<br>CCATGACATGCAGAGCCTCCAGCTCTGTCTCCTACATCCACTGGTTCCAGCAGAAGCC<br>CGGCTCCTCCCCCAAAACCCTGGATCTACGCCACCTCTAACCTGGCTAGTGGTGTGCCT<br>GTCAGGTTTAGTGGATCAGGGTCCGGCACCAGCTACTCTCTGACAATCAGCCGGGTGG<br>AGGCTGAAGACGCCGCTACATACTATTGCCAGCAGTGGACTTCTAATCCCCCTACCTT<br>CGGCGGAGGGACAAAGCTGGAGATCAAG<u>CGT</u>ACGGTGGCTGCACCATCTGTCTTCATC<br>TTCCCGCCATCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGCCCTCCAATC<br>GGGTAACTCCCAGGAGAGTGTCACAGAGCAGGACAGCAAGGACAGCACCTACAGCCTC<br>AGCAGCACCCTGACGCTGAGCAAAGCAGACTACGAGAAACACAAAGTCTACGCCTGCG<br>AAGTCACCCATCAGGGCCTGAGCTCGCCCGTCACAAAGAGCTTCAACAGGGGAGAGTG<br><u>TTAG</u> |
| 54 | Ritux-light<br>chain AA | QIVLSQSPAILSASPGEKVTMTCRASSSVSYIHWFQQKPGSSPKPWIYATSNLASGVP<br>VRFSGSGSGTSYSLTISRVEAEDAATYYCQQWTSNPPTFGGGTKLEIKRTVAAPSVFI<br>FPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC- |
| 55 | 1.5.3 -IgM<br>heavy chain<br>DNA | GAGGTGCAGCTGGTGCAGTCCGGCGCCGAGGTGAAGAAGCCCGGCGAGTCCCTGAAGA<br>TCTCCTGCAAGGGCTCCGGCTACTCCTTCACCTCCTACTGGATCGGCTGGGTGAGGCA<br>GATGCCCGGCAAGGGCCTGGAGTGGATGGGCATCATCTACCCCGGCGACTCCGACACC<br>AGGTACTCCCCCTCCTTCCAGGGCCAGGTGACCATCTCCGCCGACAAGTCCATCACCA<br>CCGCCTACCTGCAGTGGTCCTCCCTGAAGGCCTCCGACACCGCCATGTACTACTGCGC<br>CAGGCACCCCTCCTACGGCTCCGGCTCCCCCAACTTCGACTACTGGGGCCAGGGCACC<br>CTGGTGACCGTGTCCTCCGGCAGTGCTAGCGCCCCAACCCTTTTCCCCCTCGTCTCCT<br>GTGAGAATTCCCCGTCGGATACGAGCAGCGTGGCCGTTGGCTGCCTCGCACAGGACTT<br>CCTTCCCGACTCCATCACTTTCTCCTGGAAATACAAGAACAACTCTGACATCAGCAGC<br>ACCCGGGGCTTCCCATCAGTCCTGAGAGGGGCAAGTACGCAGCCACCTCACAGGTGC<br>TGCTGCCTTCCAAGGACGTCATGCAGGGCACAGACGAACACGTGGTGTGCAAAGTCCA<br>GCACCCCAACGGCAACAAAGAAAAGAACGTGCCTCTTCCAGTGATTGCTGAGCTGCCT<br>CCCAAAGTGAGCGTCTTCGTCCCACCCCGCGACGGCTTCTTCGGCAACCCCCGCAAGT<br>CCAAGCTCATCTGCCAGGCCACGGGTTTCAGTCCCCGGCAGATTCAGGTGTCCTGGCT<br>GCGCGAGGGGAAGCAGGTGGGGTCTGGCGTCACCACGGACCAGGTGCAGGCTGAGGCC<br>AAAGAGTCTGGGCCCACGACCTACAAGGTGACCAGCACACTGACCATCAAAGAGAGCG<br>ACTGGCTCAGCCAGAGCATGTTCACCTGCCGCGTGGATCACAGGGGCCTGACCTTCCA<br>GCAGAATGCGTCCTCCATGTGTGTCCCCGATCAAGACACAGCCATCCGGGTCTTCGCC<br>ATCCCCCCATCCTTTGCCAGCATCTTCCTCACCAAGTCCACCAAGTTGACCTGCCTGG<br>TCACAGACCTGACCACCTATGACAGCGTGACCATCTCCTGGACCCGCCAGAATGGCGA<br>AGCTGTGAAAACCCACACCAACATCTCCGAGAGCCACCCCAATGCCACTTTCAGCGCC<br>GTGGGTGAGGCCAGCATCTGCGAGGATGACTGGAATTCCGGGGAGAGGTTCACGTGCA<br>CCGTGACCCACACAGACCTGCCCTCGCCACTGAAGCAGACCATCTCCCGGCCCAAGGG<br>GGTGGCCCTGCACAGGCCCGATGTCTACTTGCTGCCACCAGCCCGGGAGCAGCTGAAC<br>CTGCGGGAGTCGGCCACCATCACGTGCCTGGTGACGGGCTTCTCTCCCGCGGACGTCT<br>TCGTGCAGTGGATGCAGAGGGGGCAGCCCTTGTCCCCGGAGAAGTATGTGACCAGCGC<br>CCCAATGCCTGAGCCCCAGGCCCCAGGCCGGTACTTCGCCCACAGCATCCTGACCGTG<br>TCCGAAGAGGAATGGAACACGGGGGAGACCTACACCTGCGTGGTGGCCCATGAGGCCC<br>TGCCCAACAGGGTCACCGAGAGGACCGTGGACAAGTCCACCGGTAAACCCACCCTGTA<br>CAACGTGTGTCCCTGGTCATGTCCGACACAGCTGGCACCTGCTACTGA |
| 56 | 1.5.3 -IgM<br>heavy chain AA | EVQLVQSGAEVKKPGESLKISCKGSGYSFTSYWIGWVRQMPGKGLEWMGIIYPGDSDT<br>RYSPSFQGQVTISADKSITTAYLQWSSLKASDTAMYYCARHPSYGSGSPNFDYWGQGT<br>LVTVSSGSASAPTLFPLVSCENSPSDTSSVAVGCLAQDFLPDSITFSWKYKNNSDISS |

TABLE 5-continued

Sequences in the Disclosure

| SEQ ID NO | Short Name | Sequence |
|---|---|---|
| | | TRGFPSVLRGGKYAATSQVLLPSKDVMQGTDEHVVCKVQHPNGNKEKNVPLPVIAELP<br>PKVSVFVPPRDGFFGNPRKSKLICQATGFSPRQIQVSWLREGKQVGSGVTTDQVQAEA<br>KESGPTTYKVTSTLTIKESDWLSQSMFTCRVDHRGLTFQQNASSMCVPDQDTAIRVFA<br>IPPSFASIFLTKSTKLTCLVTDLTTYDSVTISWTRQNGEAVKTHTNISESHPNATFSA<br>VGEASICEDDWNSGERFTCTVTHTDLPSPLKQTISRPKGVALHRPDVYLLPPAREQLN<br>LRESATITCLVTGFSPADVFVQWMQRGQPLSPEKYVTSAPMPEPQAPGRYFAHSILTV<br>SEEEWNTGETYTCVVAHEALPNRVTERTVDKSTGKPTLYNVSLVMSDTAGTCY- |
| 57 | 1.5.3 light chain DNA | GACATCGTGATGACCCAGACCCCCCTGTCCTCCCCCGTGACCCTGGGCCAGCCCGCCT<br>CCATCTCCTGCAGGTCCTCCCAGTCCCTGGTGTACTCCGACGGCAACACCTACCTGTC<br>CTGGCTGCAGCAGAGGCCCGGCCAGCCCCCCAGGCTGCTGATCTACAAGATCTCCAAC<br>AGGTTCTCCGGCGTGCCCGACAGGTTCTCCGGCTCCGGCGCCGGCACCGACTTCACCC<br>TGAAGATCTCCAGGGTGGAGGCCGAGGACGTGGGCGTGTACTACTGCGTGCAGGCCAC<br>CCAGTTCCCCCTGACCTTCGGCGGCGGCACCAAGGTGGAGATCAAGCGTACGGTGGCT<br>GCACCATCTGTCTTCATCTTCCCGCCATCTGATGAGCAGTTGAAATCTGGAACTGCCT<br>CTGTTGTGTGCCTGCTGAATAACTTCTATCCCAGAGAGGCCAAAGTACAGTGGAAGGT<br>GGATAACGCCCTCCAATCGGGTAACTCCCAGGAGAGTGTCACAGAGCAGGACAGCAAG<br>GACAGCACCTACAGCCTCAGCAGCACCCTGACGCTGAGCAAAGCAGACTACGAGAAAC<br>ACAAAGTCTACGCCTGCGAAGTCACCCATCAGGGCCTGAGCTCGCCCGTCACAAAGAG<br>CTTCAACAGGGGAGAGTGTTAG |
| 58 | 1.5.3 light chain AA | DIVMTQTPLSSPVTLGQPASISCRSSQSLVYSDGNTYLSWLQQRPGQPPRLLIYKISN<br>RFSGVPDRFSGSGAGTDFTLKISRVEAEDVGVYYCVQATQFPLTFGGGTKVEIKRTVA<br>APSVFIFPPSDEQLKSGTASVVCLLNNFYPREAKVQWKVDNALQSGNSQESVTEQDSK<br>DSTYSLSSTLTLSKADYEKHKVYACEVTHQGLSSPVTKSFNRGEC- |
| 59 | human IgA1 constant region aa P01876 | ASPTSPKVFPLSLCSTQPDGNVVIACLVQGFFPQEPLSVTWSESGQGVTARNFPPSQD<br>ASGDLYTTSSQLTLPATQCLAGKSVTCHVKHYTNPSQDVTVPCPVPSTPPTPSPSTPP<br>TPSPSCCHPRLSLHRPALEDLLLGSEANLTCTLTGLRDASGVTFTWTPSSGKSAVQGP<br>PERDLCGCYSVSSVLPGCAEPWNHGKTFTCTAAYPESKTPTLATLSKSGNTFRPEVHL<br>LPPPSEELALNELVTLTCLARGFSPKDVLVRWLQGSQELPREKYLTWASRQEPSQGTT<br>TFAVTSILRVAAEDWKKGDTFSCMVGHEALPLAFTQKTIDRLAGKPTHVNVSVVMAEV<br>DGTCY |
| 60 | human IgA2 constant region aa P01877 | ASPTSPKVFPLSLDSTPQDGNVVACLVQGFFPQEPLSVTWSESGQNVTARNFPPSQD<br>ASGDLYTTSSQLTLPATQCPDGKSVTCHVKHYTNPSQDVTVPCPVPPPPCCHPRLSL<br>HRPALEDLLLGSEANLTCTLTGLRDASGATFTWTPSSGKSAVQGPPERDLCGCYSVSS<br>VLPGCAQPWNHGETFTCTAAHPELKTPLTANITKSGNTFRPEVHLLPPPSEELALNEL<br>VTLTCLARGFSPKDVLVRWLQGSQELPREKYLTWASRQEPSQGTTTFAVTSILRVAAE<br>DWKKGDTFSCMVGHEALPLAFTQKTIDRMAGKPTHVNVSVVMAEVDGTCY |
| 61 | Human Secretory Component Precursor | MLLFVLTCLLAVFPAISTKSPIFGPEEVNSVEGNSVSITCYYPPTSVNRHTRKYWCRQ<br>GARGGCITLISSEGYVSSKYAGRANLTNFPENGTFVVNIAQLSQDDSGRYKCGLGINS<br>RGLSFDVSLEVSQGPGLLNDTKVYTVDLGRTVTINCPFKTENAQKRKSLYKQIGLYPV<br>LVIDSSGYVNPNYTGRIRLDIQGTGQLLFSVVINQLRLSDAGQYLCQAGDDSNSNKKN<br>ADLQVLKPEPELVYEDLRGSVTFHCALGPEVANVAKFLCRQSSGENCDVVVNTLGKRA<br>PAFEGRILLNPQDKDGSFSVVITGLRKEDAGRYLCGAHSDGQLQEGSPIQAWQLFVNE<br>ESTIPRSPTVVKGVAGGSVAVLCPYNRKESKSIKYWCLWEGAQNGRCPLLVDSEGWVK<br>AQYEGRLSLLEEPGNGTFTVILNQLTSRDAGFYWCLTNGDTLWRTTVEIKIIEGEPNL<br>KVPGNVTAVLGETLKVPCHFPCKFSSYEKYWCKWNNTGCQALPSQDEGPSKAFVNCDE<br>NSRLVSLTLNLVTRADEGWYWCGVKQGHFYGETAAVYVAVEERKAAGSRDVSLAKADA<br>APDEKVLDSGFREIENKAIQDPRLFAEEKAVADTRDQADGSRASVDSGSSEEQGGSSR<br>ALVSTLVPLGLVLAVGAVAVGVARARHRKNVDRVSIRSYRTDISMSDFENSREFGAND<br>NMGASSITQETSLGGKEEFVATTESTTETKEPKKAKRSSKEEAEMAYKDFLLQSSTVA<br>AEAQDGPQEA |
| 62 | human secretory component mature | KSPIFGPEEVNSVEGNSVSITCYYPPTSVNRHTRKYWCRQGARGGCITLISSEGYVSS<br>KYAGRANLTNFPENGTFVVNIAQLSQDDSGRYKCGLGINSRGLSFDVSLEVSQGPGLL<br>NDTKVYTVDLGRTVTINCPFKTENAQKRKSLYKQIGLYPVLVIDSSGYVNPNYTGRIR<br>LDIQGTGQLLFSVVINQLRLSDAGQYLCQAGDDSNSNKKNADLQVLKPEPELVYEDLR<br>GSVTFHCALGPEVANVAKFLCRQSSGENCDVVVNTLGKRAPAFEGRILLNPQDKDGSF<br>SVVITGLRKEDAGRYLCGAHSDGQLQEGSPIQAWQLFVNEESTIPRSPTVVKGVAGGS<br>VAVLCPYNRKESKSIKYWCLWEGAQNGRCPLLVDSEGWVKAQYEGRLSLLEEPGNGTF<br>TVILNQLTSRDAGFYWCLTNGDTLWRTTVEIKIIEGEPNLKVPGNVTAVLGETLKVPC<br>HFPCKFSSYEKYWCKWNNTGCQALPSQDEGPSKAFVNCDENSRLVSLTLNLVTRADEG<br>WYWCGVKQGHFYGETAAVYVAVEERKAAGSRDVSLAKADAAPDEKVLDSGFREIENKA<br>IQDPR |
| 63 | precursor modified J-chain sequence for V15J | MGWSYIILFLVATATGVHSQVQLVQSGAEVKKPGASVKVSCKASGYTFISYTMHWVRQ<br>APGQGLEWMGYINPRSGYTHYNQKLKDKATLTADKSASTAYMELSSLRSEDTAVYYCA<br>RSAYYDYDGFAYWGQGTLVTVSSGGGGSGGGGSGGGGSDIQMTQSPSSLSASVGDRVT<br>ITCSASSSVSYMNWYQQKPGKAPKRLIYDTSKLASGVPSRFSGSGSGTDFTLTISSLQ<br>PEDFATYYCQQWSSNPPTFGGGTKLEIKGGGGSGGGGSGGGGSQEDERIVLVDNKCKC<br>ARITSRIIRSSEDPNEDIVERNIRIIVPLNNRENISDPTSPLRTRFVYHLSDLCKKCD<br>PTEVELDNQIVTATQSNICDEDSATETCYTYDRNKCYTAVVPLVYGGETKMVETALTP<br>DACYPD |

TABLE 5-continued

Sequences in the Disclosure

| SEQ ID NO | Short Name | Sequence |
|---|---|---|
| 64 | mature modified J-chain sequence for V15J | QVQLVQSGAEVKKPGASVKVSCKASGYTFISYTMHWVRQAPGQGLEWMGYINPRSGYT HYNQKLKDKATLTADKSASTAYMELSSLRSEDTAVYYCARSAYYDYDGFAYWGQGTLV TVSSGGGGSGGGGSGGGGSDIQMTQSPSSLSASVGDRVTITCSASSSVSYMNWYQQKP GKAPKRLIYDTSKLASGVPSRFSGSGSGTDFTLTISSLQPEDFATYYCQQWSSNPPTF GGGTKLEIKGGGGSGGGGSGGGGSQEDERIVLVDNKCKCARITSRIIRSSEDPNEDIV ERNIRIIVPLNNRENISDPTSPLRTRFVYHLSDLCKKCDPTEVELDNQIVTATQSNIC DEDSATETCYTYDRNKCYTAVVPLVYGGETKMVETALTPDACYPD |
| 65 | Precursor modified J-chain sequence for J15V | MKNHLLFWGVLAVFIKAVHVKAQEDERIVLVDNKCKCARITSRIIRSSEDPNEDIVER NIRIIVPLNNRENISDPTSPLRTRFVYHLSDLCKKCDPTEVELDNQIVTATQSNICDE DSATETCYTYDRNKCYTAVVPLVYGGETKMVETALTPDACYPDGGGGSGGGGSGGGGS QVQLVQSGAEVKKPGASVKVSCKASGYTFISYTMHWVRQAPGQGLEWMGYINPRSGYT HYNQKLKDKATLTADKSASTAYMELSSLRSEDTAVYYCARSAYYDYDGFAYWGQGTLV TVSSGGGGSGGGGSGGGGSDIQMTQSPSSLSASVGDRVTITCSASSSVSYMNWYQQKP GKAPKRLIYDTSKLASGVPSRFSGSGSGTDFTLTISSLQPEDFATYYCQQWSSNPPTF GGGTKLEIK |
| 66 | mature modified J-chain sequence for J15V | QEDERIVLVDNKCKCARITSRIIRSSEDPNEDIVERNIRIIVPLNNRENISDPTSPLR TRFVYHLSDLCKKCDPTEVELDNQIVTATQSNICDEDSATETCYTYDRNKCYTAVVPL VYGGETKMVETALTPDACYPDGGGGSGGGGSGGGGSQVQLVQSGAEVKKPGASVKVSC KASGYTFISYTMHWVRQAPGQGLEWMGYINPRSGYTHYNQKLKDKATLTADKSASTAY MELSSLRSEDTAVYYCARSAYYDYDGFAYWGQGTLVTVSSGGGGSGGGGSGGGGSDIQ MTQSPSSLSASVGDRVTITCSASSSVSYMNWYQQKPGKAPKRLIYDTSKLASGVPSRF SGSGSGTDFTLTISSLQPEDFATYYCQQWSSNPPTFGGGTKLEIK |
| 67 | (GGGGS)₃ linker | GGGGSGGGGSGGGGS |
| 68 | J-chain DNA sequence for V15J | ATGGGCTGGTCCTACATCATCCTCTTCCTCGTGGCCACAGCCACAGGCGTCCATAGCC AGGTGCAGCTGGTGCAGTCCGGCGCCGAAGTGAAGAAGCCTGGCGCCAGCGTGAAGGT GAGCTGCAAGGCTTCCGGCTACACCTTCATCTCCTACACCATGCACTGGGTGAGGCAA GCTCCTGGCCAGGGCCTGGAGTGGATGGGATACATCAACCCTCGGTCCGGCTATACCC ACTACAATCAGAAGCTGAAGGACAAGGCCACCCTGACCGCTGACAAGTCCGCCTCCAC CGCTTACATGGAGCTGTCCTCCCTGAGGTCCGAGGACACCGCCGTGTACTACTGTGCC AGGTCCGCCTACTACGACTACGACGGATTCGCTTACTGGGGCCAGGGCACCCTGGTGA CAGTGAGCTCCGGAGGAGGAGGCAGCGGCGGCGGCGGCAGCGGCGGCGGCGGCAGCGA TATCCAGATGACCCAGAGCCCTTCCAGCCTGTCCGCTTCCGTGGGCGACAGGGTGACC ATCACCTGCAGCGCTTCCTCCTCCGTGTCCTACATGAACTGGTACCAGCAGAAGCCTG GCAAGGCCCCCAAGAGGCTGATCTACGACACCTCCAAGCTGGCCTCCGGAGTGCCTTC CAGGTTCAGCGGCTCCGGCTCCGGAACCGACTTCACCCTGACCATTAGCTCCCTGCAG CCCGAGGACTTCGCCACCTACTACTGCCAGCAGTGGTCCAGCAACCCTCCCACCTTCG GCGGCGGCACAAAGCTGGAGATCAAGGGAGGAGGAGGATCCGGTGGTGGTGGTTCTGG CGGAGGTGGATCCAAGAAGATGAAAGGATTGTTCTTGTTGACAACAAATGTAAGTGT GCCCGGATTACTTCCAGGATCATCCGTTCTTCCGAAGATCCTAATGAGGACATTGTGG AGAGAAACATCCGAATTATTGTTCCTCTGAACAACAGGGAGAATATCTCTGATCCCAC CTCACCATTGAGAACCAGATTTGTGTACCATTTGTCTGACCTCTGTAAAAAATGTGAT CCTACAGAAGTGGAGCTGGATAATCAGATAGTTACTGCTACCCAGAGCAATATCTGTG ATGAAGACAGTGCTACAGAGACCTGCTACACTTATGACAGAAACAAGTGCTACACAGC TGTGGTCCCACTCGTATATGGTGGTGAGACCAAAATGGTGGAAACAGCCTTAACCCCA GATGCCTGCTATCCTGACTGA |
| 69 | J-chain DNA sequence for J15V | ATGAAGAACCATTTGCTTTTCTGGGGAGTCCTGGCGGTTTTTATTAAGGCTGTTCATG TGAAAGCCCAAGAAGATGAAAGGATTGTTCTTGTTGACAACAAATGTAAGTGTGCCCG GATTACTTCCAGGATCATCCGTTCTTCCGAAGATCCTAATGAGGACATTGTGGAGAGA AACATCCGAATTATTGTTCCTCTGAACAACAGGGAGAATATCTCTGATCCCACCTCAC CATTGAGAACCAGATTTGTGTACCATTTGTCTGACCTCTGTAAAAAATGTGATCCTAC AGAAGTGGAGCTGGATAATCAGATAGTTACTGCTACCCAGAGCAATATCTGTGATGAA GACAGTGCTACAGAGACCTGCTACACTTATGACAGAAACAAGTGCTACACAGCTGTGG TCCCACTCGTATATGGTGGTGAGACCAAAATGGTGGAAACAGCCTTAACCCCAGATGC CTGCTATCCTGACGGAGGAGGAGGATCCGGTGGTGGTGGTTCTGGCGGAGGTGGATCC CAGGTGCAGCTGGTGCAGTCCGGCGCCGAAGTGAAGAAGCCTGGCGCCAGCGTGAAGG TGAGCTGCAAGGCTTCCGGCTACACCTTCATCTCCTACACCATGCACTGGGTGAGGCA AGCTCCTGGCCAGGGCCTGGAGTGGATGGGATACATCAACCCTCGGTCCGGCTATACC CACTACAATCAGAAGCTGAAGGACAAGGCCACCCTGACCGCTGACAAGTCCGCCTCCA CCGCTTACATGGAGCTGTCCTCCCTGAGGTCCGAGGACACCGCCGTGTACTACTGTGC CAGGTCCGCCTACTACGACTACGACGGATTCGCTTACTGGGGCCAGGGCACCCTGGTG ACAGTGAGCTCCGGAGGAGGAGGCAGCGGTGGTGGCGGAAGCGGTGGAGGTGGCAGCG ATATCCAGATGACCCAGAGCCCTTCCAGCCTGTCCGCTTCCGTGGGCGACAGGGTGAC CATCACCTGCAGCGCTTCCTCCTCCGTGTCCTACATGAACTGGTACCAGCAGAAGCCT GGCAAGGCCCCCAAGAGGCTGATCTACGACACCTCCAAGCTGGCCTCCGGAGTGCCTT CCAGGTTCAGCGGCTCCGGCTCCGGAACCGACTTCACCCTGACCATTAGCTCCCTGCA GCCCGAGGACTTCGCCACCTACTACTGCCAGCAGTGGTCCAGCAACCCTCCCACCTTC GGAGGCGGCACAAAGCTGGAGATCAAGTGA |

The breadth and scope of the present disclosure should not be limited by any of the above-described exemplary embodiments but should be defined only in accordance with the following claims and their equivalents.

What is claimed is:

1. A dimeric or pentameric binding molecule comprising two or five bivalent binding units and a modified J-chain, wherein each binding unit comprises two heavy chain constant regions, each associated with an antigen-binding domain, wherein at least three antigen binding domains of the binding molecule are identical CD20 antigen binding domains comprising six immunoglobulin complementarity determining regions HCDR1, HCDR2, HCDR3, LCDR1, LCDR2, and LCDR3, wherein the HCDR1 comprises the amino acid sequence of SEQ ID NO: 39; the HCDR2 comprises the amino acid sequence of SEQ ID NO: 40; the HCDR3 comprises the amino acid sequence of SEQ ID NO: 41; the LCDR1 comprises the amino acid sequence of SEQ ID NO: 43; the LCDR2 comprises the amino acid sequence of SEQ ID NO: 44; and the LCDR3 comprises the amino acid sequence of SEQ ID NO: 45, wherein the modified J-chain comprises a J-chain and a heterologous polypeptide, wherein the heterologous polypeptide comprises an scFv fragment that can specifically bind to CD3E, wherein the heterologous polypeptide is directly or indirectly fused to the J-chain, and wherein the binding molecule can direct complement-mediated, T-cell-mediated, or both complement-mediated and T-cell-mediated killing of a CD20-expressing cell at higher potency than an equivalent amount of a monospecific, bivalent IgG1 antibody comprising a VH having the amino acid sequence SEQ ID NO: 38 and a VL having the amino acid sequence SEQ ID NO: 42.

2. The binding molecule of claim 1, which is a dimeric binding molecule comprising two bivalent IgA binding units or fragments thereof, wherein each binding unit comprises two IgA heavy chain constant regions each comprising at least a Cα3-tp domain, and each associated with an antigen-binding domain.

3. The binding molecule of claim 2, wherein the IgA heavy chain constant regions or fragments thereof each further comprise a Cα1 domain and a Cα2 domain.

4. The binding molecule of claim 1, which is a pentameric binding molecule comprising five bivalent IgM binding units, wherein each binding unit comprises two IgM heavy chain constant regions each comprising at least a Cµ4-tp domain and each associated with an antigen-binding domain.

5. The binding molecule of claim 4, wherein the IgM heavy chain constant regions further comprise a Cµ3 domain, a Cµ2 domain, a Cµ1 domain, or any combination thereof.

6. The binding molecule of claim 1, wherein the J-chain comprises the amino acid sequence SEQ ID NO: 49.

7. The binding molecule of claim 1, wherein the heterologous polypeptide is fused to the J-chain via a peptide linker, wherein the peptide linker comprises at least 5 amino acids, but no more than 25 amino acids, and wherein the heterologous polypeptide is fused to the N-terminus of the J-chain, the C-terminus of the J-chain, or to both the N-terminus and C-terminus of the J-chain.

8. The binding molecule of claim 1, wherein the modified J-chain comprises the amino acid sequence SEQ ID NO: 64 (V15J) or SEQ ID NO: 66 (J15V).

9. The binding molecule of claim 5, wherein the IgM heavy chain constant regions are human IgM constant regions, and wherein each binding unit comprises two identical IgM heavy chains each comprising a VH situated amino terminal to the IgM constant region, and two identical immunoglobulin light chains each comprising a VL situated amino terminal to an immunoglobulin light chain constant region.

10. The binding molecule of claim 9, wherein each IgM heavy chain comprises the amino acid sequence SEQ ID NO: 56, and wherein each light chain comprises the amino acid sequence SEQ ID NO: 58.

11. The binding molecule of claim 1, wherein the CD20-expressing cell is a lymphoma cell line.

12. The binding molecule of claim 1, wherein the CD20-expressing cell is a malignant B cell in a subject with cancer.

13. The binding molecule of claim 12, wherein the cancer is minimally responsive or non-responsive to rituximab therapy.

14. The binding molecule of claim 12, wherein the subject is human.

15. A composition comprising the binding molecule claim 1, and a carrier.

16. The binding molecule of claim 1, wherein the at least three identical CD20 antigen binding domains each comprise an antibody heavy chain variable region (VH) and an antibody light chain variable region (VL), wherein the VH comprises an amino acid sequence at least at least 90% identical to SEQ ID NO: 38, and the VL comprises an amino acid sequence at least 90% identical to SEQ ID NO: 42.

17. The binding molecule of claim 16, wherein the VH comprises the amino acid sequence of SEQ ID NO: 38 and the VL comprises the amino acid sequence of SEQ ID NO: 42.

18. The binding molecule of claim 8, wherein the IgM heavy chain constant regions are human IgM constant regions, and wherein each binding unit comprises two identical IgM heavy chains each comprising a VH situated amino terminal to the IgM constant region, and two identical immunoglobulin light chains each comprising a VL situated amino terminal to an immunoglobulin light chain constant region.

19. The binding molecule of claim 18, wherein each IgM heavy chain comprises the amino acid sequence SEQ ID NO: 56, and wherein each light chain comprises the amino acid sequence SEQ ID NO: 58.

20. The binding molecule of claim 16, wherein the heterologous polypeptide is fused to the J-chain via a peptide linker, wherein the peptide linker comprises at least 5 amino acids, but no more than 25 amino acids, and wherein the heterologous polypeptide is fused to the N-terminus of the J-chain, the C-terminus of the J-chain, or to both the N-terminus and C-terminus of the J-chain.

21. The binding molecule of claim 16, wherein the modified J-chain comprises the amino acid sequence SEQ ID NO: 64 (V15J) or SEQ ID NO: 66 (J15V).

22. The binding molecule of claim 17, wherein the heterologous polypeptide is fused to the J-chain via a peptide linker, wherein the peptide linker comprises at least 5 amino acids, but no more than 25 amino acids, and wherein the heterologous polypeptide is fused to the N-terminus of the J-chain, the C-terminus of the J-chain, or to both the N-terminus and C-terminus of the J-chain.

23. The binding molecule of claim 17, wherein the modified J-chain comprises the amino acid sequence SEQ ID NO: 64 (V15J) or SEQ ID NO: 66 (J15V).

24. The binding molecule of claim 4, wherein the at least three identical CD20 antigen binding domains each comprise an antibody heavy chain variable region (VH) and an antibody light chain variable region (VL), wherein the VH comprises an amino acid sequence at least at least 90% identical to SEQ ID NO: 38, and the VL comprises an amino acid sequence at least 90% identical to SEQ ID NO: 42.

25. The binding molecule of claim 4, wherein the VH comprises the amino acid sequence of SEQ ID NO: 38 and the VL comprises the amino acid sequence of SEQ ID NO: 42.

26. The binding molecule of claim 25, wherein the heterologous polypeptide is fused to the J-chain via a peptide linker, wherein the peptide linker comprises at least 5 amino acids, but no more than 25 amino acids, and wherein the heterologous polypeptide is fused to the N-terminus of the J-chain, the C-terminus of the J-chain, or to both the N-terminus and C-terminus of the J-chain.

27. The binding molecule of claim 25, wherein the modified J-chain comprises the amino acid sequence SEQ ID NO: 64 (V15J) or SEQ ID NO: 66 (J15V).

28. The binding molecule of claim 5, wherein the at least three identical CD20 antigen binding domains each comprise an antibody heavy chain variable region (VH) and an antibody light chain variable region (VL), wherein the VH comprises an amino acid sequence at least at least 90% identical to SEQ ID NO: 38, and the VL comprises an amino acid sequence at least 90% identical to SEQ ID NO: 42.

29. The binding molecule of claim 5, wherein the VH comprises the amino acid sequence of SEQ ID NO: 38 and the VL comprises the amino acid sequence of SEQ ID NO: 42.

30. The binding molecule of claim 29, wherein the heterologous polypeptide is fused to the J-chain via a peptide linker, wherein the peptide linker comprises at least 5 amino acids, but no more than 25 amino acids, and wherein the heterologous polypeptide is fused to the N-terminus of the J-chain, the C-terminus of the J-chain, or to both the N-terminus and C-terminus of the J-chain.

31. The binding molecule of claim 29, wherein the modified J-chain comprises the amino acid sequence SEQ ID NO: 64 (V15J) or SEQ ID NO: 66 (J15V).

* * * * *

UNITED STATES PATENT AND TRADEMARK OFFICE
CERTIFICATE OF CORRECTION

PATENT NO. : 10,787,520 B2
APPLICATION NO. : 15/554301
DATED : September 29, 2020
INVENTOR(S) : Bruce Alan Keyt et al.

It is certified that error appears in the above-identified patent and that said Letters Patent is hereby corrected as shown below:

In the Claims

Column 132, Line 57, Claim 1, replace "bind to CD3E, wherein" with --bind to CD3ε, wherein--

Signed and Sealed this
Fifth Day of January, 2021

Andrei Iancu
*Director of the United States Patent and Trademark Office*

```
                         SEQUENCE LISTING

<160> NUMBER OF SEQ ID NOS: 69

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Asn Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Tyr Pro Gly Asn Gly Asp Thr Ser Tyr Asn Gln Lys Phe Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Ser Thr Tyr Tyr Gly Gly Asp Trp Tyr Phe Asn Val
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Ser Ser Val Ser Tyr Ile His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Thr Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Trp Thr Ser Asn Pro Pro Thr
1               5
```

<210> SEQ ID NO 9
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr
        195                 200

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Val Tyr Tyr Ser Asn Ser Tyr Trp Tyr Phe Asp Val
1               5                   10

<210> SEQ ID NO 11
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met

```
                    20                  25                  30
His Trp Tyr Gln Gln Lys Pro Gly Lys Ala Pro Lys Pro Leu Ile Tyr
                35                  40                  45
Ala Pro Ser Asn Leu Ala Ser Gly Val Pro Ser Arg Phe Ser Gly Ser
            50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Trp Ser Phe Asn Pro Pro Thr
                85                  90                  95
Phe Gly Gln Gly Thr Lys Val Glu Ile Lys Arg Thr Val Ala Ala Pro
                100                 105                 110
Ser Val Phe Ile Phe Pro Pro Ser Asp Glu Gln Leu Lys Ser Gly Thr
                115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
                180                 185                 190
Cys Glu Val Thr His Gln Gly Leu
            195                 200

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Ser Ser Val Ser Tyr Met His
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Pro Ser Asn Leu Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Trp Ser Phe Asn Pro Pro Thr
1               5

<210> SEQ ID NO 15
```

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
            20                  25                  30

Asn Met His Trp Val Arg Gln Met Pro Gly Lys Gly Leu Glu Trp Met
        35                  40                  45

Gly Ala Ile Tyr Pro Leu Thr Gly Asp Thr Ser Tyr Asn Gln Lys Ser
    50                  55                  60

Lys Leu Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser
        115                 120

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ile Tyr Pro Leu Thr Gly Asp Thr Ser Tyr Asn Gln Lys Ser Lys
1               5                   10                  15

Leu

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Thr Tyr Val Gly Gly Asp Trp Gln Phe Asp Val
1               5                   10

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Pro Tyr Ile
            20                  25                  30
```

```
His Trp Tyr Gln Gln Lys Pro Gly Gln Ala Pro Arg Leu Leu Ile Tyr
            35                  40                  45

Ala Thr Ser Ala Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Leu Ser Asn Pro Pro Thr
                 85                  90                  95

Phe Gly Gln Gly Thr Lys Leu Glu Ile Lys
            100                 105

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Ser Ser Ser Val Pro Tyr Ile His
 1               5                  10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Thr Ser Ala Leu Ala Ser
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Trp Leu Ser Asn Pro Pro Thr
 1               5

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Pro Gly Ala Glu Leu Lys Lys Pro Gly Ala
 1               5                  10                  15

Ser Val Lys Val Ser Cys Lys Ala Ser Gly Tyr Thr Phe Thr Ser Tyr
                 20                  25                  30

Asn Met His Trp Val Lys Gln Thr Pro Gly Arg Gly Leu Glu Trp Thr
            35                  40                  45

Gly Ala Ile Tyr Pro Gly Asn Gly Asp Thr Ser Tyr Asn Gln Lys Phe
```

```
                 50                  55                  60
Lys Gly Lys Thr Thr Leu Thr Ala Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala
            115                 120

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Pro Gly Ala Glu Leu Lys Lys Pro Gly Ala
 1               5                  10                  15

Ser Val Lys Val Ser Cys Lys Ala Ser Gly Tyr Thr Phe Thr Ser Tyr
                 20                  25                  30

Asn Met His Trp Val Lys Gln Thr Pro Gly Arg Gly Leu Glu Trp Ile
             35                  40                  45

Gly Ala Ile Tyr Pro Gly Asn Gly Asp Thr Ser Tyr Asn Gln Lys Phe
 50                  55                  60

Lys Gly Lys Thr Thr Leu Thr Ala Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala
            115                 120

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Val Leu Ser Gln Ser Pro Ala Ile Ile Thr Ala Ser Pro Gly
 1               5                  10                  15

Glu Lys Val Thr Met Thr Cys Arg Ala Ser Thr Ser Ala Ser Tyr Ile
                 20                  25                  30

His Trp Phe Gln Gln Lys Pro Thr Ser Ser Pro Lys Pro Trp Ile Tyr
             35                  40                  45

Ala Thr Ser Asn Leu Ala Ser Gly Val Pro Ser Arg Phe Ser Gly Ser
 50                  55                  60

Gly Ser Gly Thr Thr Tyr Ser Met Thr Ile Ser Ser Leu Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
```

```
                    100                 105

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Thr Ser Ala Ser Tyr Ile His
1               5                   10

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Val Ser Tyr Ile
                20                  25                  30

His Trp Phe Gln Gln Lys Pro Thr Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ala Ser Thr Ser Val Ser Tyr Ile His
1               5                   10

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ile Val Leu Ser Gln Ser Pro Ala Ile Ile Thr Ala Ser Pro Gly
1               5                   10                  15

Glu Lys Val Thr Met Thr Cys Arg Ala Ser Thr Ser Val Ser Tyr Ile
                20                  25                  30
```

His Trp Phe Gln Gln Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
 50                  55                  60

Gly Ser Gly Thr Thr Tyr Ser Met Thr Ile Ser Ser Leu Glu Ala Glu
65                   70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ile Val Leu Ser Gln Ser Pro Ala Ile Ile Thr Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
 50                  55                  60

Gly Ser Gly Thr Thr Tyr Ser Met Thr Ile Ser Ser Leu Glu Ala Glu
65                   70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105

<210> SEQ ID NO 30
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Gln Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
 50                  55                  60

Lys Gly Lys Thr Thr Leu Thr Ala Asp Lys Ser Ser Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Ser Asn Tyr Tyr Gly Ser Ser Tyr Trp Phe Phe Asp Val Trp
            100                 105                 110

Gly Thr Gly Thr Thr Val Thr Val Ser Ser
            115                 120

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Asn Tyr Tyr Gly Ser Ser Tyr Trp Phe Phe Asp Val
1               5                   10

<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Leu Thr Gln Ser Pro Ala Ile Ile Thr Ala Ser Pro Gly
1               5                   10                  15

Glu Lys Val Thr Met Thr Cys Arg Ala Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys
            100                 105

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Ser Ser Val Asn Tyr Met Asp
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Trp Ser Phe Asn Pro Pro Thr
1               5

<210> SEQ ID NO 35

<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Gln Val Gln Leu Gln Gln Ser Gly Ala Glu Val Lys Lys Pro Gly Ser
1               5                   10                  15
Ser Val Lys Val Ser Cys Lys Ala Ser Gly Tyr Thr Phe Thr Ser Tyr
            20                  25                  30
Asn Met His Trp Val Lys Gln Ala Pro Gly Gln Gly Leu Glu Trp Ile
        35                  40                  45
Gly Ala Ile Tyr Pro Gly Asn Gly Asp Thr Ser Tyr Asn Gln Lys Phe
    50                  55                  60
Lys Gly Lys Ala Thr Leu Thr Ala Asp Glu Ser Thr Asn Thr Ala Tyr
65                  70                  75                  80
Met Glu Leu Ser Ser Leu Arg Ser Glu Asp Thr Ala Phe Tyr Tyr Cys
                85                  90                  95
Ala Arg Ser Thr Tyr Tyr Gly Gly Asp Trp Tyr Phe Asp Val Trp Gly
            100                 105                 110
Gln Gly Thr Thr Val Thr Val Ser Ser
        115                 120

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Thr Tyr Tyr Gly Gly Asp Trp Tyr Phe Asp Val
1               5                   10

<210> SEQ ID NO 37
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Met Gly Trp Ser Cys Ile Ile Leu Phe Leu Val Ala Thr Ala Thr Gly
1               5                   10                  15
Val His Ser Asp Ile Gln Leu Thr Gln Ser Pro Ser Ser Leu Ser Ala
            20                  25                  30
Ser Val Gly Asp Arg Val Thr Met Thr Cys Arg Ala Ser Ser Ser Val
        35                  40                  45
Ser Tyr Ile His Trp Phe Gln Gln Lys Pro Gly Lys Ala Pro Lys Pro
    50                  55                  60
Trp Ile Tyr Ala Thr Ser Asn Leu Ala Ser Gly Val Pro Val Arg Phe
65                  70                  75                  80
Ser Gly Ser Gly Ser Gly Thr Asp Tyr Thr Phe Thr Ile Ser Ser Leu
                85                  90                  95
Gln Pro Glu Asp Ile Ala Thr Tyr Tyr Cys Gln Gln Trp Thr Ser Asn
            100                 105                 110

```
Pro Pro Thr Phe Gly Gly Gly Thr Lys Leu Glu Ile Lys
        115                 120                 125
```

<210> SEQ ID NO 38
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Gly Ser Pro Asn Phe Asp Tyr Trp
            100                 105                 110

Gly Gln Gly Thr Leu Val Thr Val Ser Ser
        115                 120
```

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Gly Tyr Ser Phe Thr Ser Tyr Trp Ile Gly
1               5                   10
```

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ile Ile Tyr Pro Gly Asp Ser Asp Thr Arg Tyr Ser Pro Ser Phe Gln
1               5                   10                  15

Gly
```

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
His Pro Ser Tyr Gly Ser Gly Ser Pro Asn Phe Asp Tyr
1               5                   10
```

<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr Gln Phe Pro Leu Thr Phe Gly Gly Gly Thr Lys Val Glu Ile Lys
            100                 105                 110
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Arg Ser Ser Gln Ser Leu Val Tyr Ser Asp Gly Asn Thr Tyr Leu Ser
1               5                   10                  15
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Lys Ile Ser Asn Arg Phe Ser
1               5
```

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Val Gln Ala Thr Gln Phe Pro Leu Thr
1               5
```

<210> SEQ ID NO 46

<211> LENGTH: 1347
<212> TYPE: DNA
<213> ORGANISM: Homo sapiens

<400> SEQUENCE: 46

```
gccccaaccc tttccccct cgtctcctgt gagaattccc cgtcggatac gagcagcgtg      60
gccgttggct gcctcgcaca ggacttcctt cccgactcca tcactttctc ctggaaatac     120
aagaacaact ctgacatcag cagcacccgg ggcttcccat cagtcctgag aggggggcaag   180
cacgcagcca cctcacaggt gctgctgcct tccaaggacg tcatgcaggg cacagacgaa    240
cacgtggtgt gcaaagtcca gcaccccaac ggcaacaaag aaaagaacgt gcctcttcca    300
gtgattgctg agctgcctcc caagtgagc gtcttcgtcc accccgcga cggcttcttc       360
ggcaaccccc gcaagtccaa gctcatctgc caggccacgg gtttcagtcc ccggcagatt     420
caggtgtcct ggctgcgcga ggggaagcag gtggggtctg cgtcaccac ggaccaggtg     480
caggctgagg caaaggagtc tgggaccacg acctacaagg tgaccagcac actgaccatc    540
aaagagagcg actggctcag ccagagcatg ttcacctgcc gcgtggatca caggggcctg    600
accttccagc agaatgcgtc ctccatgtgt ggccccgatc aagacacagc catccgggtc    660
ttctccatcc cccatccttt tgccagcatc ttcctcacca gtccaccaa gttgacctgc     720
ctggtcacag acctgaccac ctatgacagc gtgaccatct cctggacccg ccagaatggc   780
gaagctgtga aaaccccacac caacatctcc gagagccacc ccaatgccac tttcagcgcc   840
gtgggtgagg ccagcatctg cgaggatgac tggaattccg gggagaggtt cacgtgcacc   900
gtgacccaca cagacctgcc ctcgccactg aagcagacca tctcccggcc caaggggggtg   960
gccctgcaca ggcccgatgt ctacttgctg ccaccagccc gggagcagct gaacctgcgg   1020
gagtcggcca ccatcacgtg cctggtgacg ggcttctctc ccgcggacgt cttcgtgcag   1080
tggatgcaga gggggcagcc cttgtccccg gagaagtatg tgaccagcgc cccaatgcct   1140
gagccccagg ccccaggccg gtacttcgcc cacagcatcc tgaccgtgtc cgaagaggaa   1200
tggaacacgg gggagaccta cacctgcgtg gtggcccatg aggccctgcc caacagggtc   1260
accgagagga ccgtggacaa gtccaccggt aaacccaccc tgtacaacgt gtccctggtc   1320
atgtccgaca cagctggcac ctgctac                                        1347
```

<210> SEQ ID NO 47
<211> LENGTH: 453
<212> TYPE: PRT
<213> ORGANISM: Homo sapiens

<400> SEQUENCE: 47

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
        50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
```

```
                100             105             110
Val Ser Val Phe Val Pro Pro Arg Asp Gly Phe Phe Gly Asn Pro Arg
            115             120             125

Lys Ser Lys Leu Ile Cys Gln Ala Thr Gly Phe Ser Pro Arg Gln Ile
130             135             140

Gln Val Ser Trp Leu Arg Glu Gly Lys Gln Val Gly Ser Gly Val Thr
145             150             155             160

Thr Asp Gln Val Gln Ala Glu Ala Lys Glu Ser Gly Pro Thr Thr Tyr
            165             170             175

Lys Val Thr Ser Thr Leu Thr Ile Lys Glu Ser Asp Trp Leu Ser Gln
            180             185             190

Ser Met Phe Thr Cys Arg Val Asp His Arg Gly Leu Thr Phe Gln Gln
            195             200             205

Asn Ala Ser Ser Met Cys Val Pro Asp Gln Asp Thr Ala Ile Arg Val
            210             215             220

Phe Ala Ile Pro Pro Ser Phe Ala Ser Ile Phe Leu Thr Lys Ser Thr
225             230             235             240

Lys Leu Thr Cys Leu Val Thr Asp Leu Thr Thr Tyr Asp Ser Val Thr
            245             250             255

Ile Ser Trp Thr Arg Gln Asn Gly Glu Ala Val Lys Thr His Thr Asn
            260             265             270

Ile Ser Glu Ser His Pro Asn Ala Thr Phe Ser Ala Val Gly Glu Ala
            275             280             285

Ser Ile Cys Glu Asp Asp Trp Asn Ser Gly Glu Arg Phe Thr Cys Thr
290             295             300

Val Thr His Thr Asp Leu Pro Ser Pro Leu Lys Gln Thr Ile Ser Arg
305             310             315             320

Pro Lys Gly Val Ala Leu His Arg Pro Asp Val Tyr Leu Leu Pro Pro
            325             330             335

Ala Arg Glu Gln Leu Asn Leu Arg Glu Ser Ala Thr Ile Thr Cys Leu
            340             345             350

Val Thr Gly Phe Ser Pro Ala Asp Val Phe Val Gln Trp Met Gln Arg
            355             360             365

Gly Gln Pro Leu Ser Pro Glu Lys Tyr Val Thr Ser Ala Pro Met Pro
370             375             380

Glu Pro Gln Ala Pro Gly Arg Tyr Phe Ala His Ser Ile Leu Thr Val
385             390             395             400

Ser Glu Glu Glu Trp Asn Thr Gly Glu Thr Tyr Thr Cys Val Val Ala
            405             410             415

His Glu Ala Leu Pro Asn Arg Val Thr Glu Arg Thr Val Asp Lys Ser
            420             425             430

Thr Gly Lys Pro Thr Leu Tyr Asn Val Ser Leu Val Met Ser Asp Thr
            435             440             445

Ala Gly Thr Cys Tyr
        450

<210> SEQ ID NO 48
<211> LENGTH: 480
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
```

```
atgaagaacc atttgctttt ctggggagtc ctggcggttt ttattaaggc tgttcatgtg    60
aaagcccaag aagatgaaag gattgttctt gttgacaaca aatgtaagtg tgcccggatt   120
acttccagga tcatccgttc ttccgaagat cctaatgagg acattgtgga gagaaacatc   180
cgaattattg ttcctctgaa caacagggag aatatctctg atccacctc accattgaga    240 accagatttg tgtaccattt gtctgacctc tgtaaaaaat gtgatcctac agaagtggag   300
ctggataatc agatagttac tgctacccag agcaatatct gtgatgaaga cagtgctaca   360
gagacctgct acacttatga cagaaacaag tgctacacag ctgtggtccc actcgtatat   420
ggtggtgaga ccaaaatggt ggaaacagcc ttaaccccag atgcctgcta tcctgactaa   480
```

<210> SEQ ID NO 49
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Ile Ile Val Pro
        50                  55                  60

Leu Asn Asn Arg Glu Asn Ile Ser Asp Pro Thr Ser Pro Leu Arg Thr
65                  70                  75                  80

Arg Phe Val Tyr His Leu Ser Asp Leu Cys Lys Cys Asp Pro Thr
                85                  90                  95

Glu Val Glu Leu Asp Asn Gln Ile Val Thr Ala Thr Gln Ser Asn Ile
            100                 105                 110

Cys Asp Glu Asp Ser Ala Thr Glu Thr Cys Tyr Thr Tyr Asp Arg Asn
        115                 120                 125

Lys Cys Tyr Thr Ala Val Val Pro Leu Val Tyr Gly Gly Glu Thr Lys
    130                 135                 140

Met Val Glu Thr Ala Leu Thr Pro Asp Ala Cys Tyr Pro Asp
145                 150                 155

<210> SEQ ID NO 50
<211> LENGTH: 297
<212> TYPE: PRT
<213> ORGANISM: Homo sapiens

<400> SEQUENCE: 50

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
                20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
        50                  55                  60

Ala Leu Gly Gly Leu Leu Met Ile Pro Ala Gly Ile Tyr Ala Pro Ile
65                  70                  75                  80

```
Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 51
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
caggttcagc tgcagcagcc cggagccgag ctggtcaaac ctggcgctag tgtgaaaatg      60
tcatgcaagg catccggata cacattcact agctataaca tgcactgggt gaagcagacc     120
cccggcaggg gtctggagtg gatcggagct atctaccccg gcaacggaga cacatcttat     180
aatcagaagt ttaaaggcaa ggccaccctg acagctgata gtccagctc taccgcatac     240 atgcagctga gttcactgac aagcgaggac tccgccgtgt actattgcgc ccggtccact     300
tactatggcg agattggta tttcaatgtg tggggagcag gcaccacagt caccgtctcg     360
agcggcagtg ctagcgcccc aacccttttc cccctcgtct cctgtgagaa ttccccgtcg     420
gatacgagca gcgtggccgt tggctgcctc gcacaggact ccttcccga ctccatcact     480 ttctcctgga atacaagaa caactctgac atcagcagca cccggggctt ccatcagtc     540 ctgagagggg gcaagtacgc agccacctca caggtgctgc tgccttccaa ggacgtcatg     600
cagggcacag acgaacacgt ggtgtgcaaa gtccagcacc ccaacggcaa caaagaaaag     660
aacgtgcctc ttccagtgat tgctgagctg cctcccaaag tgagcgtctt cgtcccaccc     720
cgcgacggct tcttcggcaa ccccccgcaag tccaagctca tctgccaggc cacgggtttc     780
```

```
agtccccggc agattcaggt gtcctggctg cgcgagggga agcaggtggg gtctggcgtc    840
accacggacc aggtgcaggc tgaggccaaa gagtctgggc ccacgaccta caaggtgacc    900
agcacactga ccatcaaaga gagcgactgg ctcagccaga gcatgttcac ctgccgcgtg    960
gatcacaggg gcctgacctt ccagcagaat gcgtcctcca tgtgtgtccc cgatcaagac   1020
acagccatcc gggtcttcgc catcccccca tcctttgcca gcatcttcct caccaagtcc   1080
accaagttga cctgcctggt cacagacctg accacctatg acagcgtgac catctcctgg   1140
acccgccaga atggcgaagc tgtgaaaacc cacaccaaca tctccgagag ccaccccaat   1200
gccactttca gcgccgtggg tgaggccagc atctgcgagg atgactggaa ttccggggag   1260
aggttcacgt gcaccgtgac ccacacagac ctgccctcgc cactgaagca gaccatctcc   1320
cggcccaagg ggtggccct gcacaggccc gatgtctact tgctgccacc agcccgggag   1380
cagctgaacc tgcgggagtc ggccaccatc acgtgcctgg tgacgggctt ctctcccgcg   1440
gacgtcttcg tgcagtggat gcagaggggg cagcccttgt ccccggagaa gtatgtgacc   1500
agcgccccaa tgcctgagcc ccaggcccca ggccggtact tcgcccacag catcctgacc   1560
gtgtccgaag aggaatggaa cacggggag acctacacct gcgtggtggc ccatgaggcc   1620
ctgcccaaca gggtcaccga ggaccgtg acaagtcca ccggtaaacc caccctgtac     1680
aacgtgtccc tggtcatgtc cgacacagct ggcacctgct actga                 1725
```

<210> SEQ ID NO 52
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190
```

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
            275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
    355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
    435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Glu Trp Asn Thr
    515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 53
<211> LENGTH: 642
<212> TYPE: DNA
<213> ORGANISM: Artificial Sequence
<220> FEATURE:

<223> OTHER INFORMATION: Description of Artificial Sequence: Synthetic
       polynucleotide

<400> SEQUENCE: 53

```
caaattgtgc tgtctcagag tccagctatc ctgagcgcat ctcccggaga gaaggtgacc      60
atgacatgca gagcctccag ctctgtctcc tacatccact ggttccagca gaagcccggc     120
tcctccccaa aaccctggat ctacgccacc tctaacctgg ctagtggtgt gcctgtcagg     180
tttagtggat cagggtccgg caccagctac tctctgacaa tcagccgggt ggaggctgaa     240
gacgccgcta catactattg ccagcagtgg acttctaatc ccctaccctt cggcggaggg     300
acaaagctgg agatcaagcg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642
```

<210> SEQ ID NO 54
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 55
<211> LENGTH: 1728
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
gaggtgcagc tggtgcagtc cggcgccgag gtgaagaagc ccggcgagtc cctgaagatc      60
tcctgcaagg ctccggcta ctccttcacc tcctactgga tcggctgggt gaggcagatg     120
cccggcaagg gcctggagtg gatgggcatc atctacccccg cgactccga caccaggtac    180
tcccctcct tccagggcca ggtgaccatc tccgccgaca gtccatcac caccgcctac     240
ctgcagtggt cctccctgaa ggcctccgac accgccatgt actactgcgc caggcacccc    300
tcctacggct ccggctcccc caacttcgac tactggggcc agggcacccct ggtgaccgtg   360
tcctccggca gtgctagcgc cccaacccctt ttccccctcg tctcctgtga gaattccccg   420
tcggatacga gcagcgtggc cgttggctgc ctcgcacagg acttccttcc cgactccatc    480
actttctcct ggaaatacaa gaacaactct gacatcagca gcacccgggg cttcccatca    540
gtcctgagag ggggcaagta cgcagccacc tcacaggtgc tgctgccttc caaggacgtc    600
atgcagggca cagacgaaca cgtggtgtgc aaagtccagc accccaacgg caacaaagaa   660
aagaacgtgc ctcttccagt gattgctgag ctgcctccca agtgagcgt cttcgtccca    720
cccgcgacg gcttcttcgg caaccccgc aagtccaagc tcatctgcca ggccacgggt    780
ttcagtcccc ggcagattca ggtgtcctgg ctgcgcgagg ggaagcaggt ggggtctggc    840
gtcaccacgg accaggtgca ggctgaggcc aaagagtctg gcccacgac ctacaaggtg    900
accagcacac tgaccatcaa agagagcgac tggctcagcc agagcatgtt cacctgccgc    960
gtggatcaca ggggcctgac cttccagcag aatgcgtcct ccatgtgtgt ccccgatcaa   1020
gacacagcca tccgggtctt cgccatcccc ccatcctttg ccagcatctt cctcaccaag   1080
tccaccaagt tgacctgcct ggtcacagac ctgaccacct atgacagcgt gaccatctcc   1140
tggacccgcc agaatggcga agctgtgaaa acccacacca acatctccga gagccacccc   1200
aatgccactt tcagcgccgt gggtgaggcc agcatctgcg aggatgactg gaattccggg   1260
gagaggttca cgtgcaccgt gacccacaca gacctgccct cgccactgaa gcagaccatc   1320
tcccggccca aggggggtggc cctgcacagg cccgatgtct acttgctgcc accagcccgg   1380
gagcagctga acctgcggga gtcggccacc atcacgtgcc tggtgacggg cttctctccc   1440
gcggacgtct tcgtgcagtg gatgcagagg gggcagcccc tgtccccgga gaagtatgtg   1500
accagcgccc caatgcctga gccccaggcc ccaggccggt acttcgccca cagcatcctg   1560
accgtgtccg aagaggaatg gaacacgggg gagacctaca cctgcgtggt ggcccatgag   1620
gccctgccca cagggtcac cgagaggacc gtggacaagt ccaccggtaa acccacccctg   1680
tacaacgtgt ccctggtcat gtccgacaca gctggcacct gctactga              1728
```

<210> SEQ ID NO 56
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Ser Tyr Gly Gly Ser Pro Asn Phe Asp Tyr Trp
            100                 105                 110

Gly Gln Gly Thr Leu Val Thr Val Ser Ser Gly Ser Ala Ser Ala Pro
        115                 120                 125

Thr Leu Phe Pro Leu Val Ser Cys Glu Asn Ser Pro Ser Asp Thr Ser
    130                 135                 140

Ser Val Ala Val Gly Cys Leu Ala Gln Asp Phe Leu Pro Asp Ser Ile
145                 150                 155                 160

Thr Phe Ser Trp Lys Tyr Lys Asn Asn Ser Asp Ile Ser Ser Thr Arg
                165                 170                 175

Gly Phe Pro Ser Val Leu Arg Gly Gly Lys Tyr Ala Ala Thr Ser Gln
            180                 185                 190

Val Leu Leu Pro Ser Lys Asp Val Met Gln Gly Thr Asp Glu His Val
        195                 200                 205

Val Cys Lys Val Gln His Pro Asn Gly Asn Lys Glu Lys Asn Val Pro
    210                 215                 220

Leu Pro Val Ile Ala Glu Leu Pro Pro Lys Val Ser Val Phe Val Pro
225                 230                 235                 240

Pro Arg Asp Gly Phe Phe Gly Asn Pro Arg Lys Ser Lys Leu Ile Cys
                245                 250                 255

Gln Ala Thr Gly Phe Ser Pro Arg Gln Ile Gln Val Ser Trp Leu Arg
            260                 265                 270

Glu Gly Lys Gln Val Gly Ser Gly Val Thr Thr Asp Gln Val Gln Ala
        275                 280                 285

Glu Ala Lys Glu Ser Gly Pro Thr Thr Tyr Lys Val Thr Ser Thr Leu
    290                 295                 300

Thr Ile Lys Glu Ser Asp Trp Leu Ser Gln Ser Met Phe Thr Cys Arg
305                 310                 315                 320

Val Asp His Arg Gly Leu Thr Phe Gln Gln Asn Ala Ser Ser Met Cys
                325                 330                 335

Val Pro Asp Gln Asp Thr Ala Ile Arg Val Phe Ala Ile Pro Pro Ser
            340                 345                 350

Phe Ala Ser Ile Phe Leu Thr Lys Ser Thr Lys Leu Thr Cys Leu Val
        355                 360                 365

Thr Asp Leu Thr Thr Tyr Asp Ser Val Thr Ile Ser Trp Thr Arg Gln
    370                 375                 380

Asn Gly Glu Ala Val Lys Thr His Thr Asn Ile Ser Glu Ser His Pro
385                 390                 395                 400

Asn Ala Thr Phe Ser Ala Val Gly Glu Ala Ser Ile Cys Glu Asp Asp
                405                 410                 415
```

Trp Asn Ser Gly Glu Arg Phe Thr Cys Thr Val His Thr Asp Leu
            420                 425                 430

Pro Ser Pro Leu Lys Gln Thr Ile Ser Arg Pro Lys Gly Val Ala Leu
        435                 440                 445

His Arg Pro Asp Val Tyr Leu Leu Pro Pro Ala Arg Glu Gln Leu Asn
450                 455                 460

Leu Arg Glu Ser Ala Thr Ile Thr Cys Leu Val Thr Gly Phe Ser Pro
465                 470                 475                 480

Ala Asp Val Phe Val Gln Trp Met Gln Arg Gly Gln Pro Leu Ser Pro
                485                 490                 495

Glu Lys Tyr Val Thr Ser Ala Pro Met Pro Glu Pro Gln Ala Pro Gly
            500                 505                 510

Arg Tyr Phe Ala His Ser Ile Leu Thr Val Ser Glu Glu Trp Asn
        515                 520                 525

Thr Gly Glu Thr Tyr Thr Cys Val Val Ala His Glu Ala Leu Pro Asn
            530                 535                 540

Arg Val Thr Glu Arg Thr Val Asp Lys Ser Thr Gly Lys Pro Thr Leu
545                 550                 555                 560

Tyr Asn Val Ser Leu Val Met Ser Asp Thr Ala Gly Thr Cys Tyr
                565                 570                 575

<210> SEQ ID NO 57
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacatcgtga tgacccagac cccctgtcc tcccccgtga ccctgggcca gcccgcctcc      60
atctcctgca ggtcctccca gtccctggtg tactccgacg gcaacaccta cctgtcctgg     120
ctgcagcaga ggcccggcca gccccccagg ctgctgatct acaagatctc caacaggttc     180
tccggcgtgc ccgacaggtt ctccggctcc ggcgccggca ccgacttcac cctgaagatc     240
tccagggtgg aggccgagga cgtgggcgtg tactactgcg tgcaggccac ccagttcccc     300
ctgaccttcg gcggcggcac caaggtggag atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 58
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser

```
                    20                  25                  30
Asp Gly Asn Thr Tyr Leu Ser Trp Leu Gln Gln Arg Pro Gly Gln Pro
                35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Val Gln Ala
                 85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 59
<211> LENGTH: 353
<212> TYPE: PRT
<213> ORGANISM: Homo sapiens

<400> SEQUENCE: 59

Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
 65                  70                  75                  80

Lys Ser Val Thr Cys His Val Lys His Tyr Thr Asn Pro Ser Gln Asp
                 85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175
```

Arg Asp Leu Cys Gly Cys Tyr Ser Val Ser Ser Val Leu Pro Gly Cys
              180                 185                 190

Ala Glu Pro Trp Asn His Gly Lys Thr Phe Thr Cys Thr Ala Ala Tyr
          195                 200                 205

Pro Glu Ser Lys Thr Pro Leu Thr Ala Thr Leu Ser Lys Ser Gly Asn
      210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
              245                 250                 255

Pro Lys Asp Val Leu Val Arg Trp Leu Gln Gly Ser Gln Glu Leu Pro
          260                 265                 270

Arg Glu Lys Tyr Leu Thr Trp Ala Ser Arg Gln Glu Pro Ser Gln Gly
      275                 280                 285

Thr Thr Thr Phe Ala Val Thr Ser Ile Leu Arg Val Ala Ala Glu Asp
  290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
              325                 330                 335

Thr His Val Asn Val Ser Val Val Met Ala Glu Val Asp Gly Thr Cys
          340                 345                 350

Tyr

<210> SEQ ID NO 60
<211> LENGTH: 340
<212> TYPE: PRT
<213> ORGANISM: Homo sapiens

<400> SEQUENCE: 60

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
              20                  25                  30

Pro Gln Glu Pro Leu Ser Val Thr Trp Ser Glu Ser Gly Gln Asn Val
          35                  40                  45

Thr Ala Arg Asn Phe Pro Pro Ser Gln Asp Ala Ser Gly Asp Leu Tyr
      50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
              85                  90                  95

Val Thr Val Pro Cys Pro Val Pro Pro Pro Pro Cys Cys His Pro
          100                 105                 110

Arg Leu Ser Leu His Arg Pro Ala Leu Glu Asp Leu Leu Leu Gly Ser
      115                 120                 125

Glu Ala Asn Leu Thr Cys Thr Leu Thr Gly Leu Arg Asp Ala Ser Gly
  130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
              165                 170                 175

Pro Gly Cys Ala Gln Pro Trp Asn His Gly Glu Thr Phe Thr Cys Thr
          180                 185                 190

```
Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 61
<211> LENGTH: 764
<212> TYPE: PRT
<213> ORGANISM: Homo sapiens

<400> SEQUENCE: 61

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220
```

```
Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
            245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
        290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
                340                 345                 350

Pro Arg Ser Pro Thr Val Val Lys Gly Val Ala Gly Ser Val Ala
        355                 360                 365

Val Leu Cys Pro Tyr Asn Arg Lys Glu Ser Lys Ser Ile Lys Tyr Trp
370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
            405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
        450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
        530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
            565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
        610                 615                 620

Val Asp Ser Gly Ser Ser Glu Glu Gln Gly Gly Ser Ser Arg Ala Leu
625                 630                 635                 640
```

```
Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760
```

<210> SEQ ID NO 62
<211> LENGTH: 585
<212> TYPE: PRT
<213> ORGANISM: Homo sapiens

<400> SEQUENCE: 62

```
Lys Ser Pro Ile Phe Gly Pro Glu Val Asn Ser Val Glu Gly Asn
1               5                   10                  15

Ser Val Ser Ile Thr Cys Tyr Tyr Pro Pro Thr Ser Val Asn Arg His
            20                  25                  30

Thr Arg Lys Tyr Trp Cys Arg Gln Gly Ala Arg Gly Gly Cys Ile Thr
        35                  40                  45

Leu Ile Ser Ser Glu Gly Tyr Val Ser Ser Lys Tyr Ala Gly Arg Ala
    50                  55                  60

Asn Leu Thr Asn Phe Pro Glu Asn Gly Thr Phe Val Val Asn Ile Ala
65                  70                  75                  80

Gln Leu Ser Gln Asp Asp Ser Gly Arg Tyr Lys Cys Gly Leu Gly Ile
                85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
    130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
    210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255
```

```
Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
    290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
                325                 330                 335

Ser Pro Thr Val Val Lys Gly Val Ala Gly Ser Val Ala Val Leu
            340                 345                 350

Cys Pro Tyr Asn Arg Lys Glu Ser Lys Ser Ile Lys Tyr Trp Cys Leu
            355                 360                 365

Trp Glu Gly Ala Gln Asn Gly Arg Cys Pro Leu Leu Val Asp Ser Glu
    370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
                405                 410                 415

Asp Ala Gly Phe Tyr Trp Cys Leu Thr Asn Gly Asp Thr Leu Trp Arg
            420                 425                 430

Thr Thr Val Glu Ile Lys Ile Ile Glu Gly Glu Pro Asn Leu Lys Val
            435                 440                 445

Pro Gly Asn Val Thr Ala Val Leu Gly Glu Thr Leu Lys Val Pro Cys
450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
            485                 490                 495

Lys Ala Phe Val Asn Cys Asp Glu Asn Ser Arg Leu Val Ser Leu Thr
            500                 505                 510

Leu Asn Leu Val Thr Arg Ala Asp Glu Gly Trp Tyr Trp Cys Gly Val
            515                 520                 525

Lys Gln Gly His Phe Tyr Gly Glu Thr Ala Ala Val Tyr Val Ala Val
            530                 535                 540

Glu Glu Arg Lys Ala Ala Gly Ser Arg Asp Val Ser Leu Ala Lys Ala
545                 550                 555                 560

Asp Ala Ala Pro Asp Glu Lys Val Leu Asp Ser Gly Phe Arg Glu Ile
            565                 570                 575

Glu Asn Lys Ala Ile Gln Asp Pro Arg
            580                 585

<210> SEQ ID NO 63
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Trp Ser Tyr Ile Ile Leu Phe Leu Val Ala Thr Ala Thr Gly
1               5                   10                  15

Val His Ser Gln Val Gln Leu Val Gln Ser Gly Ala Glu Val Lys Lys
```

```
                 20                  25                  30
Pro Gly Ala Ser Val Lys Val Ser Cys Lys Ala Ser Gly Tyr Thr Phe
             35                  40                  45
Ile Ser Tyr Thr Met His Trp Val Arg Gln Ala Pro Gly Gln Gly Leu
         50                  55                  60
Glu Trp Met Gly Tyr Ile Asn Pro Arg Ser Gly Tyr Thr His Tyr Asn
 65                  70                  75                  80
Gln Lys Leu Lys Asp Lys Ala Thr Leu Thr Ala Asp Lys Ser Ala Ser
                 85                  90                  95
Thr Ala Tyr Met Glu Leu Ser Ser Leu Arg Ser Glu Asp Thr Ala Val
             100                 105                 110
Tyr Tyr Cys Ala Arg Ser Ala Tyr Tyr Asp Tyr Asp Gly Phe Ala Tyr
         115                 120                 125
Trp Gly Gln Gly Thr Leu Val Thr Val Ser Ser Gly Gly Gly Gly Ser
     130                 135                 140
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
                 165                 170                 175
Cys Ser Ala Ser Ser Val Ser Tyr Met Asn Trp Tyr Gln Gln Lys
             180                 185                 190
Pro Gly Lys Ala Pro Lys Arg Leu Ile Tyr Asp Thr Ser Lys Leu Ala
         195                 200                 205
Ser Gly Val Pro Ser Arg Phe Ser Gly Ser Gly Ser Gly Thr Asp Phe
     210                 215                 220
Thr Leu Thr Ile Ser Ser Leu Gln Pro Glu Asp Phe Ala Thr Tyr Tyr
225                 230                 235                 240
Cys Gln Gln Trp Ser Ser Asn Pro Pro Thr Phe Gly Gly Gly Thr Lys
                 245                 250                 255
Leu Glu Ile Lys Gly Gly Gly Gly Ser Gly Gly Gly Gly Ser Gly Gly
             260                 265                 270
Gly Gly Ser Gln Glu Asp Glu Arg Ile Val Leu Val Asp Asn Lys Cys
         275                 280                 285
Lys Cys Ala Arg Ile Thr Ser Arg Ile Ile Arg Ser Ser Glu Asp Pro
     290                 295                 300
Asn Glu Asp Ile Val Glu Arg Asn Ile Arg Ile Ile Val Pro Leu Asn
305                 310                 315                 320
Asn Arg Glu Asn Ile Ser Asp Pro Thr Ser Pro Leu Arg Thr Arg Phe
                 325                 330                 335
Val Tyr His Leu Ser Asp Leu Cys Lys Lys Cys Asp Pro Thr Glu Val
             340                 345                 350
Glu Leu Asp Asn Gln Ile Val Thr Ala Thr Gln Ser Asn Ile Cys Asp
         355                 360                 365
Glu Asp Ser Ala Thr Glu Thr Cys Tyr Thr Tyr Asp Arg Asn Lys Cys
     370                 375                 380
Tyr Thr Ala Val Val Pro Leu Val Tyr Gly Gly Glu Thr Lys Met Val
385                 390                 395                 400
Glu Thr Ala Leu Thr Pro Asp Ala Cys Tyr Pro Asp
                 405                 410

<210> SEQ ID NO 64
<211> LENGTH: 393
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Ser Ala
145                 150                 155                 160

Ser Ser Ser Val Ser Tyr Met Asn Trp Tyr Gln Gln Lys Pro Gly Lys
                165                 170                 175

Ala Pro Lys Arg Leu Ile Tyr Asp Thr Ser Lys Leu Ala Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Trp Ser Ser Asn Pro Pro Thr Phe Gly Gly Gly Thr Lys Leu Glu Ile
225                 230                 235                 240

Lys Gly Gly Gly Gly Ser Gly Gly Gly Gly Ser Gly Gly Gly Gly Ser
                245                 250                 255

Gln Glu Asp Glu Arg Ile Val Leu Val Asp Asn Lys Cys Lys Cys Ala
            260                 265                 270

Arg Ile Thr Ser Arg Ile Ile Arg Ser Ser Glu Asp Pro Asn Glu Asp
        275                 280                 285

Ile Val Glu Arg Asn Ile Arg Ile Ile Val Pro Leu Asn Asn Arg Glu
    290                 295                 300

Asn Ile Ser Asp Pro Thr Ser Pro Leu Arg Thr Arg Phe Val Tyr His
305                 310                 315                 320

Leu Ser Asp Leu Cys Lys Lys Cys Asp Pro Thr Glu Val Glu Leu Asp
                325                 330                 335

Asn Gln Ile Val Thr Ala Thr Gln Ser Asn Ile Cys Asp Glu Asp Ser
            340                 345                 350

Ala Thr Glu Thr Cys Tyr Thr Tyr Asp Arg Asn Lys Cys Tyr Thr Ala
        355                 360                 365

Val Val Pro Leu Val Tyr Gly Gly Glu Thr Lys Met Val Glu Thr Ala
    370                 375                 380

Leu Thr Pro Asp Ala Cys Tyr Pro Asp
```

```
<210> SEQ ID NO 65
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Ser Gly Gly Gly Ser Gln Val
                165                 170                 175

Gln Leu Val Gln Ser Gly Ala Glu Val Lys Lys Pro Gly Ala Ser Val
            180                 185                 190

Lys Val Ser Cys Lys Ala Ser Gly Tyr Thr Phe Ile Ser Tyr Thr Met
        195                 200                 205

His Trp Val Arg Gln Ala Pro Gly Gln Gly Leu Glu Trp Met Gly Tyr
    210                 215                 220

Ile Asn Pro Arg Ser Gly Tyr Thr His Tyr Asn Gln Lys Leu Lys Asp
225                 230                 235                 240

Lys Ala Thr Leu Thr Ala Asp Lys Ser Ala Ser Thr Ala Tyr Met Glu
                245                 250                 255

Leu Ser Ser Leu Arg Ser Glu Asp Thr Ala Val Tyr Tyr Cys Ala Arg
            260                 265                 270

Ser Ala Tyr Tyr Asp Tyr Asp Gly Phe Ala Tyr Trp Gly Gln Gly Thr
        275                 280                 285

Leu Val Thr Val Ser Ser Gly Gly Gly Ser Gly Gly Gly Gly Ser
    290                 295                 300

Gly Gly Gly Gly Ser Asp Ile Gln Met Thr Gln Ser Pro Ser Ser Leu
305                 310                 315                 320

Ser Ala Ser Val Gly Asp Arg Val Thr Ile Thr Cys Ser Ala Ser Ser
                325                 330                 335

Ser Val Ser Tyr Met Asn Trp Tyr Gln Gln Lys Pro Gly Lys Ala Pro
            340                 345                 350
```

```
Lys Arg Leu Ile Tyr Asp Thr Ser Lys Leu Ala Ser Gly Val Pro Ser
            355                 360                 365

Arg Phe Ser Gly Ser Gly Ser Gly Thr Asp Phe Thr Leu Thr Ile Ser
        370                 375                 380

Ser Leu Gln Pro Glu Asp Phe Ala Thr Tyr Tyr Cys Gln Gln Trp Ser
385                 390                 395                 400

Ser Asn Pro Pro Thr Phe Gly Gly Gly Thr Lys Leu Glu Ile Lys
                405                 410                 415

<210> SEQ ID NO 66
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
    130                 135                 140

Gly Gly Ser Gly Gly Gly Ser Gln Val Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Thr Phe Ile Ser Tyr Thr Met His Trp Val Arg Gln Ala
            180                 185                 190

Pro Gly Gln Gly Leu Glu Trp Met Gly Tyr Ile Asn Pro Arg Ser Gly
        195                 200                 205

Tyr Thr His Tyr Asn Gln Lys Leu Lys Asp Lys Ala Thr Leu Thr Ala
    210                 215                 220

Asp Lys Ser Ala Ser Thr Ala Tyr Met Glu Leu Ser Ser Leu Arg Ser
225                 230                 235                 240

Glu Asp Thr Ala Val Tyr Tyr Cys Ala Arg Ser Ala Tyr Tyr Asp Tyr
                245                 250                 255

Asp Gly Phe Ala Tyr Trp Gly Gln Gly Thr Leu Val Thr Val Ser Ser
            260                 265                 270

Gly Gly Gly Gly Ser Gly Gly Gly Ser Gly Gly Gly Ser Asp
        275                 280                 285

Ile Gln Met Thr Gln Ser Pro Ser Ser Leu Ser Ala Ser Val Gly Asp
    290                 295                 300
```

```
Arg Val Thr Ile Thr Cys Ser Ala Ser Ser Val Ser Tyr Met Asn
305                 310                 315                 320

Trp Tyr Gln Gln Lys Pro Gly Lys Ala Pro Lys Arg Leu Ile Tyr Asp
            325                 330                 335

Thr Ser Lys Leu Ala Ser Gly Val Pro Ser Arg Phe Ser Gly Ser Gly
        340                 345                 350

Ser Gly Thr Asp Phe Thr Leu Thr Ile Ser Ser Leu Gln Pro Glu Asp
            355                 360                 365

Phe Ala Thr Tyr Tyr Cys Gln Gln Trp Ser Ser Asn Pro Pro Thr Phe
370                 375                 380

Gly Gly Gly Thr Lys Leu Glu Ile Lys
385                 390

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Gly Gly Ser Gly Gly Gly Gly Ser Gly Gly Gly Gly Ser
1               5                   10                  15

<210> SEQ ID NO 68
<211> LENGTH: 1239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atgggctggt cctacatcat cctcttcctc gtggccacag ccacaggcgt ccatagccag      60
gtgcagctgg tgcagtccgg cgccgaagtg aagaagcctg gcgccagcgt gaaggtgagc     120
tgcaaggctt ccggctacac cttcatctcc tacaccatgc actgggtgag gcaagctcct     180
ggccagggcc tggagtggat gggatacatc aaccctcggt ccggctatac ccactacaat     240
cagaagctga aggacaaggc caccctgacc gctgacaagt ccgcctccac cgcttacatg     300
gagctgtcct ccctgaggtc cgaggacacc gccgtgtact actgtgccag gtccgcctac     360
tacgactacg acggattcgc ttactggggc cagggcaccc tggtgacagt gagctccgga     420
ggaggaggca gcggcggcgg cggcagcggc ggcggcggca gcgatatcca gatgacccag     480
agcccttcca gcctgtccgc ttccgtgggc gacagggtga ccatcacctg cagcgcttcc     540
tcctccgtgt cctacatgaa ctggtaccag cagaagcctg gcaaggcccc caagaggctg     600
atctacgaca cctccaagct ggcctccgga gtgccttcca ggttcagcgg ctccggctcc     660
ggaaccgact caccctgac cattagctcc ctgcagcccg aggacttcgc cacctactac     720
tgccagcagt ggtccagcaa ccctcccacc ttcggcggcg gcacaaagct ggagatcaag     780
ggaggaggag gatccggtgg tgtggttct ggcggaggtg atcccaaga agatgaaagg     840 attgttcttg ttgacaacaa atgtaagtgt gcccggatta cttccaggat catccgttct     900
tccgaagatc ctaatgagga cattgtggag agaaacatcc gaattattgt tcctctgaac     960
aacagggaga atatctctga tcccacctca ccattgagaa ccagatttgt gtaccatttg    1020
tctgacctct gtaaaaaatg tgatcctaca gaagtggagc tggataatca gatagttact    1080
```

```
gctacccaga gcaatatctg tgatgaagac agtgctacag agacctgcta cacttatgac    1140
agaaacaagt gctacacagc tgtggtccca ctcgtatatg gtggtgagac caaaatggtg    1200
gaaacagcct taaccccaga tgcctgctat cctgactga                           1239

<210> SEQ ID NO 69
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atgaagaacc atttgctttt ctggggagtc ctggcggttt ttattaaggc tgttcatgtg      60
aaagcccaag aagatgaaag gattgttctt gttgacaaca aatgtaagtg tgcccggatt     120
acttccagga tcatccgttc ttccgaagat cctaatgagg acattgtgga gagaaacatc     180
cgaattattg ttcctctgaa caacaggagg aatatctctg atcccacctc accattgaga     240
accagatttg tgtaccattt gtctgacctc tgtaaaaaat gtgatcctac agaagtggag     300
ctggataatc agatagttac tgctacccag agcaatatct gtgatgaaga cagtgctaca     360
gagacctgct acacttatga cagaaacaag tgctacacag ctgtggtccc actcgtatat     420
ggtggtgaga ccaaaatggt ggaaacagcc ttaaccccag atgcctgcta tcctgacgga     480
ggaggaggat ccggtggtgg tggttctggc ggaggtggat cccaggtgca gctggtgcag     540
tccggcgccg aagtgaagaa gcctggcgcc agcgtgaagg tgagctgcaa ggcttccggc     600
tacaccttca tctcctacac catgcactgg gtgaggcaag ctcctggcca gggcctggag     660
tggatgggat acatcaaccc tcggtccggc tatacccact acaatcagaa gctgaaggac     720
aaggccaccc tgaccgctga caagtccgcc tccaccgctt acatggagct gtcctccctg     780
aggtccgagg acaccgccgt gtactactgt gccaggtccg cctactacga ctacgacgga     840
ttcgcttact ggggccaggg caccctggtg acagtgagct ccggaggagg aggcagcggt     900
ggtggcggaa gcggtggagg tggcagcgat atccagatga cccagagccc ttccagcctg     960
tccgcttccg tgggcgacag ggtgaccatc acctgcagcg cttcctcctc cgtgtcctac    1020
atgaactggt accagcagaa gcctggcaag gcccccaaga ggctgatcta cgacacctcc    1080
aagctggcct ccggagtgcc ttccaggttc agcggctccg gctccggaac cgacttcacc    1140
ctgaccatta gctccctgca gcccgaggac ttcgccacct actactgcca gcagtggtcc    1200
agcaaccctc ccaccttcgg aggcggcaca aagctggaga tcaagtga                1248
```